US011851699B2

(12) United States Patent
Ellington et al.

(10) Patent No.: US 11,851,699 B2
(45) Date of Patent: *Dec. 26, 2023

(54) STRAND DISPLACEMENT WITH LOOP-MEDIATED ISOTHERMAL AMPLIFICATION

(71) Applicant: Board of Regents, The University of Texas System, Austin, TX (US)

(72) Inventors: Andrew Ellington, Austin, TX (US); Yu Sherry Jiang, Austin, TX (US); Sanchita Bhadra, Austin, TX (US); Bingling Li, Austin, TX (US); Randy Allen Hughes, Austin, TX (US); Yan Du, Austin, TX (US); Jimmy Gollihar, Hewitt, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 296 days.

This patent is subject to a terminal disclaimer.

(21) Appl. No.: 17/168,940

(22) Filed: Feb. 5, 2021

(65) Prior Publication Data

US 2021/0403979 A1 Dec. 30, 2021

Related U.S. Application Data

(63) Continuation of application No. 14/857,216, filed on Sep. 17, 2015, now Pat. No. 10,913,973.

(60) Provisional application No. 62/051,811, filed on Sep. 17, 2014.

(51) Int. Cl.
*C12Q 1/6806* (2018.01)
*C12Q 1/6897* (2018.01)
*C12Q 1/6844* (2018.01)

(52) U.S. Cl.
CPC ......... *C12Q 1/6806* (2013.01); *C12Q 1/6844* (2013.01); *C12Q 1/6897* (2013.01)

(58) Field of Classification Search
CPC ............ C12Q 1/6844; C12Q 2525/301; C12Q 2527/101; C12Q 2531/119; C12Q 2565/107
See application file for complete search history.

(56) References Cited

U.S. PATENT DOCUMENTS

| | | | |
|---|---|---|---|
| 4,469,863 | A | 9/1984 | Ts'o et al. |
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | Mesmaeker et al. |
| 5,637,684 | A | 6/1997 | Cook et al. |
| 5,644,048 | A | 7/1997 | Yau |
| 5,840,867 | A | 11/1998 | Toole et al. |
| 6,544,732 | B1 | 4/2003 | Chee et al. |
| 6,942,771 | B1 | 9/2005 | Kayyem |
| 2006/0068378 | A1 | 3/2006 | Mirkin et al. |
| 2013/0171643 | A1 | 7/2013 | Kubota |

OTHER PUBLICATIONS

Allen, et al., "DNA circuits as amplifiers for the detection of nucleic acids on a paperfluidic platform", Lab on a Chip 2012, 12, 2951-2958.
Aonuma, et al., "A single fluorescence-based LAMP reaction for identifying multiple parasites in mosquitoes", Experimental parasitology 2010, 125, 179-183.
Asiello et al., "Miniaturized isothermal nucleic acid amplification, a review", Lab on a Chip 2011, 11, 1420-1430.
Beaucage, et al., "Deoxynucleoside phosphoramidites—A new class of key intermediates for deoxypolynucleotide synthesis", Tetrahedron Lett. 1981, 1859-1862.
Beaucage et al., "The Functionalization of Oligonucleotides Via Phosphoramidite Derivatives", Tetrahedron 1993, 49(10):1925-1963.
Benenson, et al. "DNA molecule provides a computing machine with both data and fuel", Proceedings of the National Academy of Sciences of the United States of America 2003, 100, 2191-2196.
Bialek, et al., "First Confirmed Cases of Middle East Respiratory Syndrome Coronavirus (MERS-CoV) Infection in the United States, Updated Information on the Epidemiology of MERS-CoV Infection, and Guidance for the Public, Clinicians, and Public Health Authorities—May 2014", Mmwr-Morbid Mortal Wkly 2014, 63:19, 431-436.
Briu, et al., "Synthesis of Oligodeoxynucleoside Phosphorodithioates", J. Am. Chem. Soc. 1989, 111:2321.
Boehme, et al., "Operational Feasibility of Using Loop-Mediated Isothermal Amplification for Diagnosis of Pulmonary Tuberculosis in Microscopy Centers of Developing Countries", Journal of Clinical Microbiology 2007, 45, 1936-1940.
Butterfoss, et al., "Computer-based design of novel protein structures."Annu. Rev. Bioph. Biom. 2006, 35, 49-65.
Carlsson, et al., "Sceening for genetic mutations", Nature 1996, 380:207.
Chen, et al., "Conditionally fluorescent molecular probes for detecting single base changes in double-stranded DNA", Nature Chemistry 2013, 5, 782-789.
Chen, et al., "Rational, modular adaptation of enzyme-free DNA circuits to multiple detection methods", Nucleic acids research 2011, 39(16), 13 pages.
Coleman, et al., "Coronaviruses: Important Emerging Human Pathogens", J Virol 2014, 88, 5209-5212.
Compton, "Nucleic acid sequence-based amplification", J. Nature 1991, 350, 91-92.
Corman, et al., "Assay for Lab confirmation of novel human coronavirus (hCoV-EMC) infections", Eurosurveillance 2012, 9 pages.
Corman, et al., "Performance and clinical validation of the RealStar® MERS-CoV Kit for detection of Middle East respiratory syndrome coronavirus RNA ", J Clin Virol 2014, 60, 168-171.

(Continued)

*Primary Examiner* — Teresa E Strzelecka
(74) *Attorney, Agent, or Firm* — Meunier Carlin & Curfman LLC

(57) ABSTRACT

Disclosed are methods for isothermal nucleic acid amplification and detection.

20 Claims, 45 Drawing Sheets

Specification includes a Sequence Listing.

(56) References Cited

OTHER PUBLICATIONS

Cotten, et al., "Transmission and evolution of the Middle East respiratory syndrome coronavirus in Saudi Arabia: a descriptive genomic study", Lancet 2013, 382, 1993-2002.
Dean, et al., "Comprehensive human genome amplification using multiple displacement amplification", P Natl Acad Sci USA 2002, 99, 5261-5266.
Dempcy, et al., "Synthesis of a thymidyl pentamer of deoxyribonucleic guanidine and binding studies with DNA homopolynucleotides", Proc. Natl. Acad. Sci. USA 1995, 92, 6097-6101.
Dunlap, et al., "Diagnostic Standards and Classification of Tuberculosis in Adults and Children", Sci Assembly Microbiology, T. Am. J. Respir. Crit. Care Med. 2000, 161, 1376-1395.
Egholm, et al., "Peptide Nucleic Acids (PNA). Oglionucleotide Analogues with an Achiral Peptide Backbone", J. Am. Chem. Soc. 1992, 114:1895-1897.
Fang et al Cross-Priming Amplification for Rapid Detection of *Mycobacterium tuberculosis* in Sputum Specimens, Journal of Clinical Microbiology, Mar. 2009, 47:3, 845-847.
Fauci, "An audience with . . . ", Nat Rev Drug Discov 2008, 7, 12.
Griffith, et al., "An Official ATS/IDSA Statement: Diagnosis, Treatment, and Prevention of Nontuberculous Mycobacterial Diseases", A. T. S. D. Am. J. Respir. Crit. Care Med. 2007, 175, 367-416.
Guatelli, et al., "Isothermal, in vitro amplification of nucleic acids by a multienzyme reaction modeled after retrovirl replication", P Natl Acad Sci USA 1990, 87, 1874-1878.
Hall, et al., "Engineered luciferase reporter from a deep sea shrimp utilizing a novel imidazopyrazinone substrate", ACS chemical biology 2012, 7, 1848-1857.
Hall, et al., "Use of Signal-Mediated Amplification of RNA Technology (SMART) to Detect Marine Cyanophage DNA", Biotechniques 2002, 32, 604-611.
Holmes, et al., "Update: Recommendations for Middle East Respiratory Syndrome Coronavirus (MERS-CoV)", Mmwr-Morbid Mortal W 62, 2013, 557-557.
Holmes, "MERS-CoV enigma deepens as reported cases surge", Lancet 383, 2014, 1793-1793.
Iwamoto, et al., "Loop-Mediated Isothermal Amplification for Direct Detection of *Mycobacterium tuberculosis* Complex, *M. avium*, and *M. intracellulare* in Sputum Samples", Journal of Clinical Microbiology 2003, 41, 2616-2622.
Jenkins et al., "The Biosynthesis of Carbocyclic Nucleosides", Chem. Soc. Rev. 1995, pp. 169-176.
Jeffs et al., "Unusual Conformation of a 3'-thioformacetal linkage in a DNA Complex", J. Biomolecular NMR 1994, 34:17.
Jiang et al. "Real-Time Detection of Isothermal Amplification Reactions with Thermostable Catalytic Hairpin Assembly", Journal of the American Chemical Society 2013, 135, 7430-7433.
Kiedrowski et al., "Parabolic growth of a Self-Replicating Hexadeoxynucleotide bearing a 3'-5'-phosphoamidate linkage", Angew. Chem. Intl. Ed. English 1991, 30:423-426.
Koshkin et al., "LNA (Locked Nucleic Acid): An RNA Mimic Forming Exceedingly Stable LNA:LNA Duplexes", J. Am. Chem. Soc. 1998, 120:13252 3.
Kouguchi et al., Homogenous, real-time duplex loop-mediated isothermal amplification using a single fluorophore-labeled primer and an intercalator dye: Its application to the simultaneous detection of Shiga toxin genes 1 and 2 in Shiga toxigenic *Escherichia coli* isolates:, Mol Cell Probe 2010, 24, 190.
Kozak, "Structural Features in Eukaryotic mRNAs That Modulate the Initiation of Translation", J. Biol. Chem. 1991, 266:19867-19870.
Kunkel et al., "Rapid and Efficient Site-Specific Mutagenesis without Phenotypic Selection", Methods Enzymol. 1987, 154, 367-382.
Kurn, N. et al., "Novel Isothermal, Linear Nucleic Acid Amplification Systems for Highly Multiplexed Applications", Clin Chem 51 2005, 1973-1981.
Letsinger et al., "Cationic Oligonucleotides", J. Am. Chem. Soc. 1988, 110:4470-4471.
Letsinger et al., "Efect on pendant groups at phosphorus on binding properties of d-Apa analogues" Nucl. Acids Res. 1986 14:3487.
Letsinger et al., "Hybridization of alternating cationic/anionic oligonucleotides to RNA segments", Nucleoside & Nucleotide 1994, 13:1597-1605.
Letsinger et al., "Phosphoramidate Analogs of Oligonucleotides", J. Org. Chem. 1970, 35:3800-3803.
Li et al., "Adapting Enzyme-Free DNA Circuits to the Detection of Loop-Mediated Isothermal Amplification Reactions", Analytical Chemistry 2012a, 84, 8371-8377.
Li et al., "Probing Spatial Organization of DNA Strands Using Enzyme-Free Hairpin Assembly Circuits", Journal of the American Chemical Society 2012b, 134, 13918-13921.
Li et al., "TAL nucleases (TALNs): hybrid proteins composed of TAL effectors and FokI DNA-cleavage domain", Nucleic acids research 2011, 39, 359-372.
Li et al., "Adapting Enzyme-Free DNA Circuits to the Detection of Loop-Mediated Isothermal Amplification Reactions", Analytical Chemistry 2012c, 84, 8371-8377.
Liang et al., "Multiplex Loop-Mediated Isothermal Amplification Detection by Sequence-Based Barcodes Coupled with Nicking Endonuclease-Mediated Pyrosequencing", Anal Chem 2012, 84, 3758-3763.
Kanehisa, "Use of statistical criteria for screening potential homologies in nucleic acid sequences", Nucleic Acids Res. 1984 12, 203-213.
Mag et al., "Synthesis and selecive cleavage of an oligodeoxynucleotide containing a bridged internucleotide 5'-phosphorothioate linkage", Nucleic Acids Res. 1991, 19:1437-1441.
Mattes et al., "Regulation of MicroRNA by Antagomirs", Am J Respir Cell Mol Biol. 2007, 36(1):8-12.
Matteucci, et al., "Total solid-phase synthesis of Porcine gut gastrin releasing peptide(GRP), a mammalian bombesin", J. Am. Chem. Soc. 1981, 103, 3178-3185.
Meier et al., "Peptide Nucleic Acids (PNAs)—Unusual Properties of Nonionic Oligonucleotide Analogues", Chem. Int. Ed. Engl. 1992, 31 :1008-1010.
Mesmaeker et al., "Comparison of Rigid and Flexible Backbones in Antisense Oligonucleotides", Bioorganic & Medicinal Chem. Lett. 1994, 4:395-398.
Nagamine, et al., "Isolation of Single-Stranded DNA from Loop-Mediated Isothermal Amplification Products", Biochem Bioph Res Co 290, 2002, 1195-1198.
Nielsen, et al., "PNA Hybridized to complementary oligonucleotides obeying the Watson-Crick hydrogen-bonding rules", Nature, 1993, 365:566.
Niu, et al., "Fluorescence detection for DNA using hybridization chain reaction with enzyme-amplification", Chemical Communications 2010, 46, 3089-3091.
Njiru, et al., "Loop-Mediated Isothermal Amplification (LAMP) Method for Rapid Detection of Trypanosoma brucei rhodesiense", Plos Neglected Tropical Diseases 2008, 2:e147, 8 pages.
Notomi, et al., "Loop-Mediated Isothermal Amplification of DNA", Nucleic Acids Research 2000, 28(12): e63, 7 pages.
Osada et al., "MicroRNAs in biological processes and carcinogenesis", Carcinogenesis, 2007, 28(1):2-12.
Pandey, et al., "Development of an in-house loop-mediated isothermal amplification (LAMP) assay for detection of *Mycobacterium tuberculosis* and evaluation in sputum samples of Nepalese patients", Journal of Medical Microbiology 2008, 57, 439-443.
Pauwels, et al., "Biological Activity of New 2-5 A Analogues", Chemica Scripta 1986, 26:141-145.
Rawls, "Promising clinical results and chemical strategies for further improvements delight antisense drug researchers", C & E News, 1997 p. 35-39.
Saiki et al., "Analysis of enzymatically amplified β-globin and HLA-DQ DNA with allele-specific oligonucleotide probes", Nature 1986, 324, 163-166.
Sanders, et al., "Structural Alterations of Gene Complexes by Cystic Fibrosis Sputum", Am J Respir Crit Care Med 2001, 164: 486-93.
Sawai et al., Chem. Lett. 1984, 805-808.
Seeman, "DNA in a material world", Nature 421 2003, 427-431.

(56) References Cited

OTHER PUBLICATIONS

Sprinzl et al.,"Enzymatic Incorporation of ATP and CTP Analogues into the 3' End of tRNA", Eur. J. Biochem. 1977, 81:579-589.
Tanner et al., "Simultaneous multiple target detection in real-time loop-mediated isothermal amplification", BioTechniques 2012, 53:2, 81-89.
Tanner, N.A. et al., Simultaneous multiple target detection in real-time loop-mediated isothermal amplification, Biotechniques vol. 53, Supplemental Material pp. 1-2 (Year: 2012).
Tomita, et al. "Loop-mediated isothermal amplification (LAMP) of gene sequences and simple visual detection of products", Nature Protocols 2008, 3, 877-882.
Unit 2.10, Hybridization Analysis of DNA Blots, John Wiley & Sons, Inc. 2000.
Vincent, et al. "Helicase-dependent isothermal DNA amplification", Embo Rep 5, 2004, 795-800.
Walker, et al., "Strand displacement amplification—an isothermal, in vitro DNA amplification technique", Nucleic Acids Res 20, 1992,1691-1696.
Xu et al. "Cross Priming Amplification: Mechanism and Optimization for Isothermal DNA Amplification", Scientific Reports, Feb. 2012, 2:246.
Xu et al., "Oligonucleotides with Alternating anionic and cationic phosphoramidate", Tetrahedron Lett. 1996, 37:743-746.
Yin et al. "Programming biomolecular self-assembly pathways", Nature 2008, 451, 318-322.
Zaki et al. "Isolation of a novel coronavirus from a man with pneumonia in SaudiArabia", New Engl J Med 367, 2012, 1814-1820.
Zerilli et al. "Methylation-Specific Loop-Mediated Isothermal Amplification for Detecting Hypermethylated DNA in Simplex and Multiplex Formats", Clinical Chemistry 2010, 56, 1287-1296.
Zhang et al., "MicroRNAs and Their Regulatory Roles in Animals and Plants", J Cell Physiol. 2007, 210(2):279-89.
Unit 2.9A, "Analysis of DNA Sequences by Blotting and Hybridization". Southern Blotting. Current Protocols in Molecular Biology 2.9A, (1999) 2.9.1-2.9.14, 15 pages.
Unit 2.9B, "Dot and Slot Blotting of DNA", Current Protocols in Molecular Biology 2.9B, (1999) 2.9.15-2.9.20, 6 pages.
Mesmaker, et al., "Novel Backbone Replacement for Oligonucleotides", Carbohydrate Modifications in Antisense Research, Chapter 2, 1994, pp. 24-39. ACS Symposium Series, vol. 580.
Maddry, et al., "Synthesis of Nonionic Oligonucleotide Analogues", Carbohydrate Modifications in Antisense Research, Chapter 3, pp. 40-51. ACS Symposium Series, vol. 580.
Herdewijn, et al., "Hexopyranosyl-Like Oligonucleotides", Carbohydrate Modifications in Antisense Research, Chapter 6, pp. 80-99. ACS Symposium Series, vol. 580.
Bolli, et al., "$\alpha$-Bicyclo-DNA: Synthesis, Characterization, and Pairing Properties of $\alpha$-DNA-Analogues with Restricted Conformational Flexibility in the Sugar-Phosphate Backbone", Carbohydrate Modifications in Antisense Research Chapter 7, pp. 100-117. ACS Symposium Series, vol. 580.
Yi et al.; "Molecular Zipper: a fluorescent probe for real-time isothermal DNA amplification"; Nucleic Acids Research, 2006, vol. 34, No. 11; Mar. 31, 2006; 5 pages.
Kubota et al.; "FRET-Based Assimilating Probe for Sequence-Specific Real-Time Monitoring of Loop-Mediated Isothermal Amplification (LAMP)"; Biological Engineering Transactions 4(2): 81-100; Jul. 2011; 20 pages.
Clark; "Molecular Biology: Understanding the Genetic Revolution"; 2005; p. 254; 1 page.
Cox et al.; "Molecular Biology: Principles and Practice"; 2012; pp. 221-238, 369-376, 592-593; 30 pages.
Tyagi, S. et al., Molecular Beacons: Probes that Fluoresce upon Hybridization, Nat. Biotechnol., vol. 14, pp. 303-308 (Year: 1996).
Li, Q. et al., A new class of homogeneous nucleic acid probes based on specific displacement hybridization, Nucl. Acids Res., vol. 30, e5, pp. 1-9 (Year: 2002).
Dames, S. et al., Characterization of Aberrant Melting Peaks in Unlabeled Probe Assays, J. Mol. Diagn., vol. 9, pp. 290-296 (Year: 2007).
Li, Q. et al., Development and evaluation of a loop-mediated isothermal amplification assay for rapid detection of lymphocystis disease virus, J. Viral. Meth., vol. 163, pp. 378-384 (Year: 2010).

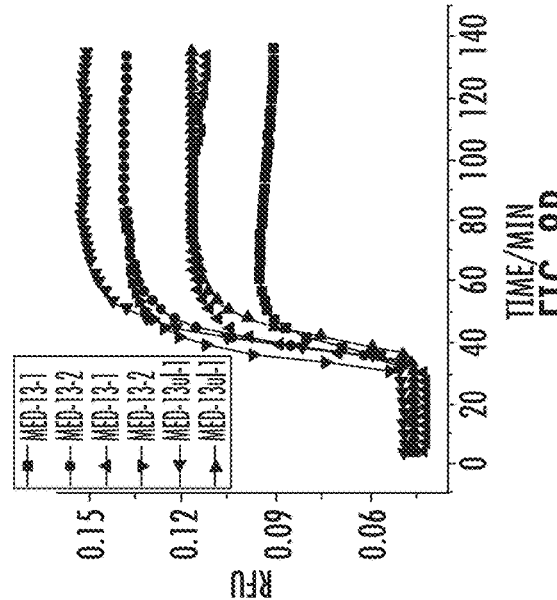
FIG. 8B
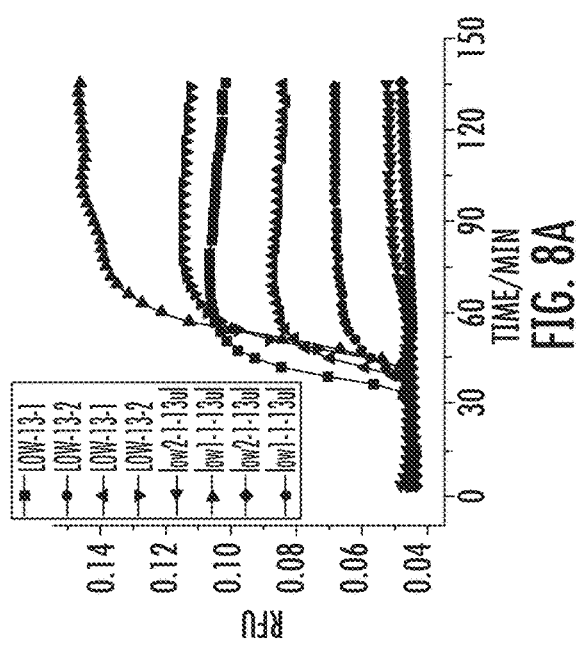
FIG. 8A
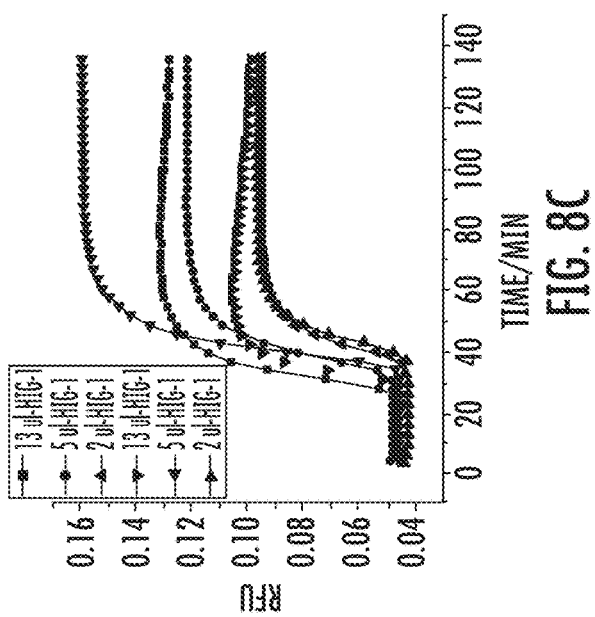
FIG. 8C
FIG. 8D

STRAND DISPLACEMENT WITH LOOP-MEDIATED ISOTHERMAL AMPLIFICATION

I. CROSS-REFERENCE TO RELATED APPLICATIONS

This application is a continuation of U.S. application Ser. No. 14/857,216, filed on Sep. 17, 2015, which claims benefit of U.S. Provisional Application No. 62/051,811, filed Sep. 17, 2014, all of which are hereby incorporated herein by reference in their entirety.

II. ACKNOWLEDGEMENTS

This invention was made with government support under Grant no. EB015403 and Grant no. R01 AI092839 awarded by the National Institutes of Health; and Grant no. HR0011-11-2-0018 and Grant no. HR0011-12-2-0001 awarded by the Defense Advanced Research Projects Agency. The government has certain rights in the invention.

III. BACKGROUND

Molecular self-assembly, a fundamental process underlying the replication and regulation of biological systems, has emerged as an important engineering paradigm for nanotechnology. For example, molecular nanotechnology uses positionally-controlled mechanosynthesis guided by molecular systems. Molecular nanotechnology involves combining physical principles demonstrated by the molecular machinery of life, chemistry, and other nanotechnologies with the systems engineering principles found in modern macroscale factories.

In biological systems, self-assembling and disassembling complexes of proteins and nucleic acids bound to a variety of ligands perform intricate and diverse dynamic functions. Attempts to rationally encode structure and function into synthetic amino and nucleic acid sequences have largely focused on engineering molecules that self-assemble into prescribed target structures without explicit concern for transient system dynamics. See, Butterfoss, G. L. & Kuhlman, Annu. Rev. Bioph. Biom. 35, 49-65 (2006); Seeman, N. C., Nature 421, 427-431(2003). What is needed in the art is a molecular self-assembly system that allows for detection of target nucleic acid.

IV. SUMMARY

Disclosed herein is a method of detecting a nucleic acid, the method comprising a) amplifying a target nucleic acid using an isothermal amplification reaction, wherein the isothermal amplification reaction produces at least one loop product, wherein at least part of the single-stranded portion of the loop product represents the target nucleic acid; b) exposing the loop product of step a) to a strand displacement reporter, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the loop product representing the target nucleic acid; c) allowing the loop product and the strand displacement reporter to interact, wherein interaction between the strand displacement reporter and the target nucleic acid portion of the loop product produces a detectable signal, wherein the signal indicates the presence of the target nucleic acid.

Also disclosed herein is a device for detection of a target nucleic acid, wherein the device comprises: a) an amplification unit, wherein said amplification unit amplifies the target nucleic acid via an isothermal amplification reaction; b) a transducer, wherein said transducer comprises isothermal amplification reporters, wherein said isothermal amplification reporters interact with the target nucleic acid amplification product of step a), and thereby produce a detectable signal; and c) a signal output unit, which displays the detectable signal of step b).

Further disclosed is a non-transitory computer-readable medium with computer-readable instructions stored thereon for use in detecting a nucleic acid, wherein a user inputs instructions, and the computer carries out the steps of: a) amplifying a target nucleic acid using an isothermal amplification reaction, wherein the isothermal amplification reaction produces at least one loop product, wherein at least part of the single-stranded portion of the loop product represents the target nucleic acid; b) exposing the loop product of step a) to a strand displacement reporter, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the loop product representing the target nucleic acid; c) allowing the loop product and the strand displacement reporter to interact, wherein interaction between the strand displacement reporter and the target nucleic acid portion of the loop product produces a detectable signal, wherein the signal indicates the presence of the target nucleic acid, and further wherein the detectable signal is displayed by the computer.

Also disclosed is a method of quantifying a nucleic acid, the method comprising: a) amplifying a nucleic acid sample comprising target nucleic acid as well as false target, wherein said false target comprises a 90% or more sequence identity to a primer binding region of the target nucleic acid; b) exposing the product of step a) to a strand displacement reporter, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the product representing the target nucleic acid, and further wherein the false target is 50% or less complementary to the single-stranded nucleic acid of the strand displacement reporter; c) detecting amplification of false target as well as target nucleic acid; and d) analyzing the results of step c) to quantitate the amount of target nucleic acid present in the nucleic acid sample of step a).

V. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a scheme for a typical LAMP reaction with OSD signal output; the different primers are shown, and "c" denotes complementary sequences. The OSD reporter is shown binding to a loop sequence, here loop F. The fluorescence curve shows LAMP with OSD detection for varying amounts of plasmid rpoB.

FIG. 2A shows a fluorescence curve of LAMP with OSD detection for varying amounts of plasmid BRAF, FIG. 2B shows a 1% agarose gel electrophoresis analysis of the samples from (A).

FIG. 3 shows fluorescence curves of LAMP with OSD to distinguish the wild-type (WT) BRAF gene from the V600E SNP (A) using WT-reporter to detect both WT and SNP templates of different copies and (B) using SNP-reporter to detect both WT and SNP templates of different copies. The topmost sequence is SEQ ID NO: 41. The sequences on the left are SEQ ID NOS: 11 and 12 (top to bottom) and the sequences on the right are also SEQ ID NOS: 11 and 12 (top to bottom).

FIG. 4 shows real-time sequence-specific detection of two analytes in multiplex LAMP using OSD probes. HSV1 and cytB amplicons originating in multiplex LAMP reactions were parsed simultaneously using HSV1-specific TYE665-labeled (Y-axis) and cytB-specific TYE615-labeled (Y-axis) OSD probes. Each multiplex reaction (with traces of the same weight) was seeded with both HSV1 (H) and cytB (C) synthetic template copies in the same order of magnitude: H+C=16+12; $1.6 \times 10^2 + 1.2 \times 10^2$; $1.6 \times 10^3 + 1.2 \times 10^3$; $1.6 \times 10^4 + 1.2 \times 10^4$. With OSD probes, multiplex analysis of different genes can proceed in real-time. Since OSD reaction is highly sequence-specific, multiple OSD reactions do not affect each other during multiplex operation.

FIG. 5 shows a scheme for typical LAMP reaction with CHA signal output. The black loop region of the LAMP amplicon is shown operating as a catalyst for CHA. The CHA product then displaces Reporter Q of the CHA reporter, resulting in fluorescence. The fluorescence curve shows LAMP with CHA detection for varying amounts of plasmid rpoB.

FIG. 8A shows multiple assays on LOW sputum sample with LAMP-OSD detection. FIG. 8B shows multiple assays on MED sputum sample with LAMP-OSD detection. FIG. 8C shows multiple assays on HIG sputum sample with LAMP-OSD detection. FIG. 8D shows a ratio of positive and negative results from all the sputum samples. For example, LOW's positive result is 5/8, negative result is 3/8 means in 8 assays of LOW sample detection, 5 are positive, 3 are negative.

Figure 9:
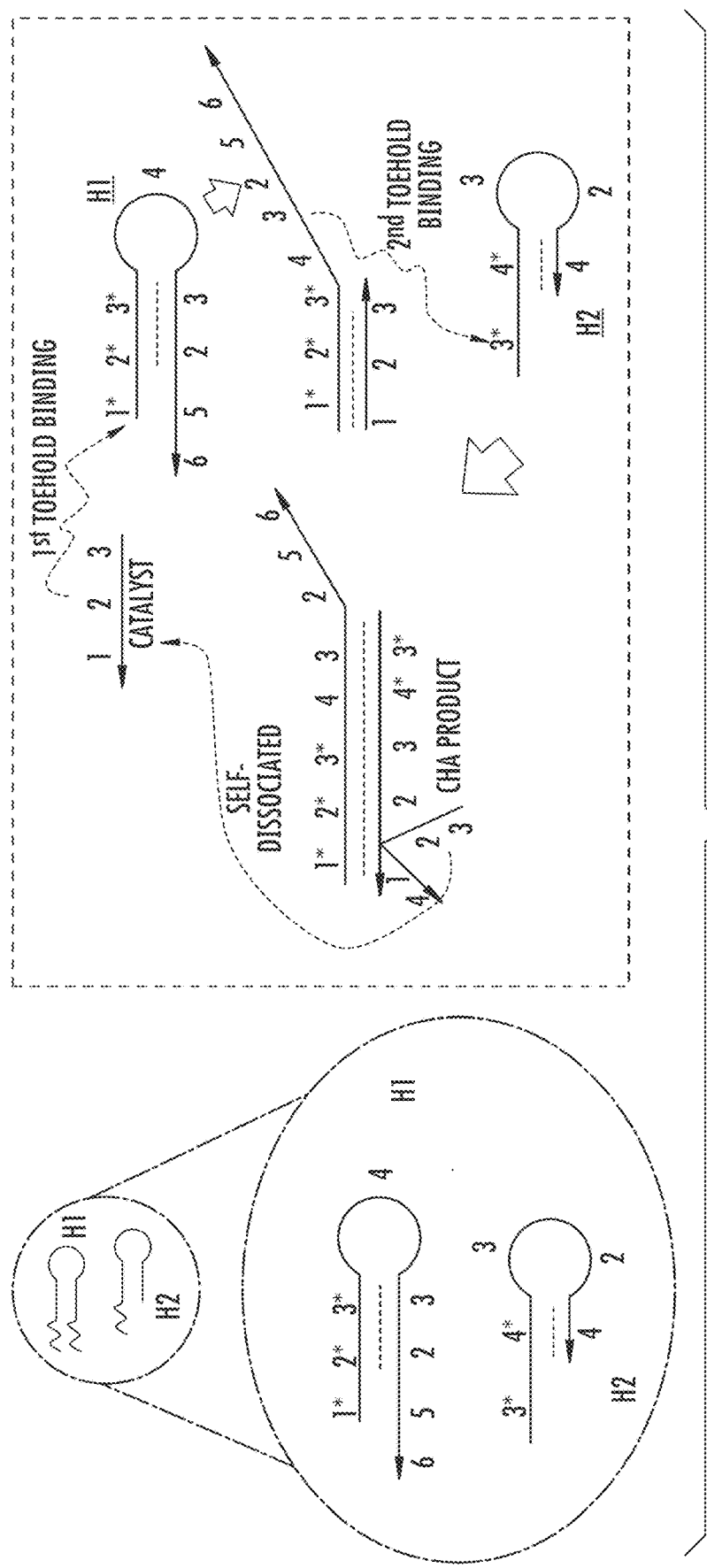

FIG. 9 shows a CHA scheme. Different domains was labeled with numbers and corresponding complementary sequence was labeled with *. The path of CHA includes two steps of toehold-binding mediated strand exchange and one self-dissociation of the toehold. The CHA product as shown in figure contains three free tails (1*; 4*; 2-5-6), which can connect to the downstream signal characterization.

Figure 10:
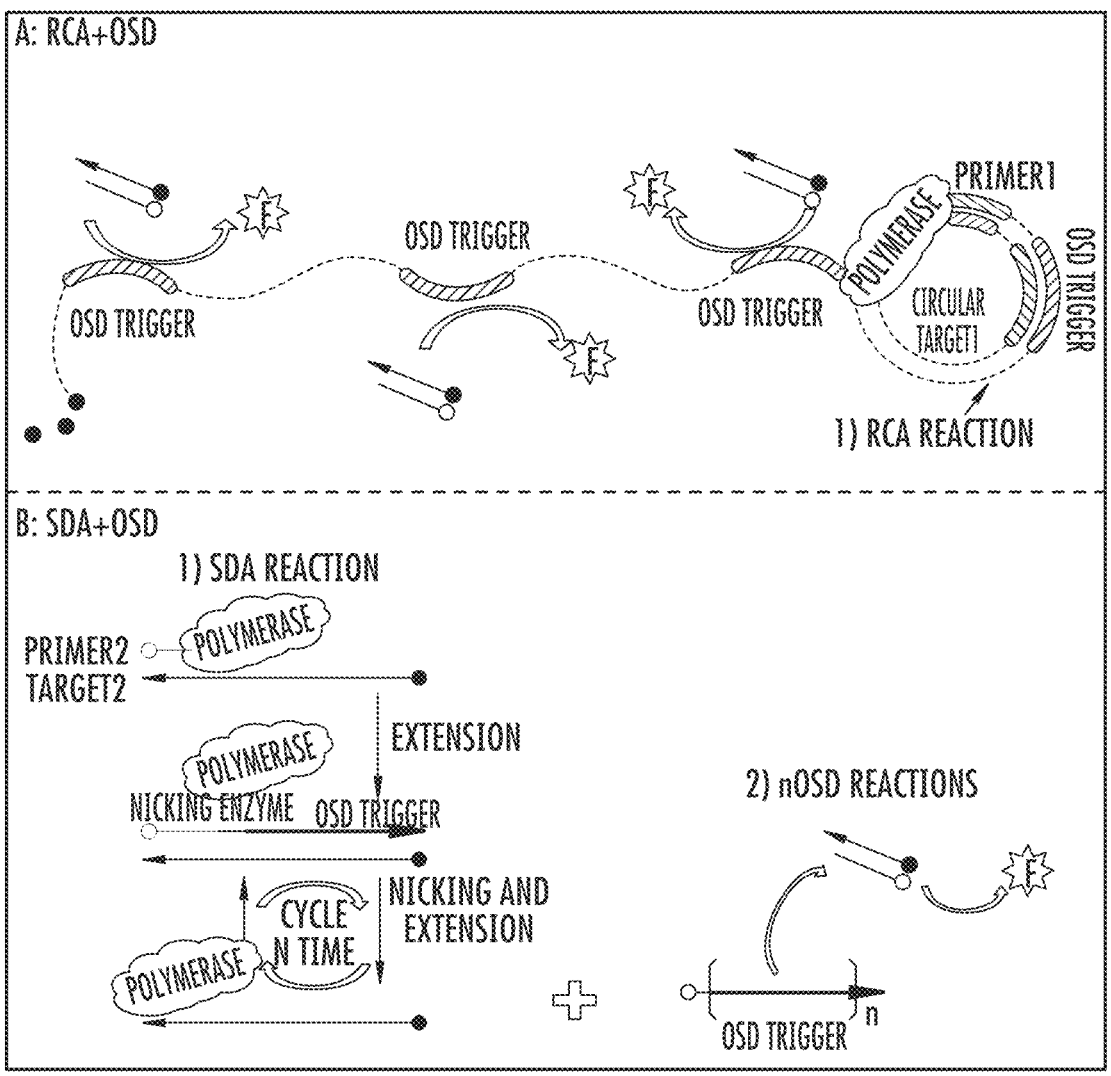

FIG. 10 shows OSD being used for transduction of nucleic acid signals into a fluorescent readout.

Figure 11:
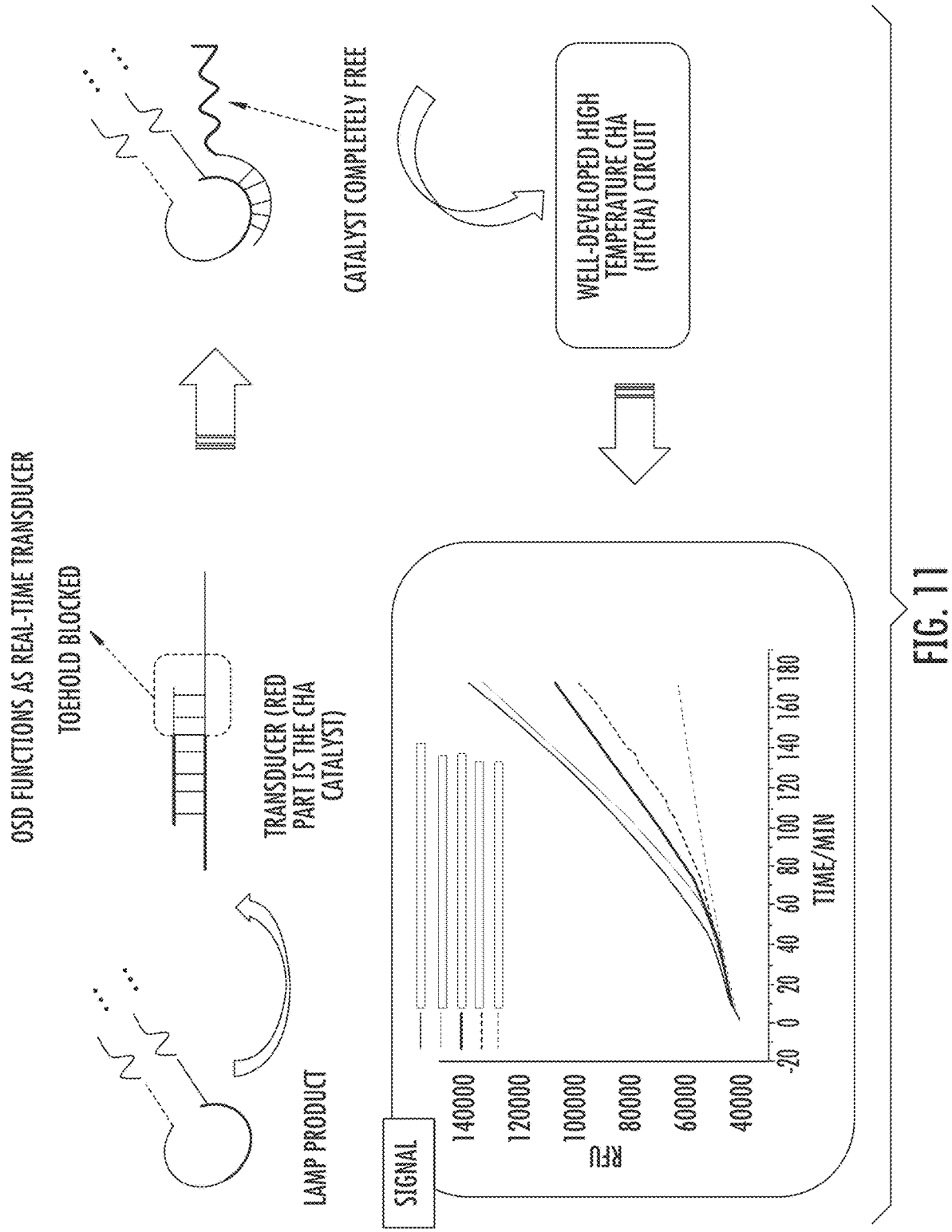

FIG. 11 shows that OSD functions as a real-time transducer. The transducer is a duplex with two regions: one that probes the LAMP product and the other that can trigger HTCHA, or another reaction which produces a signal. Before the LAMP reaction, the trigger's toehold is blocked and cannot react with CHA circuit; after the LAMP amplicons are generated, the blocker will be released and the trigger is free to induce the HTCHA reaction. With OSD transducer, any commonly used HTCHA set can be adapted to LAMP, irrespective of template and primer sequences.

Figure 12:
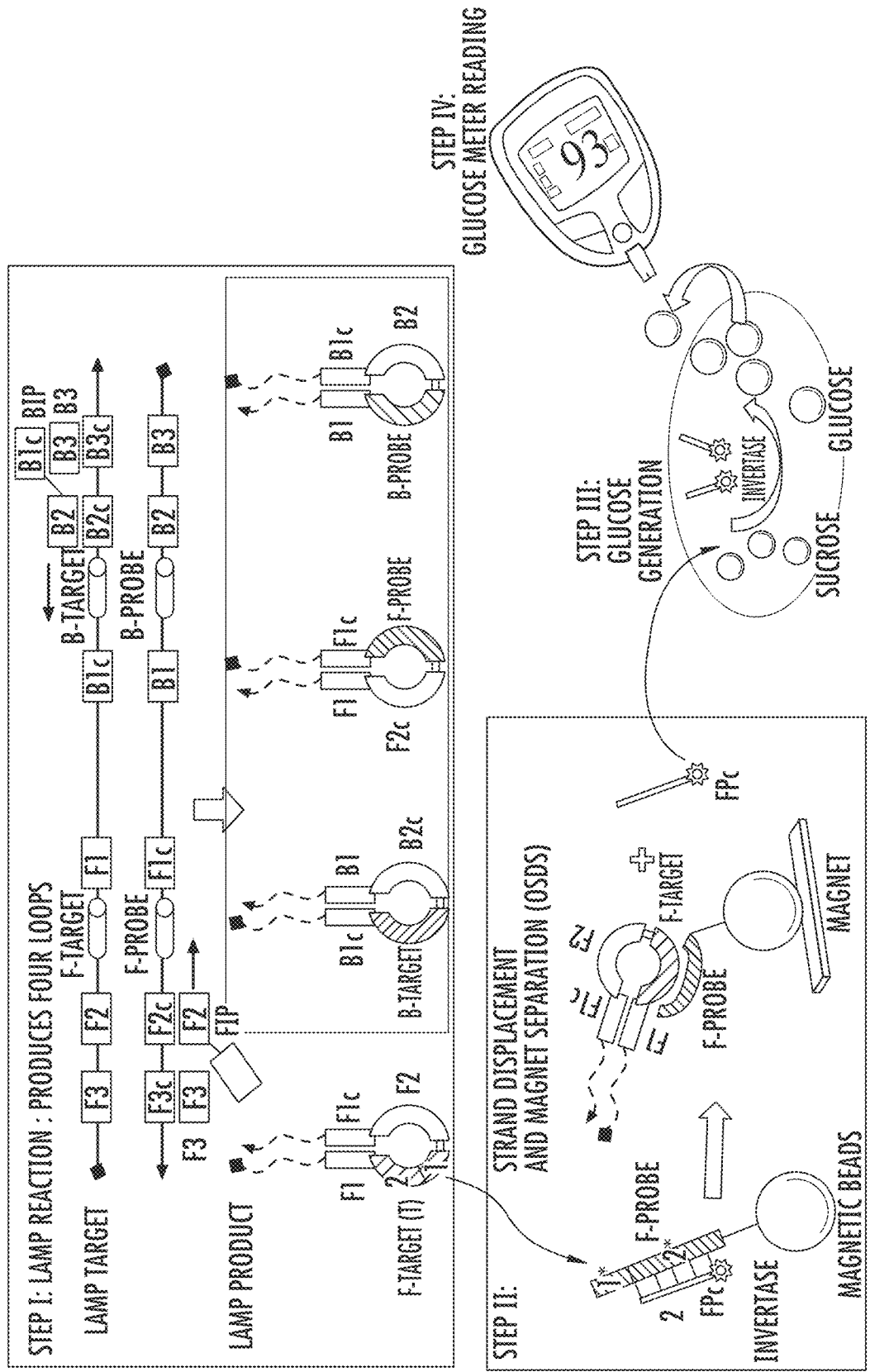

FIG. 12 shows a bead-based commercialized glucometer. The left scheme shows the concept of using OSD to transduce amplicons (e.g. from LAMP) to commercialized glucometers. Right figure: Final sensor responses to MERS-CoV RNA negative buffers (N-1, N-2) and 25 (P-1), 2.5E3 (P-2), 2.5E5 (P-3) PFU/mL MERS-CoV RNAs with 1.5 h LAMP reaction, respectively.

Figure 13:
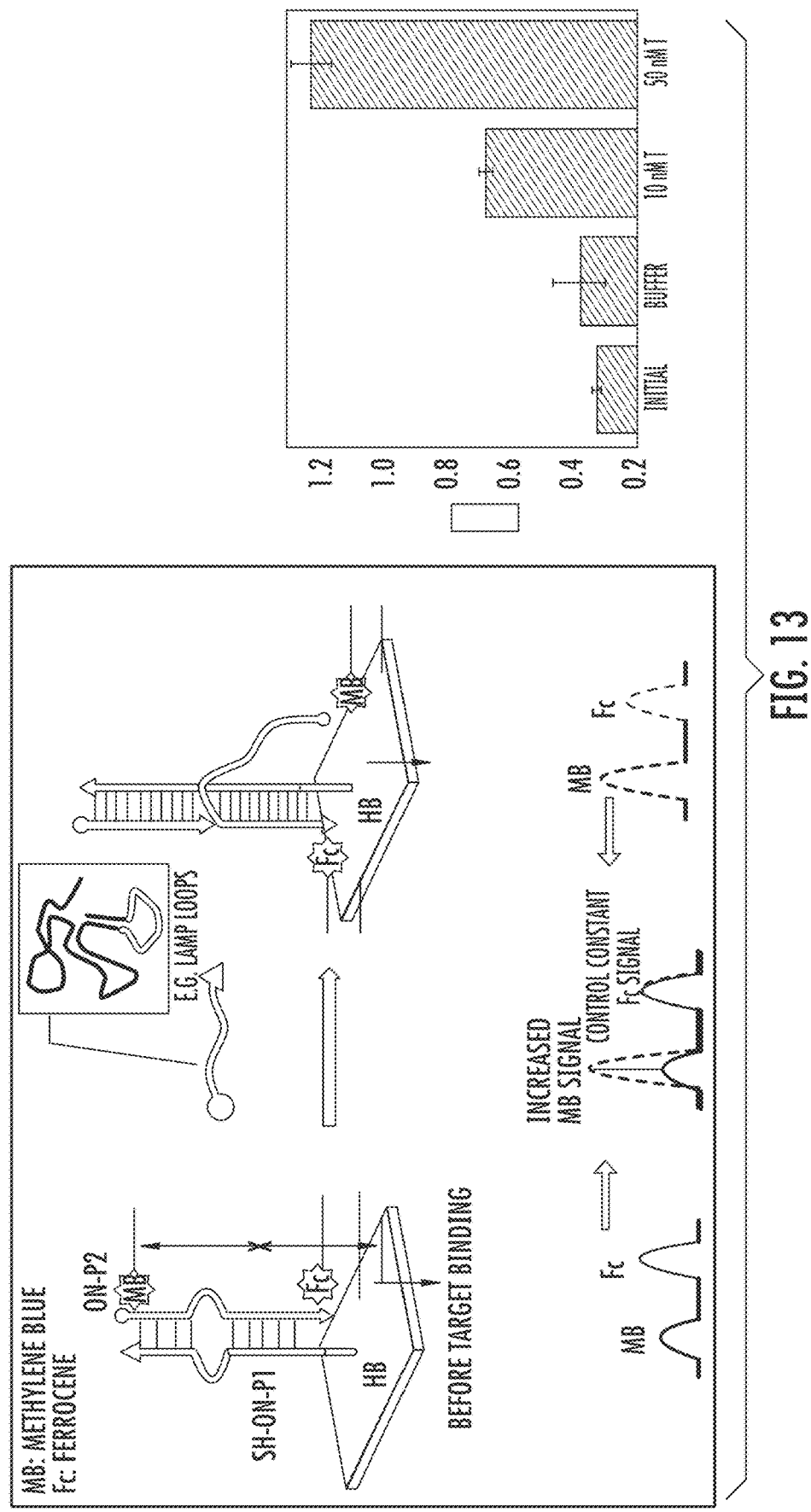

FIG. 13 shows surface-based ratio-metric electrochemical sensors used with OSD. The left scheme shows the concept of using OSD to transduce amplicons (e.g. from LAMP) to novel ratio-metric electrochemical platforms. The right figure shows the preliminary data for LAMP loop mimic sequence detection. "T" means the LAMP loop mimic sequence. "Initial" means background signal before "T" detection. The advantage of the ratiometric reading is high sensitivity, and that background variations induced by hard-repeating electrode surfaces are minimized.

Figure 14:
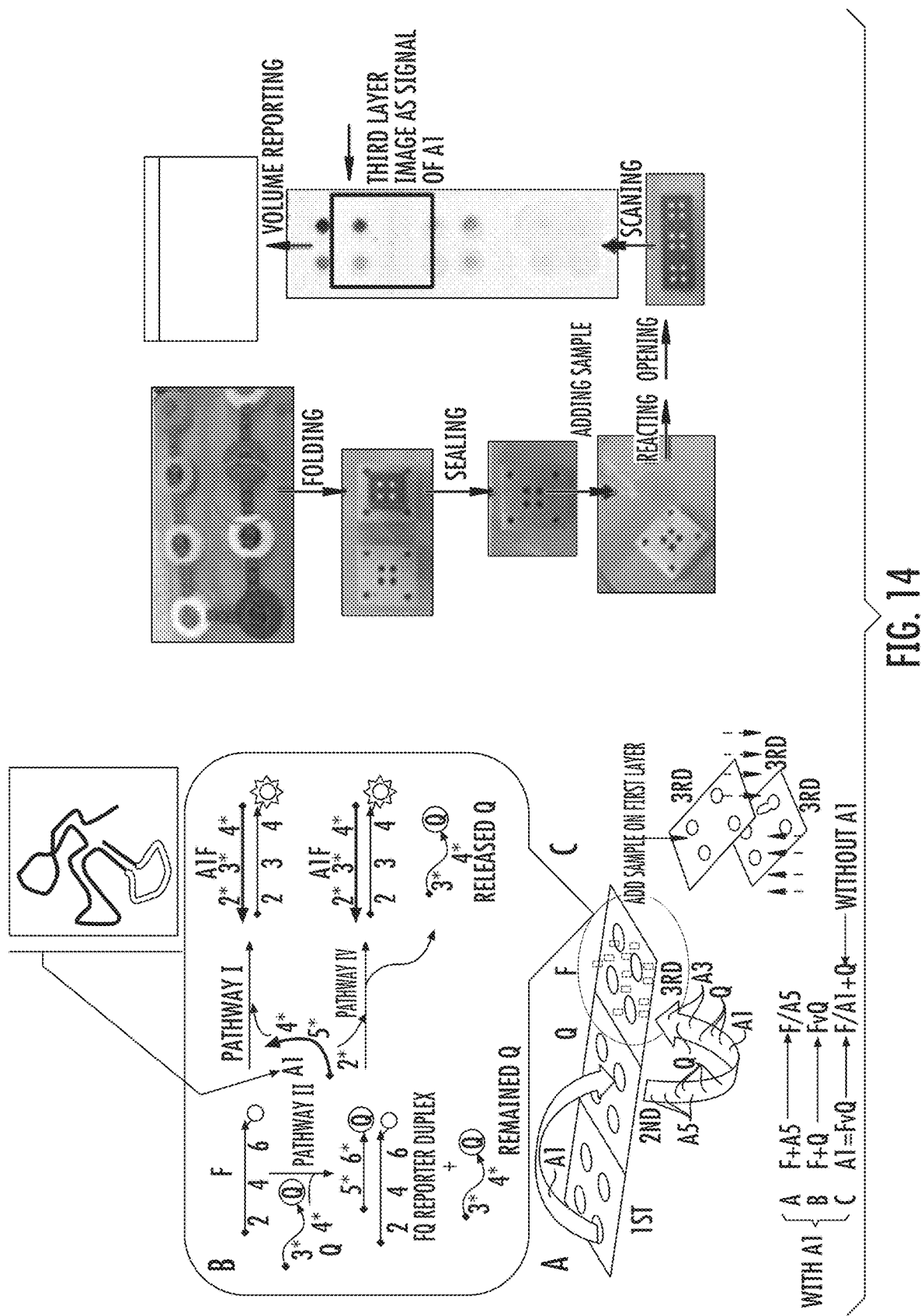

FIG. 14 shows a paper origami point-of-care fluorescence pad utilizing OSD. The left scheme shows the concept of using OSD to transduce amplicons (e.g. from LAMP) to paper point-of-care origami pad (Opad). Right figure shows the results for LAMP loop mimic sequence detection. "A1" means the LAMP loop mimic sequences.

Figure 15A:
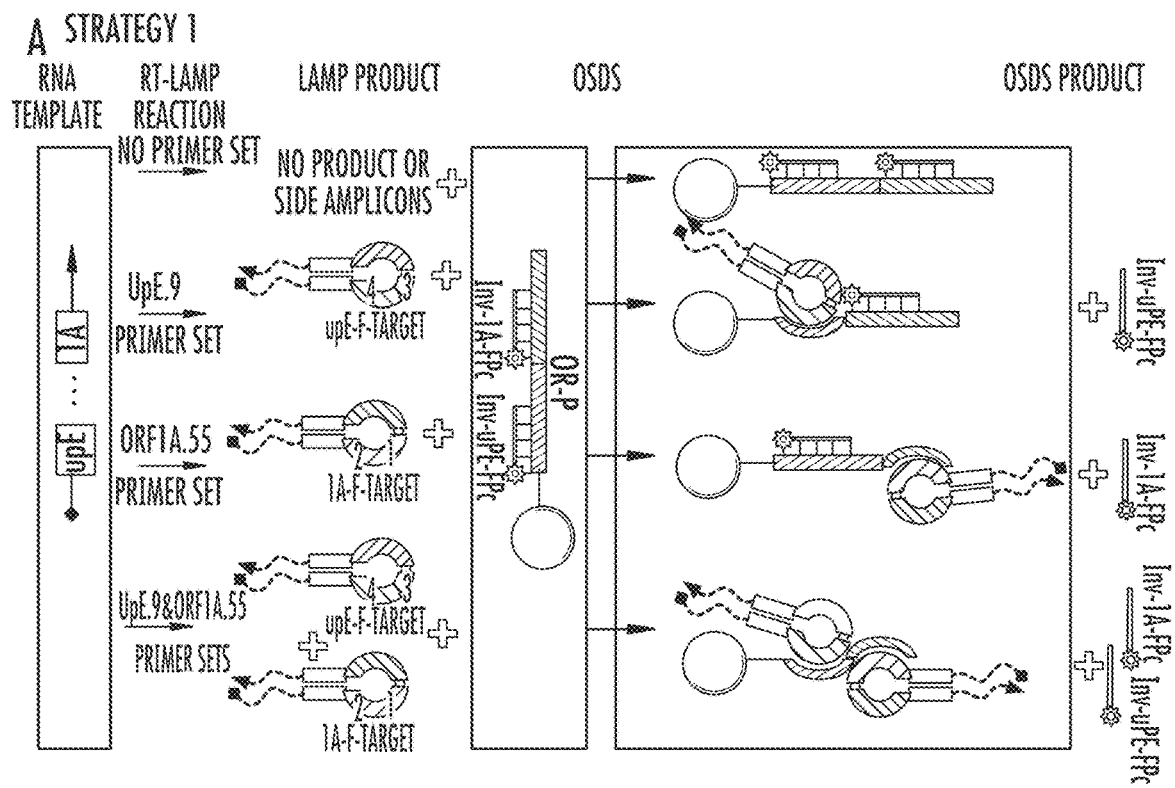
Figure 15B:
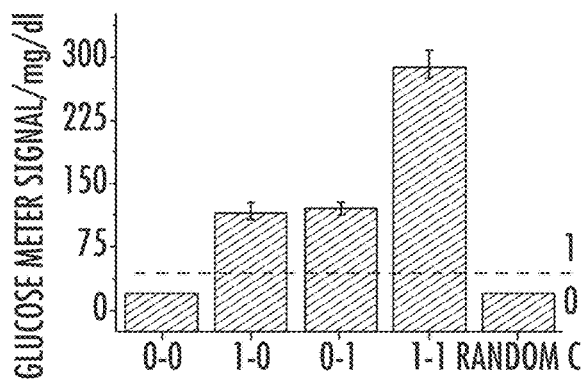
Figure 15C:
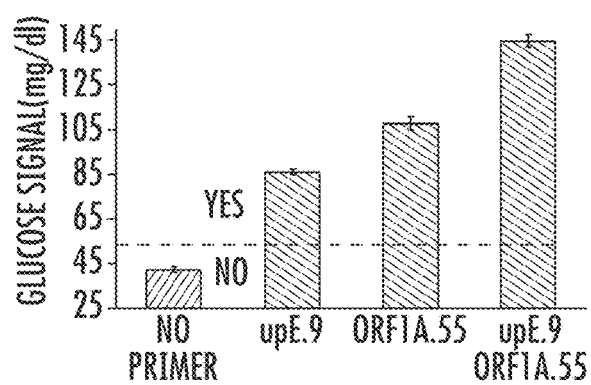

FIGS. 15A-C show the design of fail-safe OR GATE sensing platform. FIG. 15A shows a scheme of the OR gate design, probing either ORF1A region or upE region on MERS-CoV RNA. FIG. 15B shows an OR gate glucose meter signals gotten from directly using buffer, 500 nM upE-T, 500 nM 1A-T, and 500 nM upE-T&1A-T, as inputs to trigger OSDS and the following steps. FIG. 15C shows an OR gate LAMP-OSD-Glucometer responses to 2.5E5 PFU/mL MERS-CoV RNA with no primer, upE.9, ORF1A.55, and upE.9& ORF1A.55. Thermo-stable TmINV was used in these experiments, with 1.5 hour RT-LAMP (Step I), 1 hour 25° C. OSD, and 23 min glucose generation (Step III).

Figure 16:
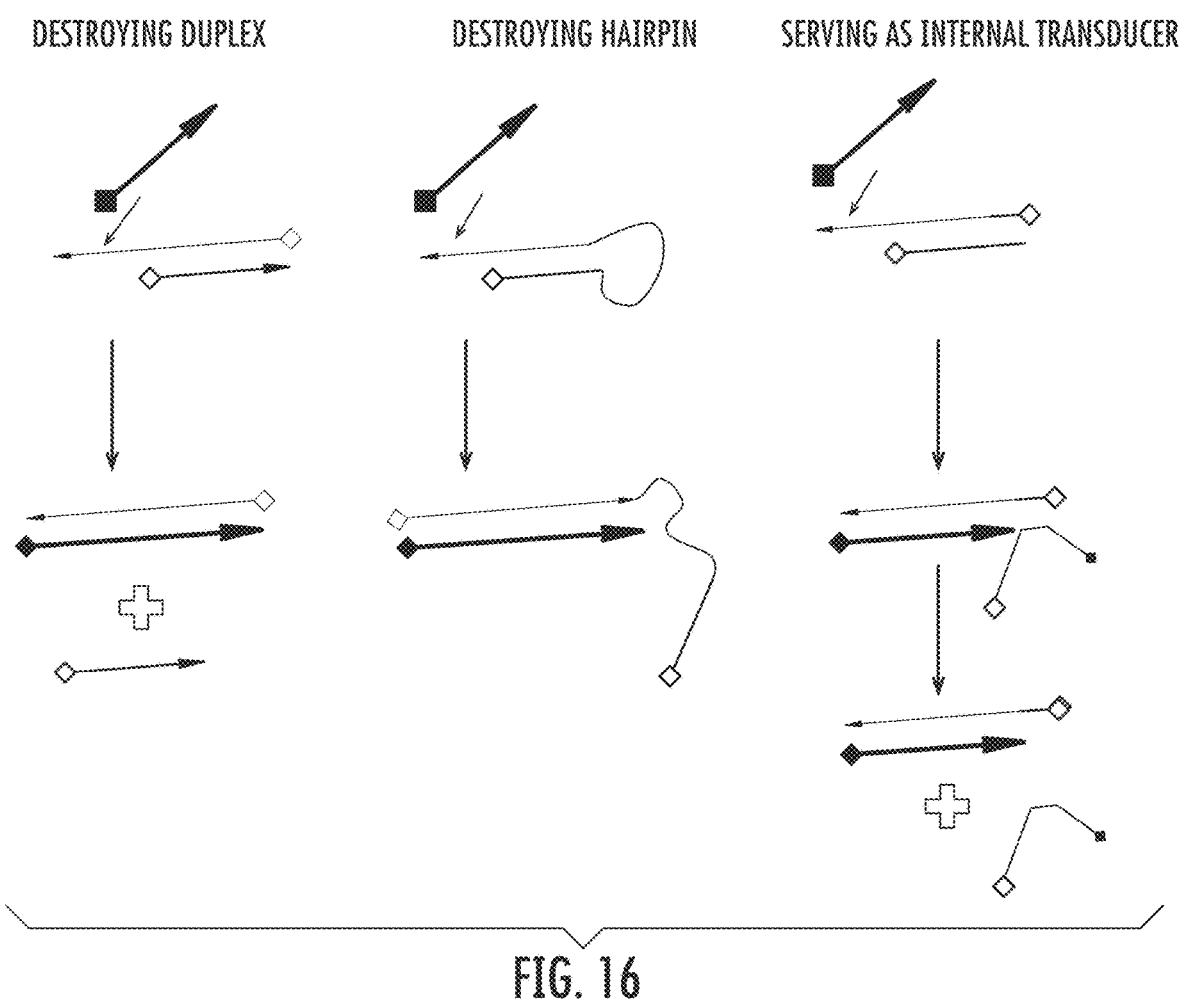

FIG. 16 shows that embodiments other than single-stranded nucleic acids hybridized to each other, such as hairpins, are possible with OSD.

Figure 17:
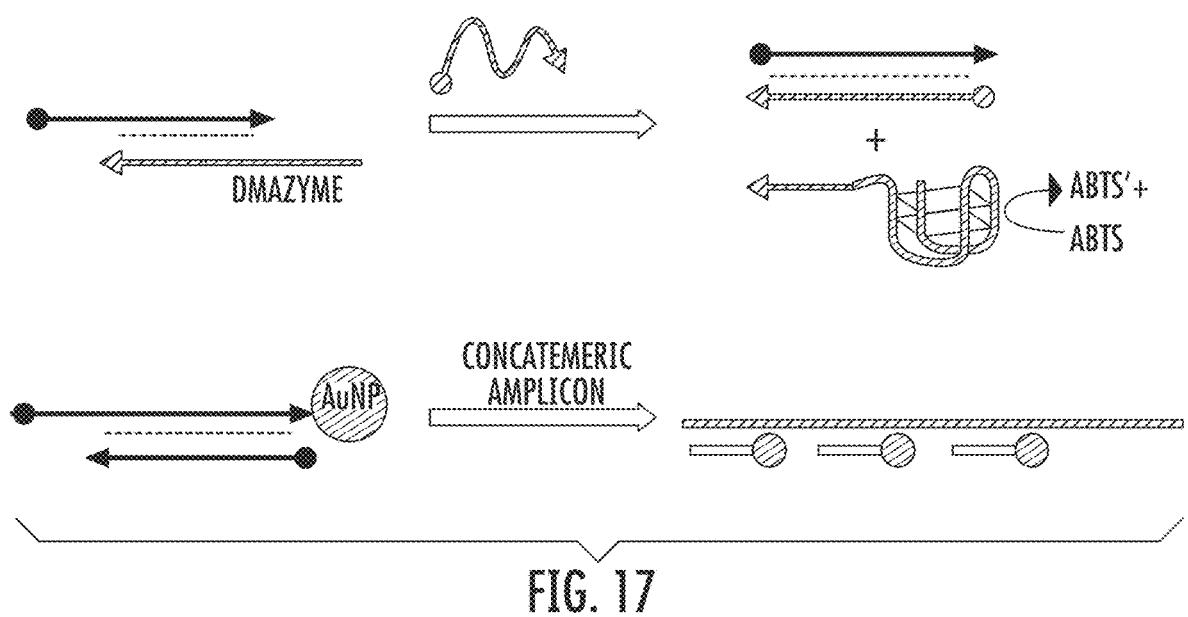

FIG. 17 shows a colorimetric detection scheme for use with OSD.

Figure 18:
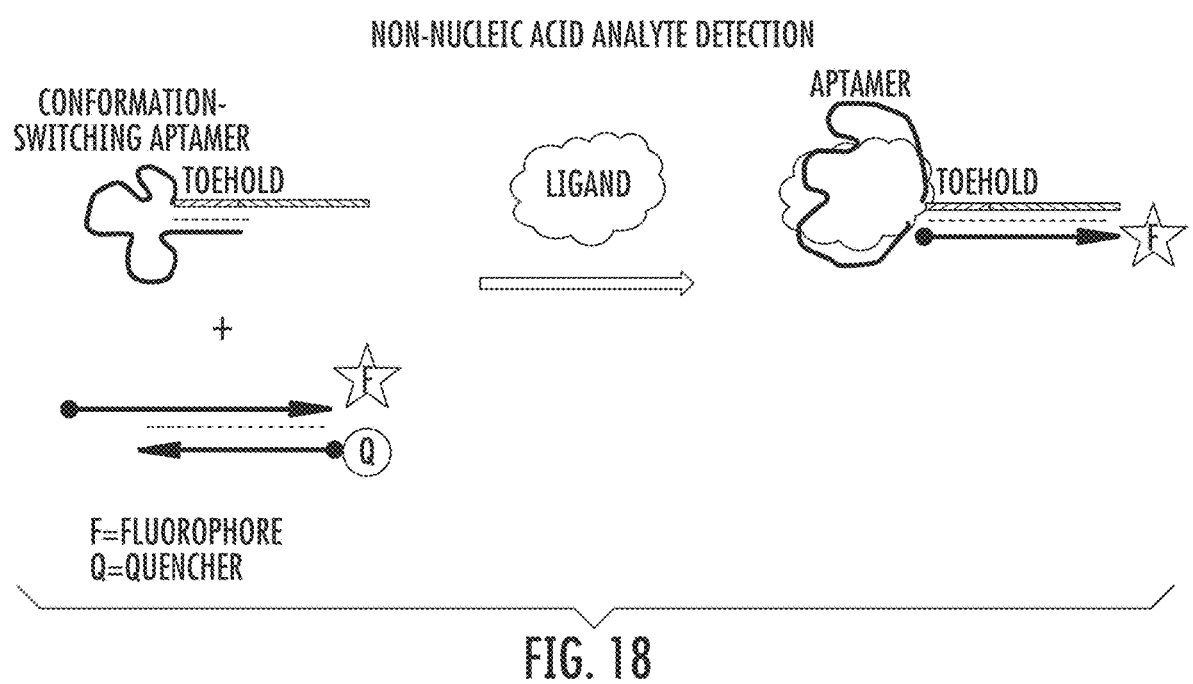

FIG. 18 shows that the OSD system can also be used with different analyte inputs other than nucleic acids.

Figure 19:
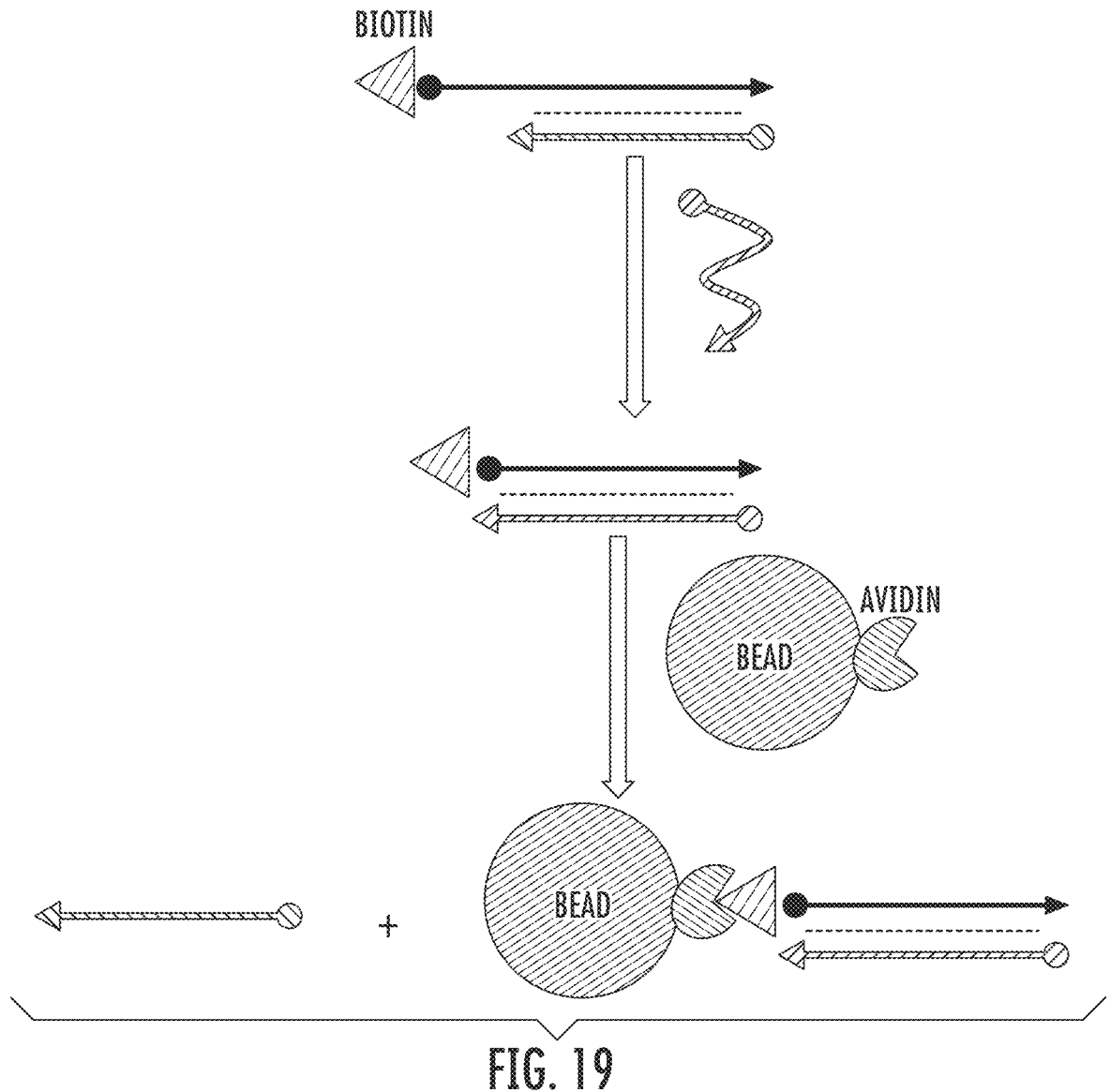

FIG. 19 shows avidin/biotin based separation of analyte and/or probe.

Figure 20:
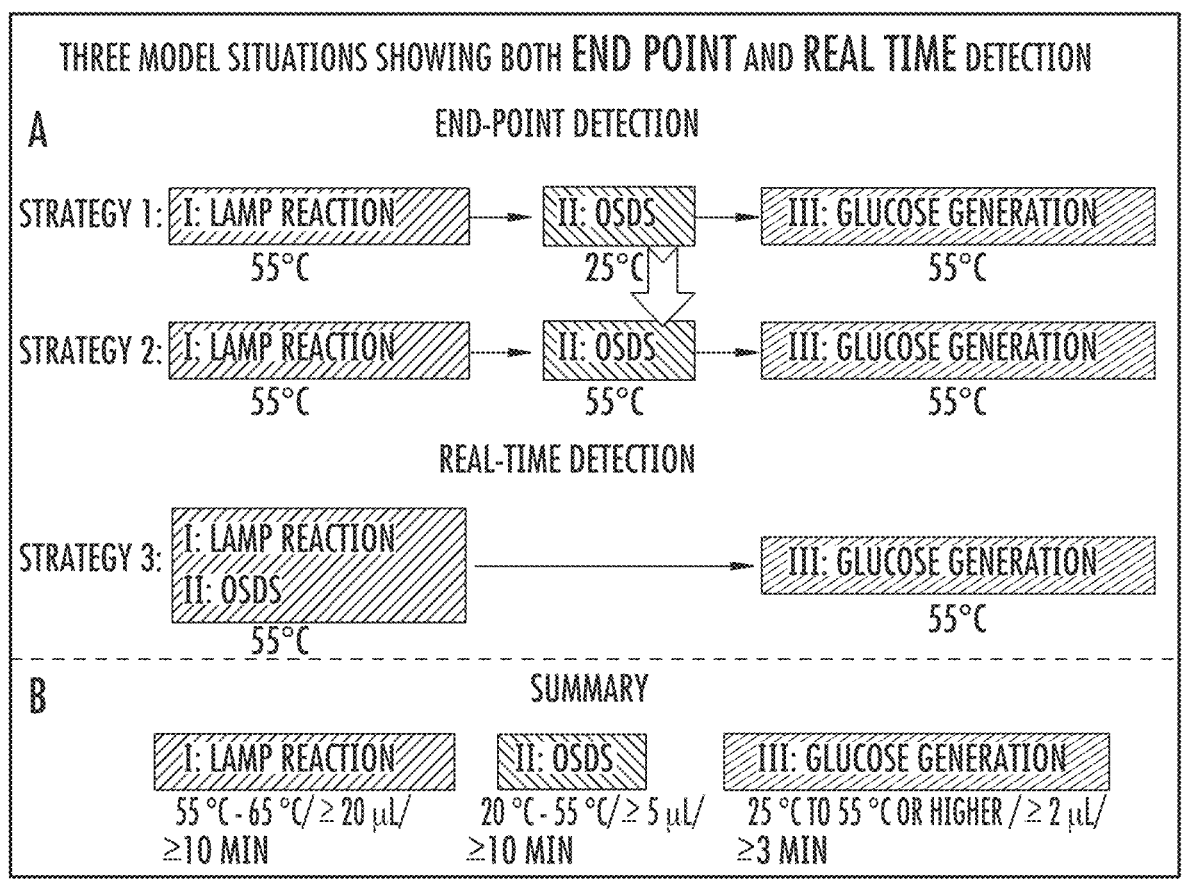

FIG. 20 shows three model strategies that proved the high robustness, flexibility, sensitivity and selectivity of the LAMP-OSD-Glucometer sensing platform.

Figures 21A, 21B:
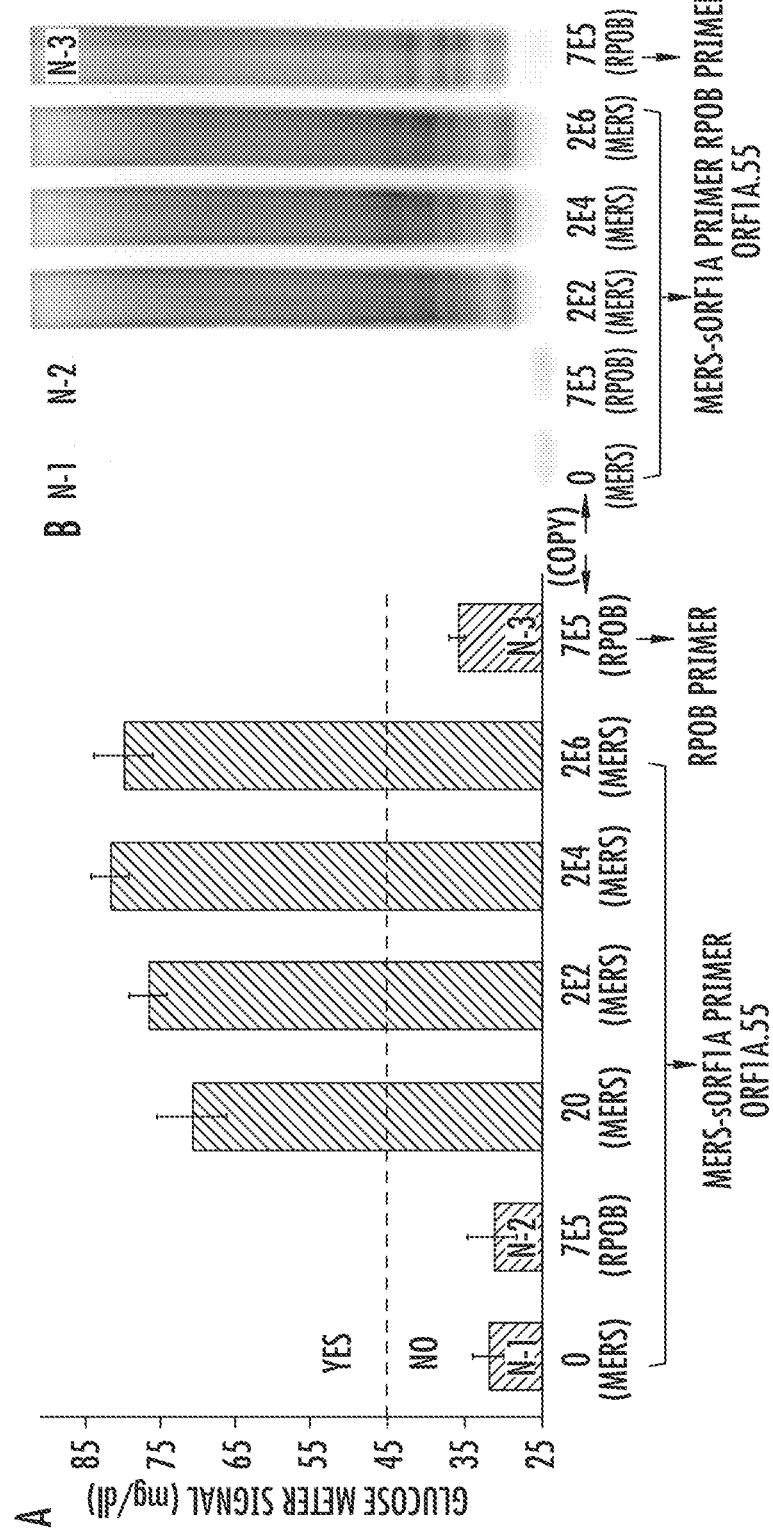

FIGS. 21A and B show the response of Strategy 1 for detecting the PCR product of segment MERS-sORF1A (sORF1A). (A) Final LAMP-OSD Glucometer responses to 7E5 copies of RPOB and different copies of MERS-sORF1A in presence of ORF1A.55 primer set or RPOB primer set. (B) Agarose electrophoresis characterization of LAMP products amplified from 7E5 copies of RPOB and different copies of sORF1A in presence of ORF1A.55 primer set or RPOB primer set. Commercially available yeast invertase was used in these experiments, with 1.5 hour or 10 min RT-LAMP (Step I), 1 hour OSD, and 40 min glucose generation (Step III).

Figures 22A, 22B:
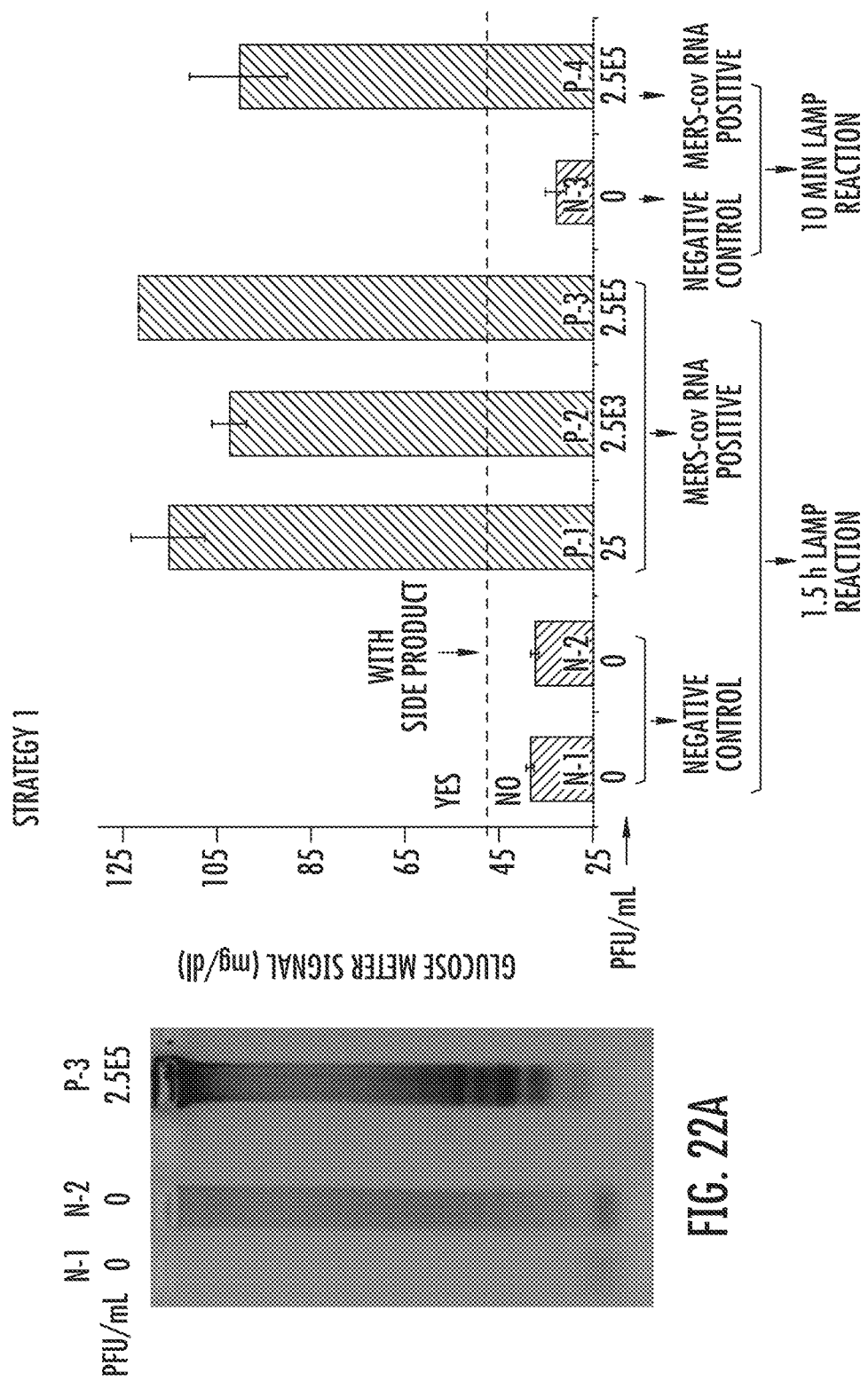

FIGS. 22A and B show reverse transcription LAMP-OSD-Glucometer Platform response of Strategy 1 to RNA extracted from tissue culture grown MERS-CoV virions. (A) Agarose electrophoresis characterization of RT-LAMP amplified from MERS-CoV RNA negative buffers (N-1 and N-2) and 2.5E5 PFU/mL MERS-CoV RNAs (P-3). (B) Final LAMP-OSD-Glucometer Platform responses to MERS-CoV RNA negative buffers (N-1, N-2, and N-3) and 25 (P-1), 2.5E3 (P-2), 2.5E5 (P-3 and P-4) PFU/mL MERS-CoV RNAs with 1.5 h or 10 min LAMP reaction, respectively. The signals of N-1, N-2 and P-3 in FIG. 22B were gotten from the same RT-LAMP products as the N-1, N-2, and P-3 shown in FIG. 4A, respectively. Thermo-stable TmINV was used in these experiments, with 1.5 hour or 10 min RT-LAMP (Step I), 1 hour 25° C. OSD, and 23 min glucose generation (Step III).

Figures 23A, 23B:
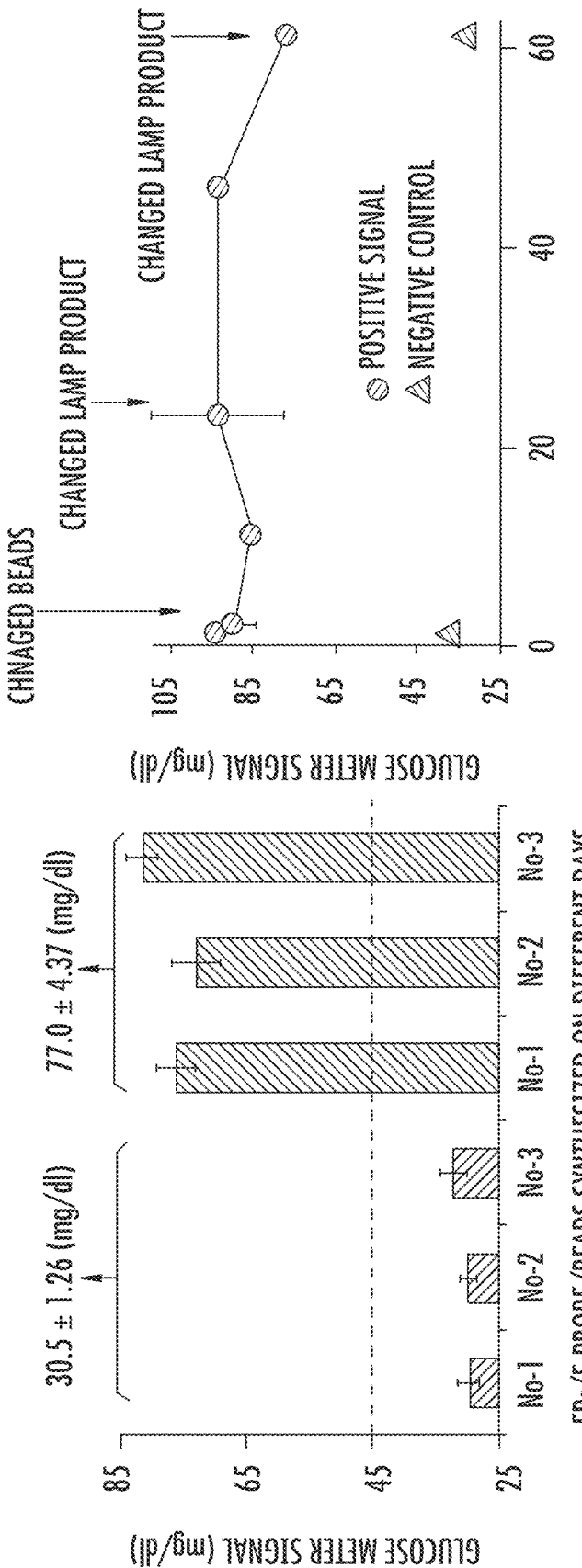

FIGS. 23A and B show reproducibility (A) and stability (B) tests (Strategy 1) of Inv-FPc/FP modified magnetic beads. (A) LAMP-OSD-Glucometer Platform responses to buffer control (No-1, No-2, and No-3) and 2E4 copies of sORF1A (No-1, No-2, and No-3) using Inv-FPc/FP/MBs conjugated on three different days. On each day, three parallel assays were carried out for both buffer control and 2E4 copies of sORF1A. Therefore in total nine assays were carried out for both buffer control and 2E4 copies of sORF1A. "No-1, No-2 and No-3" represented samples prepared in three different days. (B) Time dependence LAMP-OSD-Glucometer Platform responses of 2E4 copies sORF1A samples with the same Inv-FPc/FP/MB s. Thermo-stable TmINV was used in these experiments, with 1.5 hour LAMP (Step I), 1 hour 25° C. OSD, and 23 min glucose generation (Step III).

Figure 24:
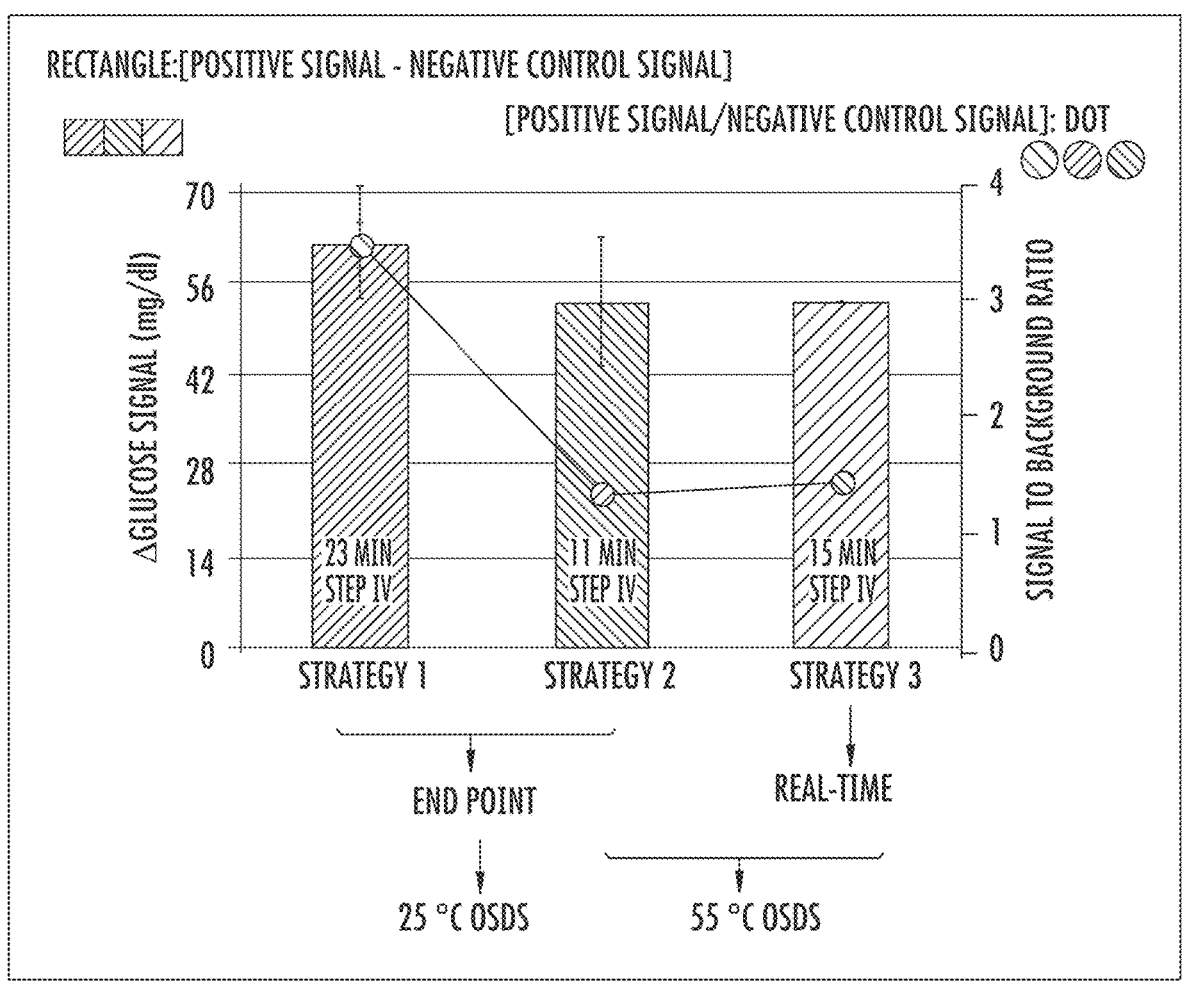

FIG. 24 shows signal amplitude (AGlucose signal, rectangles, left y-axis) and Signal-to-background ratio (dots, right y-axis) of 2.5E5 PFU/mL MERS-CoV RNA gotten from the three strategies shown in FIG. 21. Thermo-stable TmINV was used in these experiments, with 1.5 hour RT-LAMP (Step I).

Figure 25:
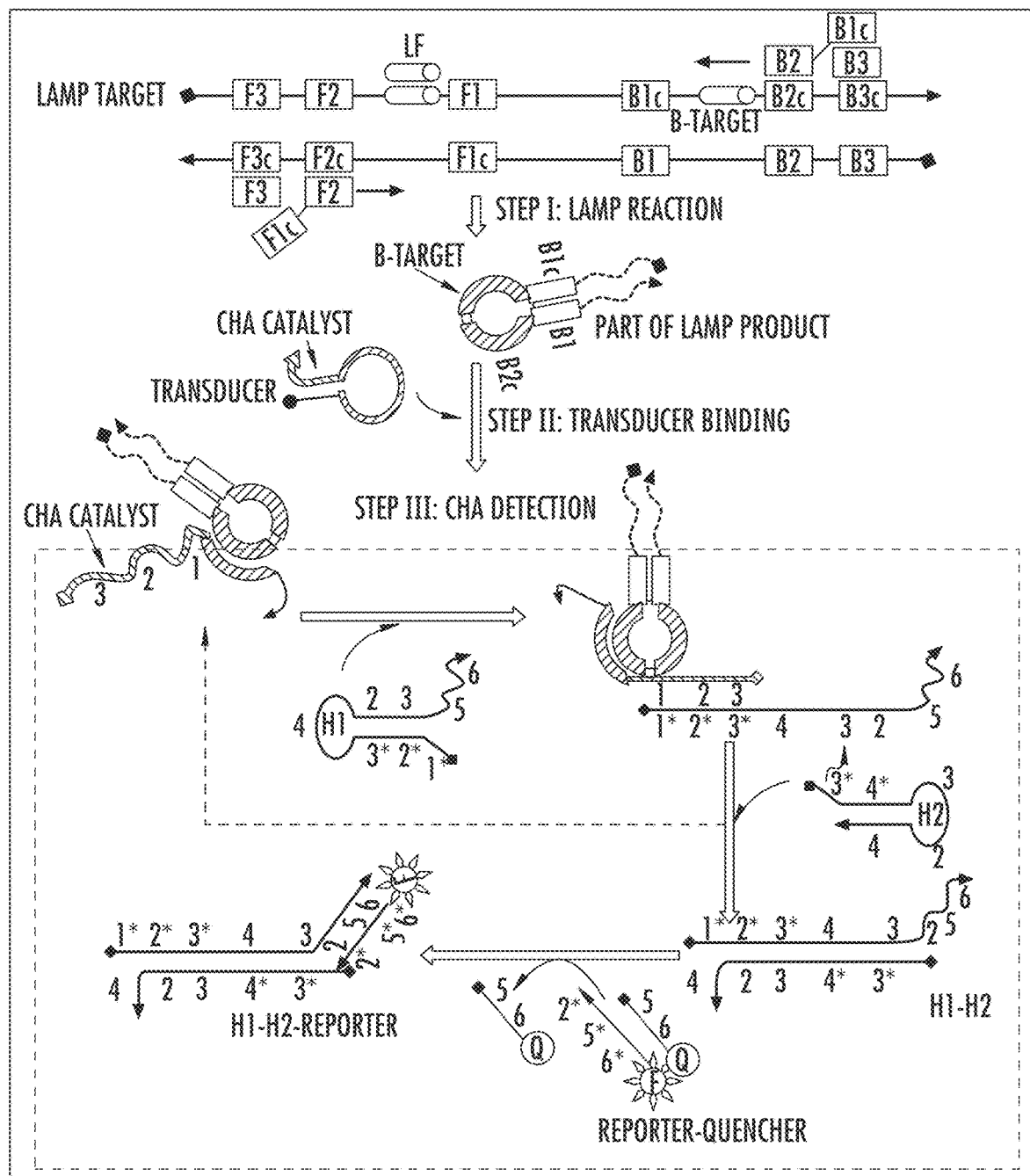

FIG. 25 shows a schematic of a two-step analysis using LAMP and CHA together.

Figure 26:
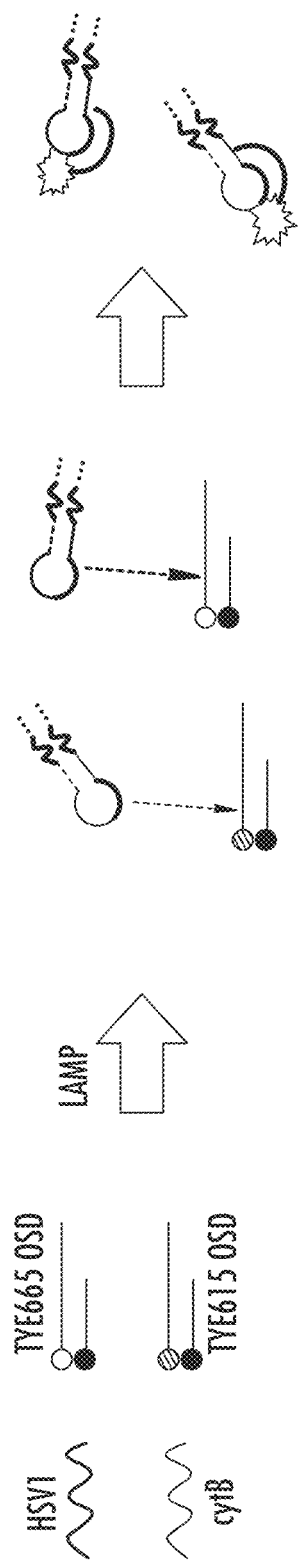
Figure 26:
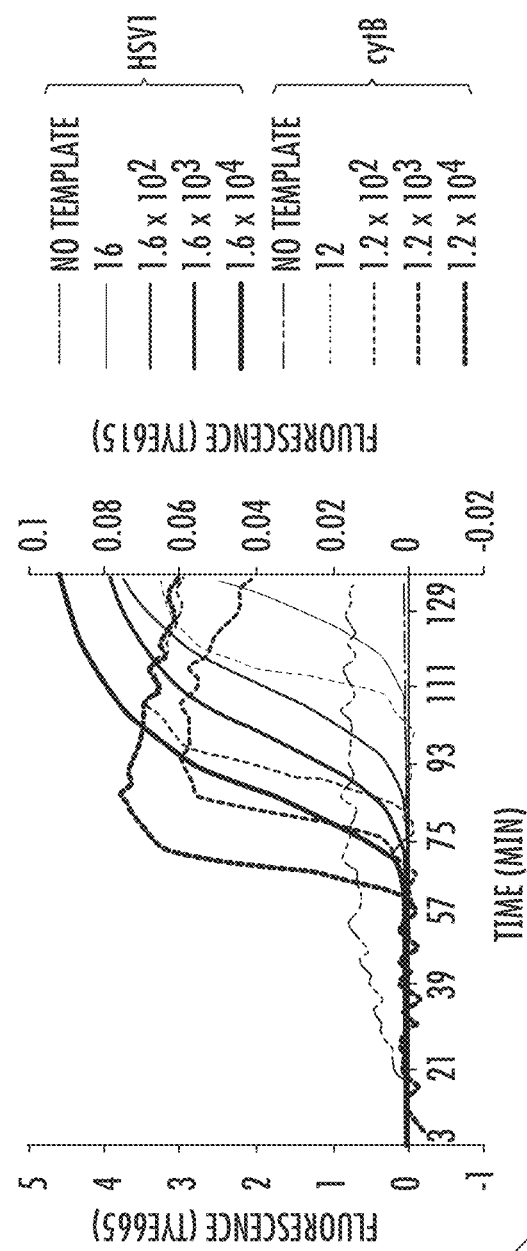

FIG. 26 shows multiple target analysis with two OSD reporters.

Figure 27:
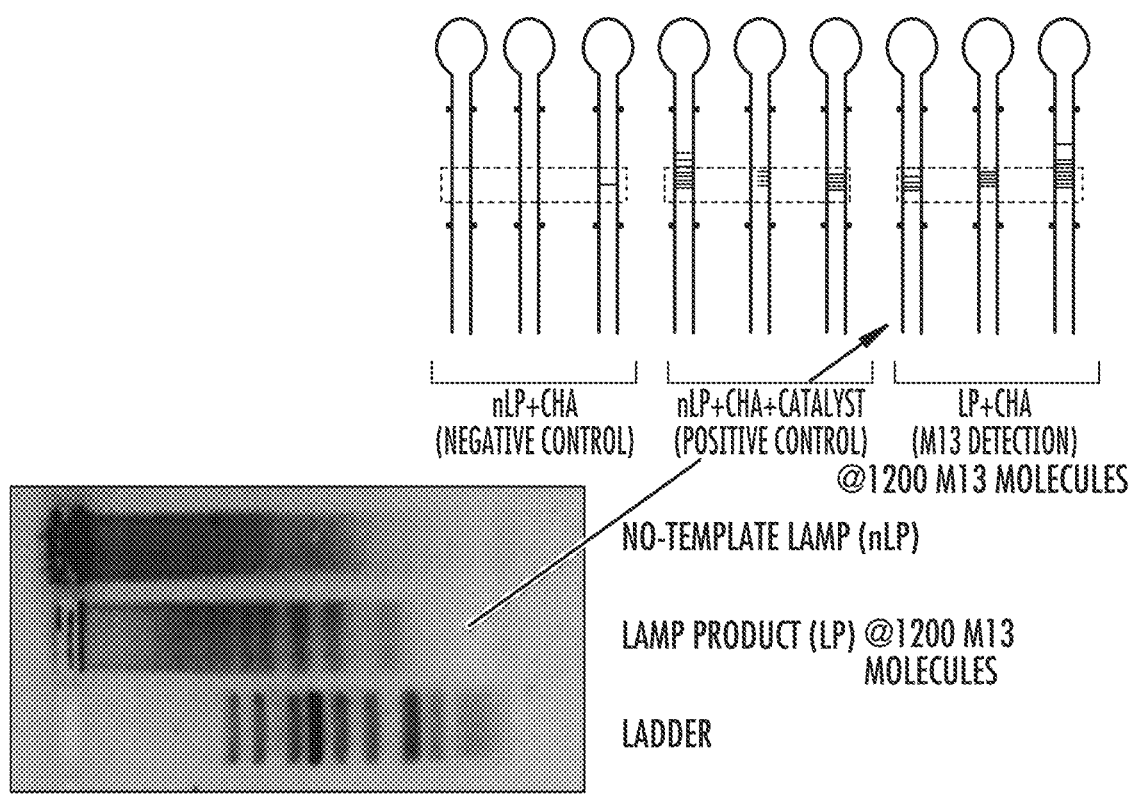

FIG. 27 shows strand exchange reactions can be adapted to end-point detection on paperfluidics platforms. As with fluorescence detection, the background is suppressed, and the real amplicons are transformed into signal.

Figure 28:
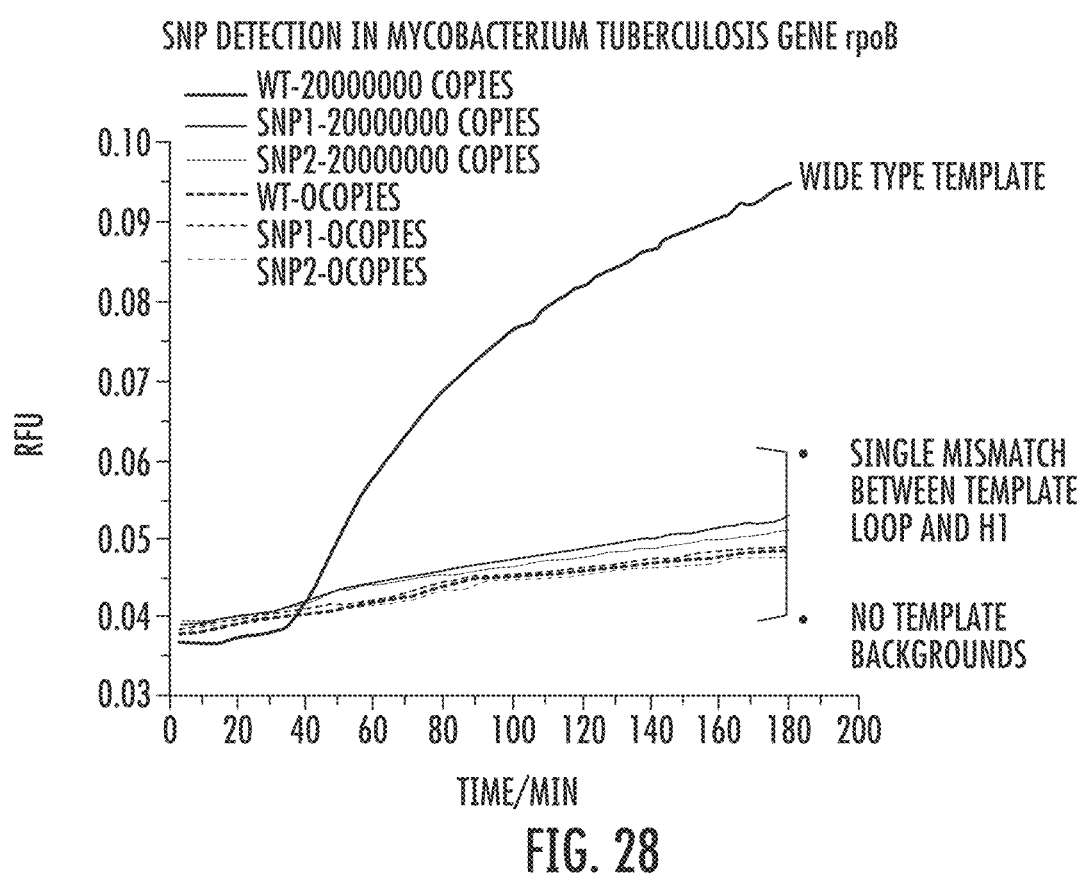

FIG. 28 shows real-time LAMP has great mismatchdetection.

Figure 29:
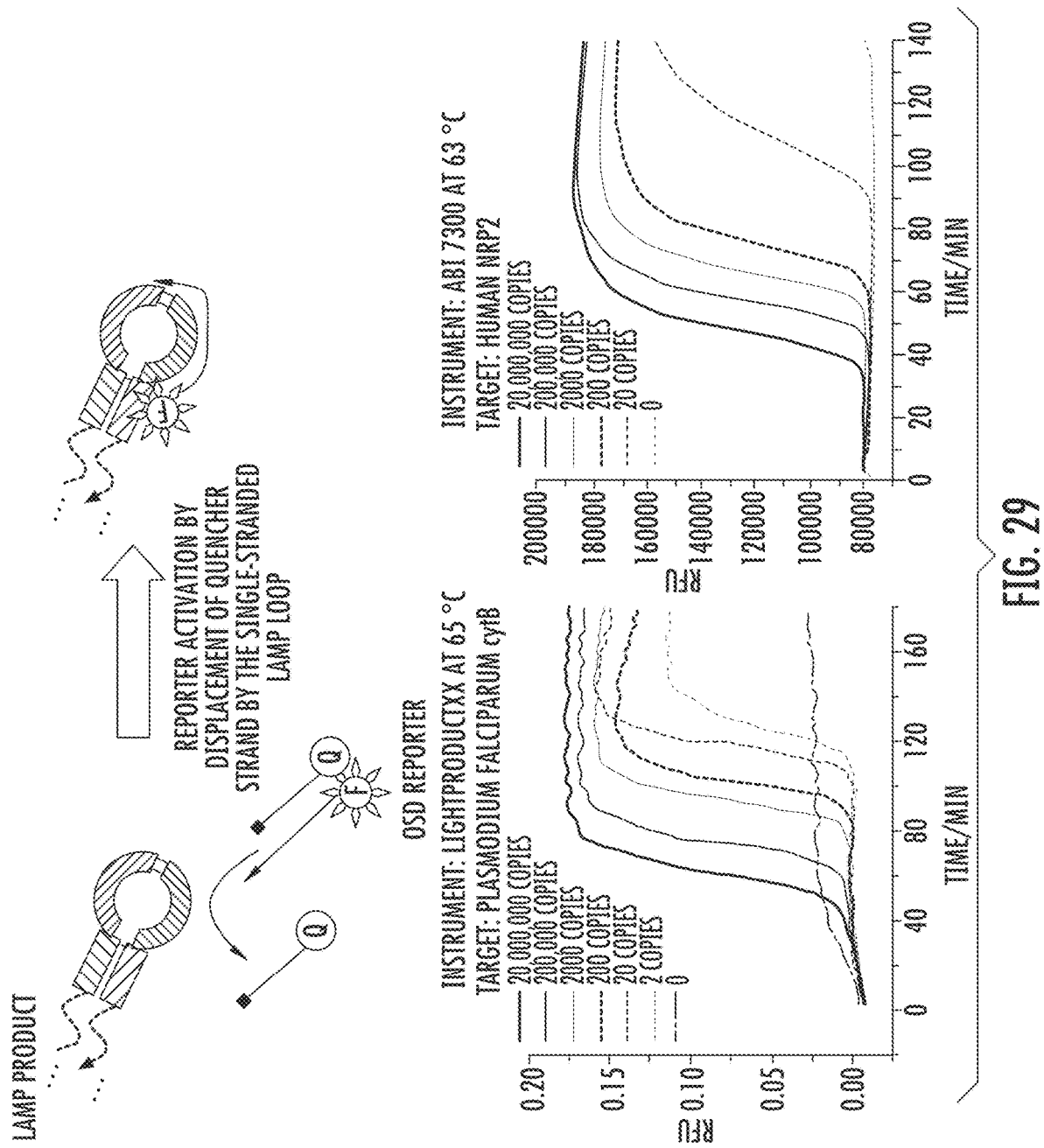

FIG. 29 shows real-time LAMP detection with one-step displacement (OSD) probes.

Figure 30:
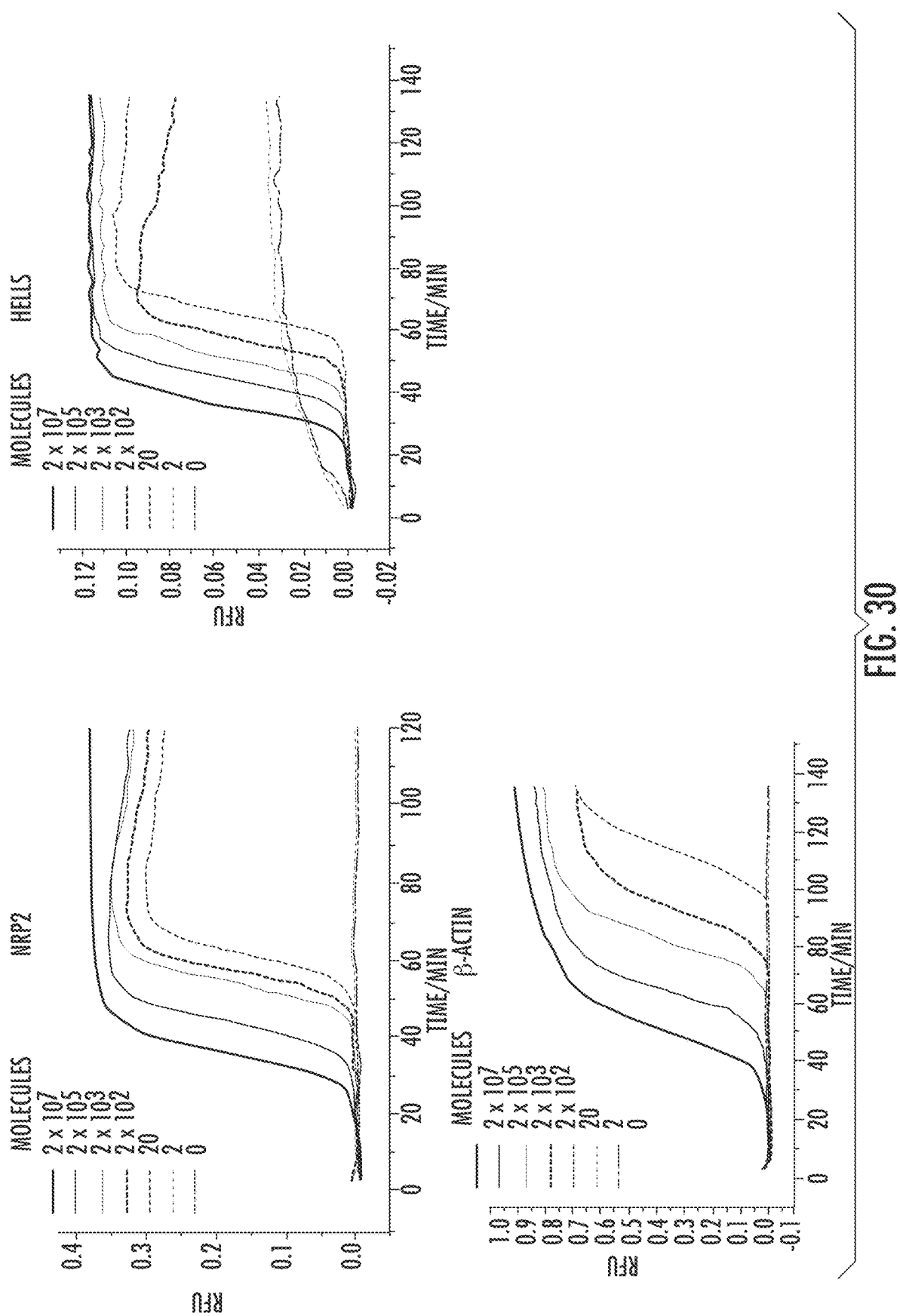

FIG. 30 shows real-time sequence-specific detection of LAMP amplicons using one-step strand displacement probes. The control gene β-actin and the melanoma-associated LAMP amplicons of NRP2 and HELLS could be detected with a LOD of 20 molecules.

Figure 31:
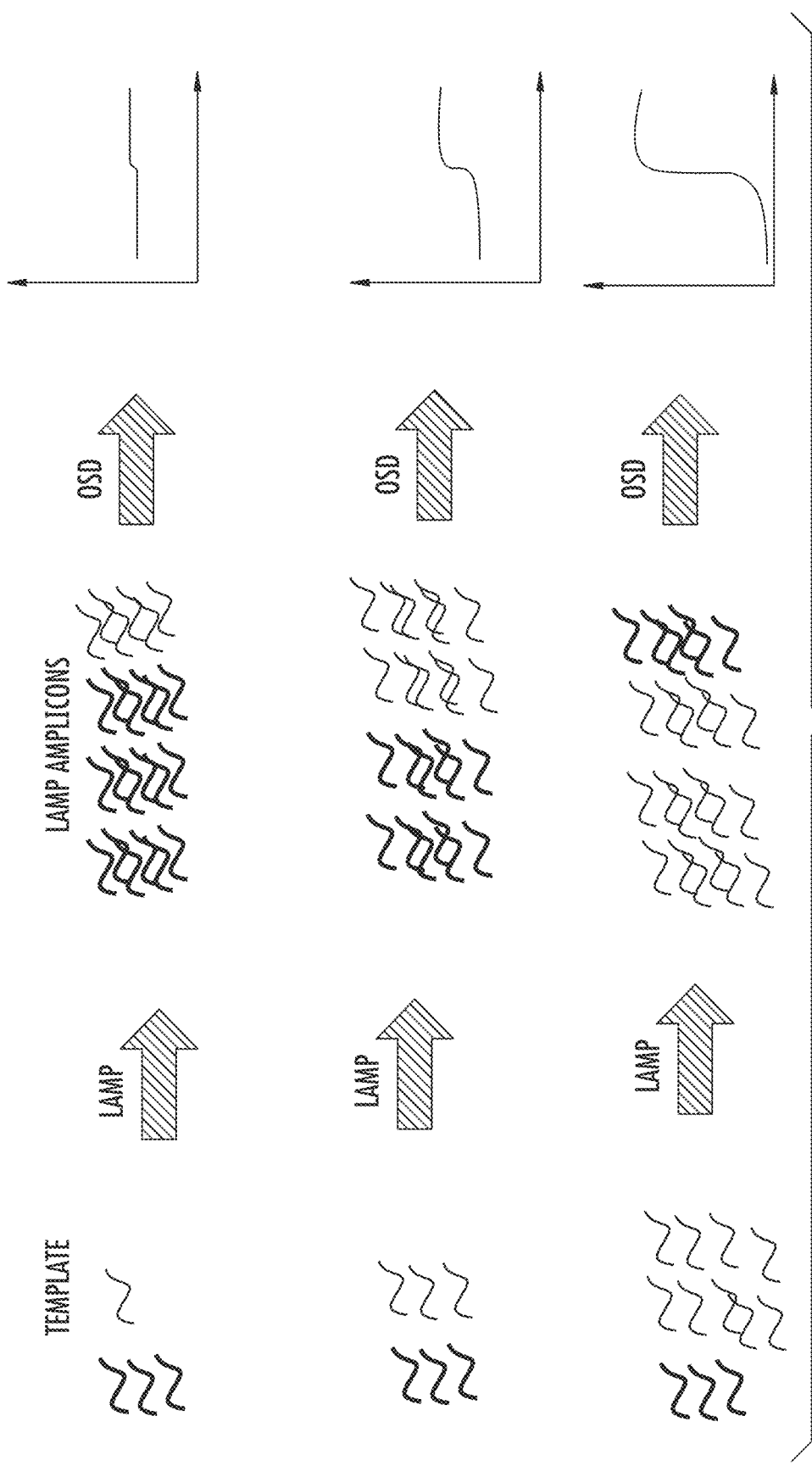

FIG. 31 shows a schematic for using false target to set up a threshold. The amplicon amount is determined by primer amount, which is independent of template amount.

Figure 32:
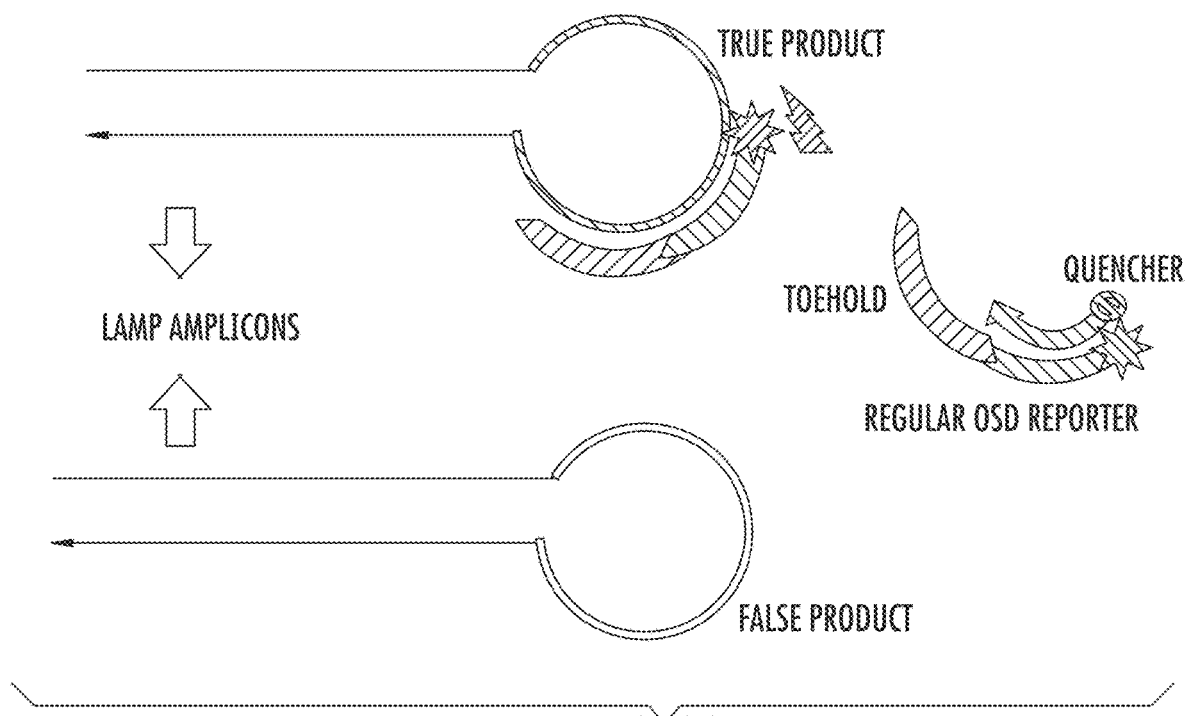

FIG. 32 shows how to make false target: keep the primer region and scramble the loop sequence (OSD probing loop). The OSD probe is very sequence specific, so it only responds to correct amplicons.

Figure 33:
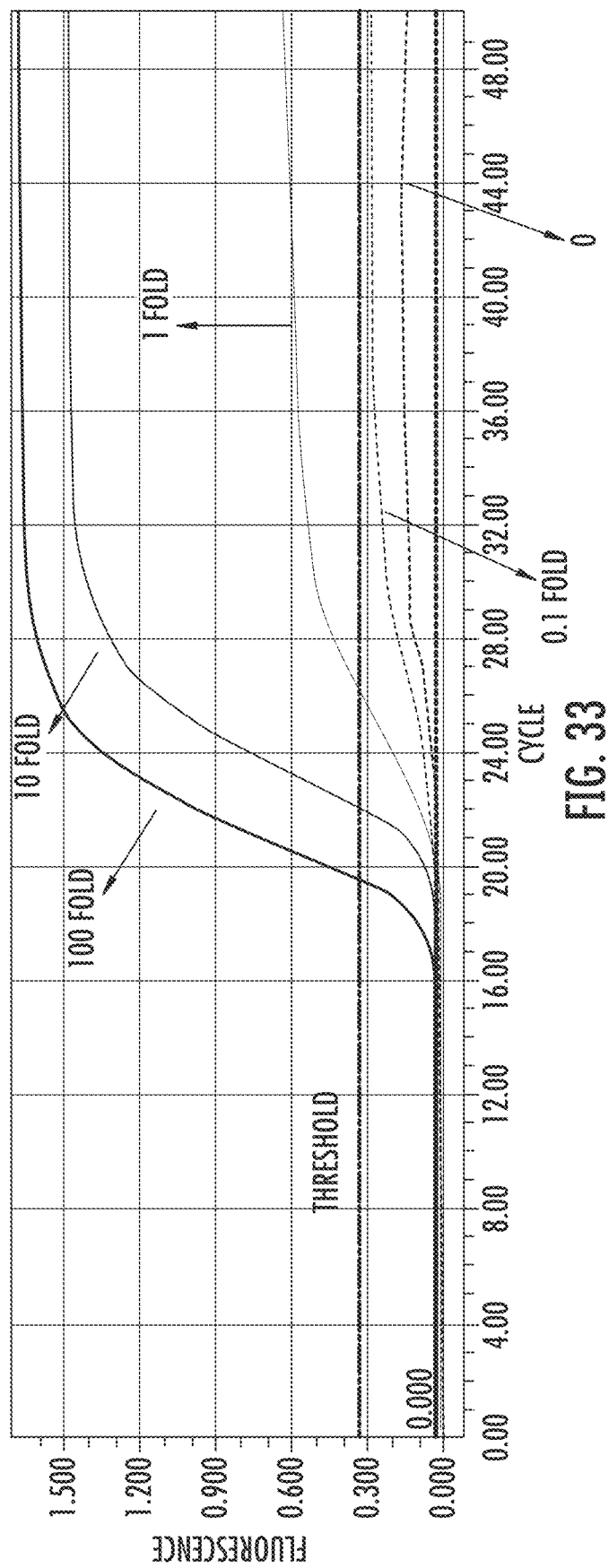
Figure 34:
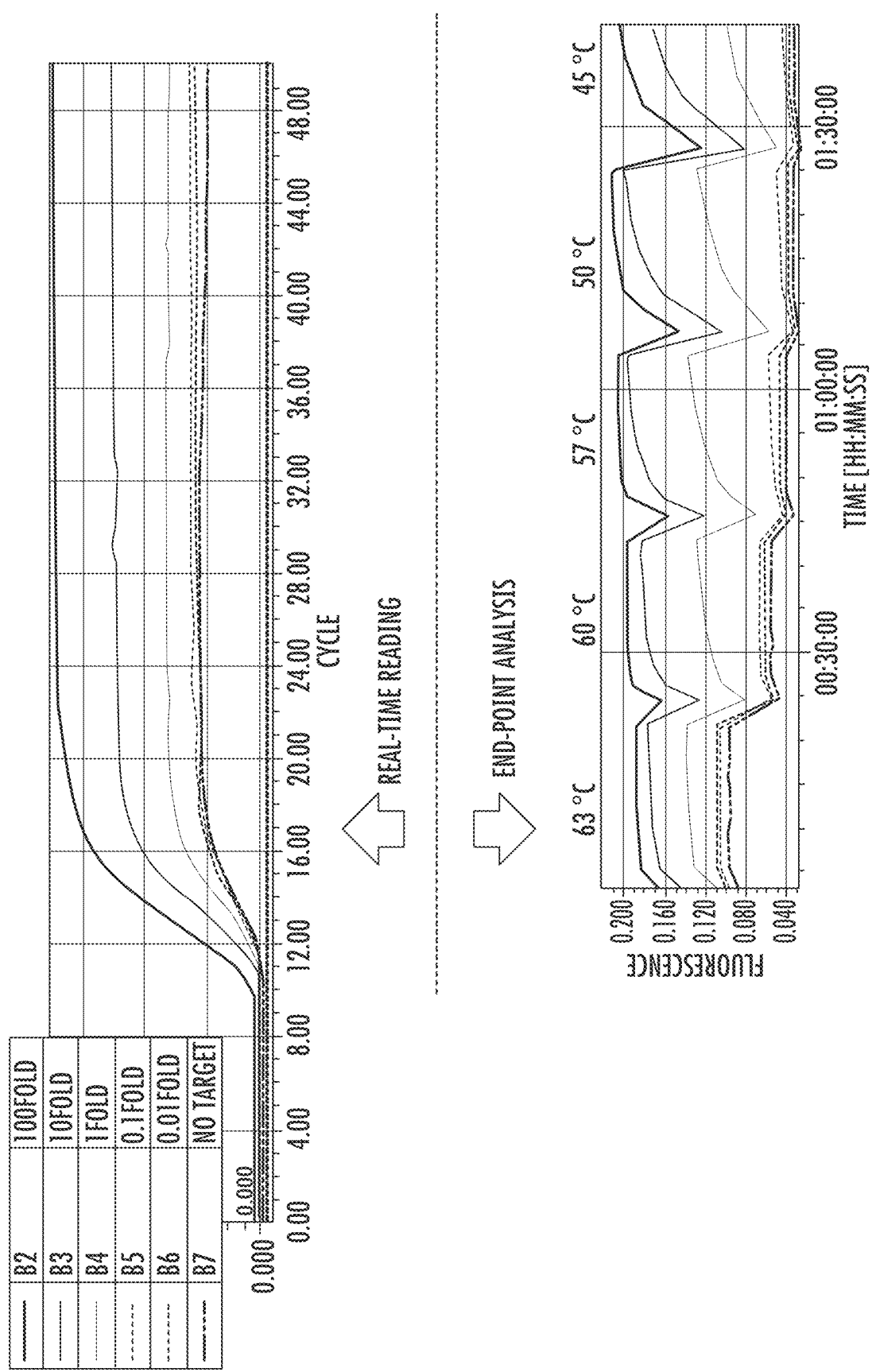

FIG. 33 shows LAMP-OSD for BRAF detection with false target at 60° C. Template: wild-type BRAF gene False target: the F loop region of the wild-type BRAF gene was randomized and a new plasmid was made. 100 fold: 1 ng True template+10 pg False target. 10 fold: 100 pg True template+10 pg False target. 1 fold: 10 pg True template+10 pg False target. 0.1 fold: 1 pg True template+10 pg False target. 0: no True template+10 pg False target FIG. 34 shows LAMP-OSD for NRP2 detection at 63° C. and end point fluorescence analysis at different temperatures. 100 fold: ing True+10 pg False target, 10 fold: 100 pg True+10 pg False target. 1 fold: 10 pg True+10 pg False target. 0.1 fold: 1 pg True+10 pg False target. 0: no True template+10 pg False target.

Figure 35:
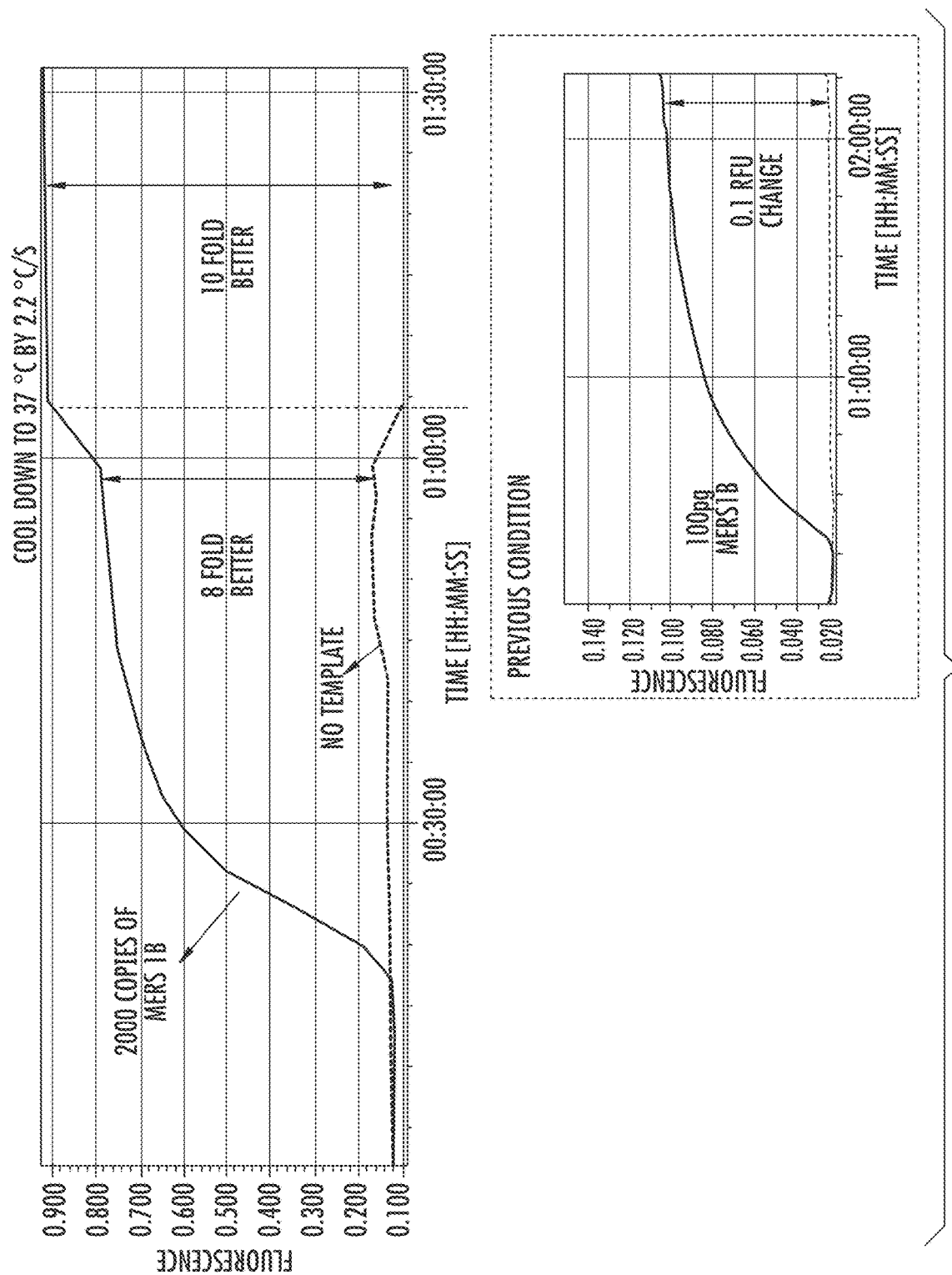

FIG. 35 shows an example using 1:1.2=F:Q OSD reporter (540 nM F strand). The primer concentration was increased by 6 fold, dNTPs by 3 fold, and Mg2+ to 8 mM then run the reaction at 60° C. for 1 h with 60 Unit Bst.2.0. 37° C. fluorescence was used, which was the lowest temperature available using the light cycler.

Figure 36:
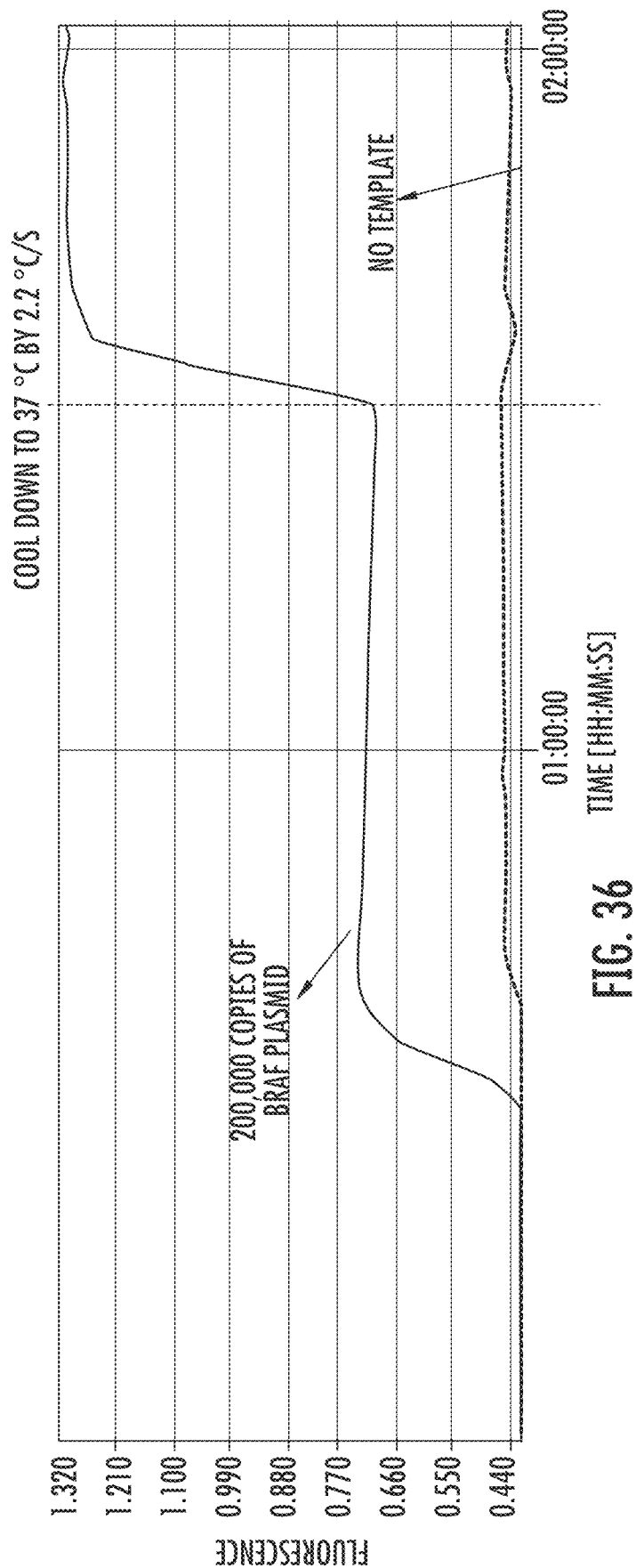

FIG. 36 shows another template, BRAF, one of the melanoma biomarkers. Also used is a 1:1.2=F:Q OSD reporter (540 nM F strand). Since BRAF OSD is less stable than the MERS1B OSD at 60° C., a higher fluorescence signal (up to 1.3) can be seen at 37° C. The primer concentration can be increased by 6 fold, dNTPs by 3 fold, and Mg' to 8 mM, and the reaction run at 60° C. for 1 hour with 60 Unit Bst.2.0. 37° C. fluorescence was used, which was the lowest temperature available using the light cycler.

Figure 37:
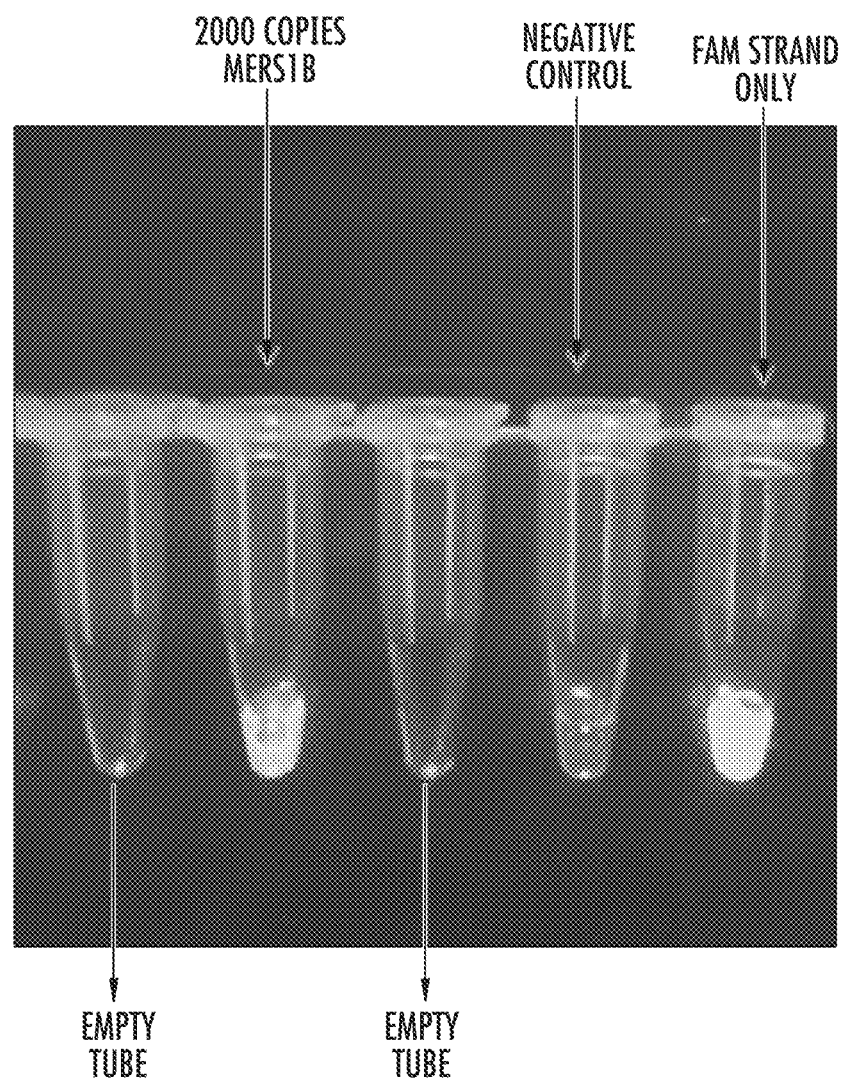

FIG. 37 shows MERS1B fluorescence imaging result with 9 fold reporter and more concentrated other components.

Figure 38:
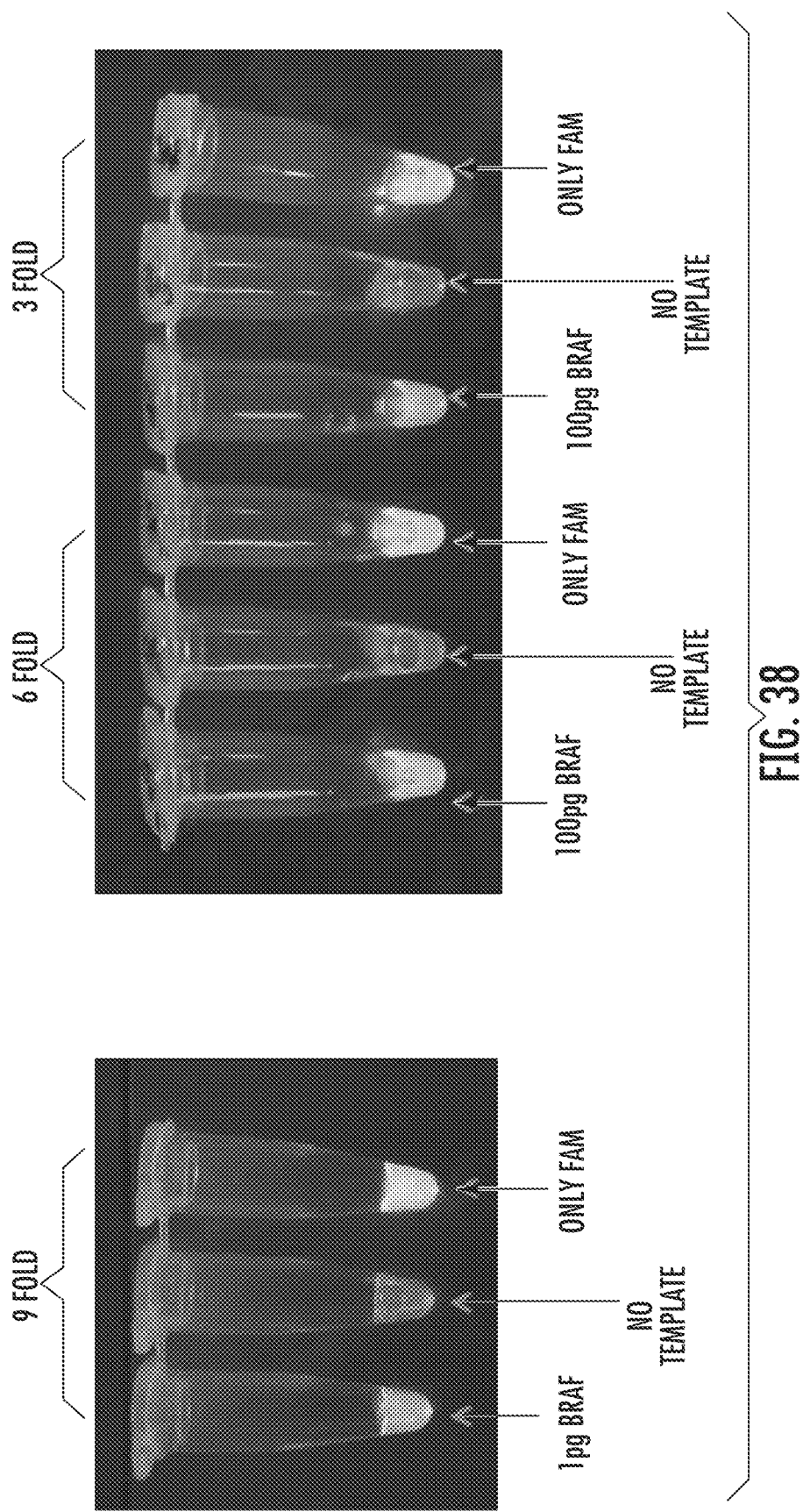

FIG. 38 shows BRAF fluorescence imaging result with 9 fold, 6 fold and 3 fold reporter and more concentrated other components.

Figure 39:
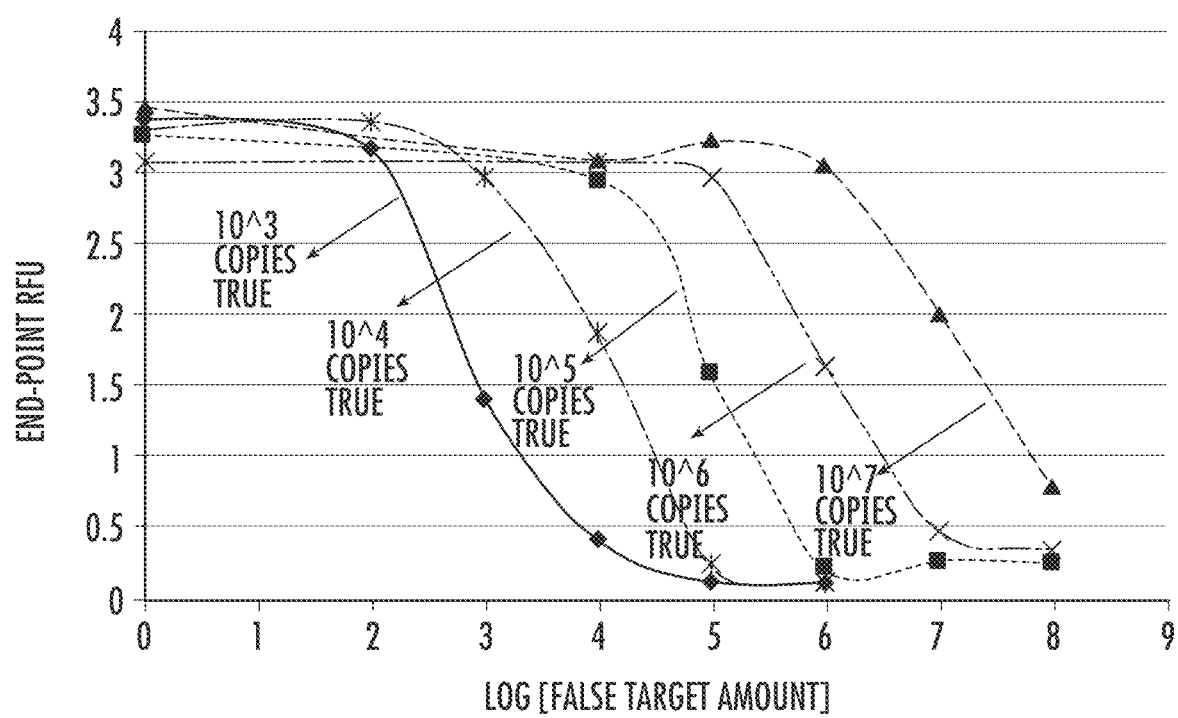

FIG. 39 shows MERS1B end point fluorescence value with different-amount-combination of false target and true target.

Figure 40:
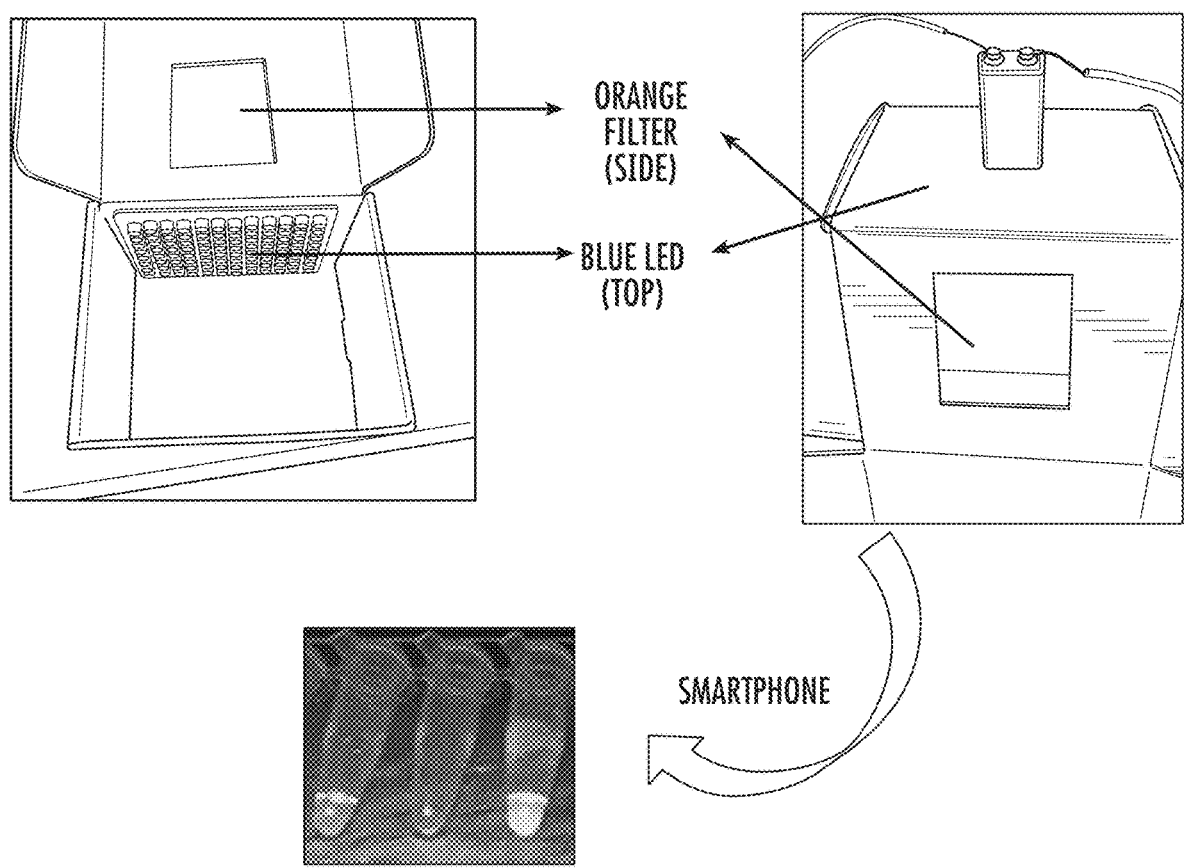

FIG. 40 shows a black box and a corresponding photo. Three tubes from left to right: A) MERS1B negative control, B) empty tube and C) MERS1B positive sample.

Figure 41:
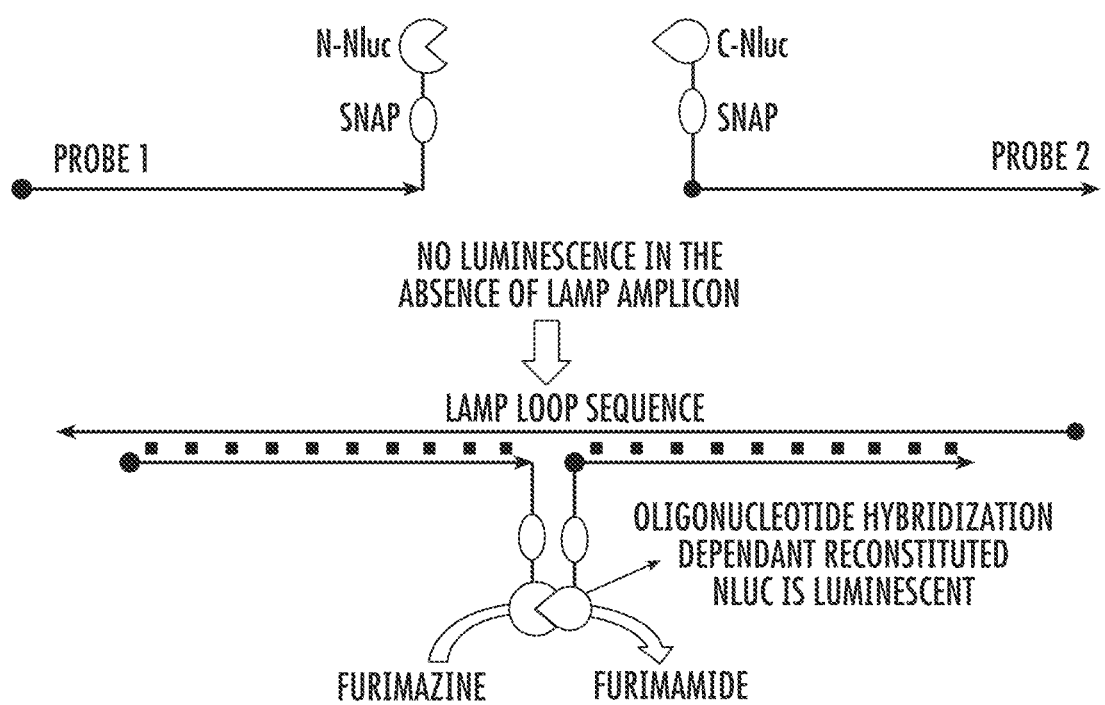

FIG. 41 shows split NLuc reporter of LAMP-OSD.

Figure 42:
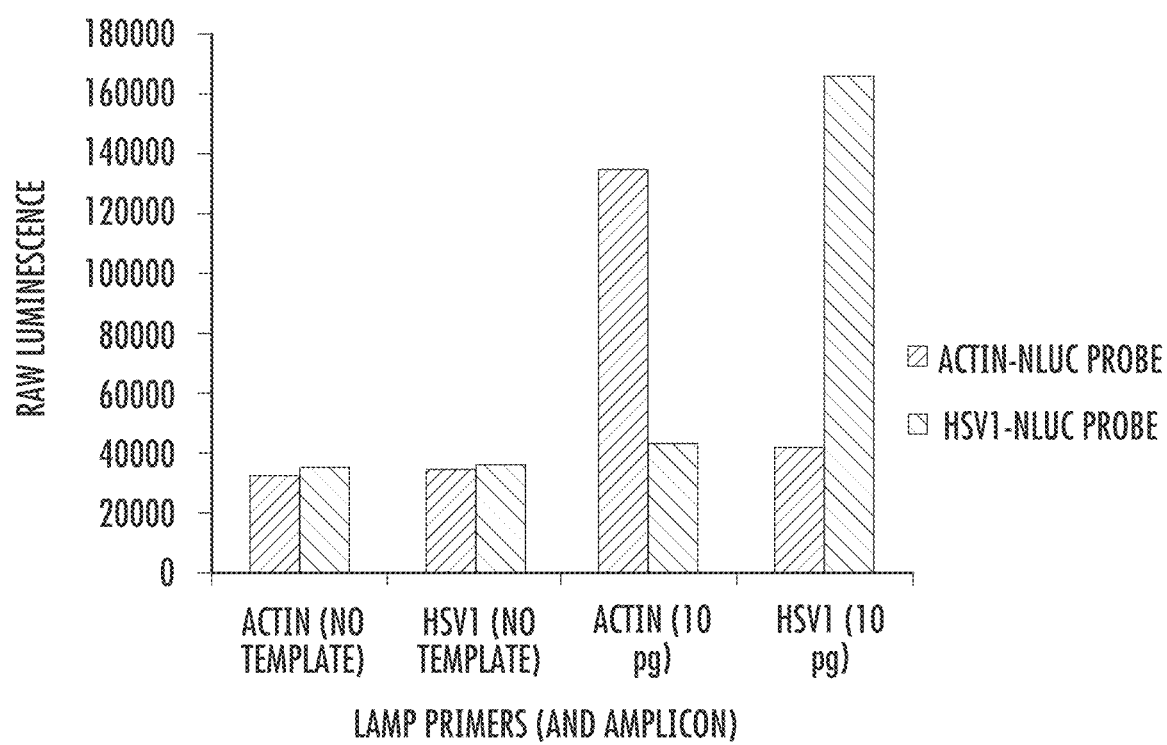

FIG. 42 shows LAMP amplicon detection using sequence-specific split NLuc reconstitution.

Figure 43:
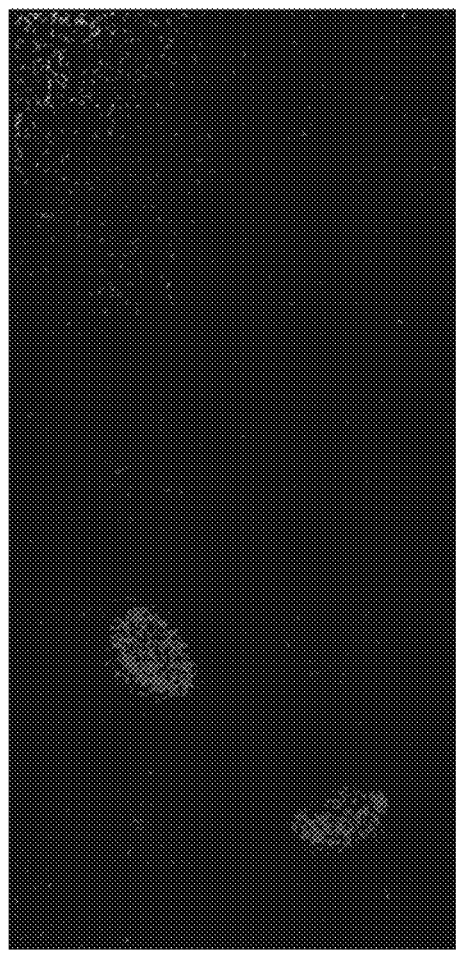

FIG. 43 shows sequence-specific bioluminescent detection of LAMP amplicons using split NLuc-oligonucleotide probes and cellphone imaging. This image was acquired after a 30 second exposure.

Figure 44:
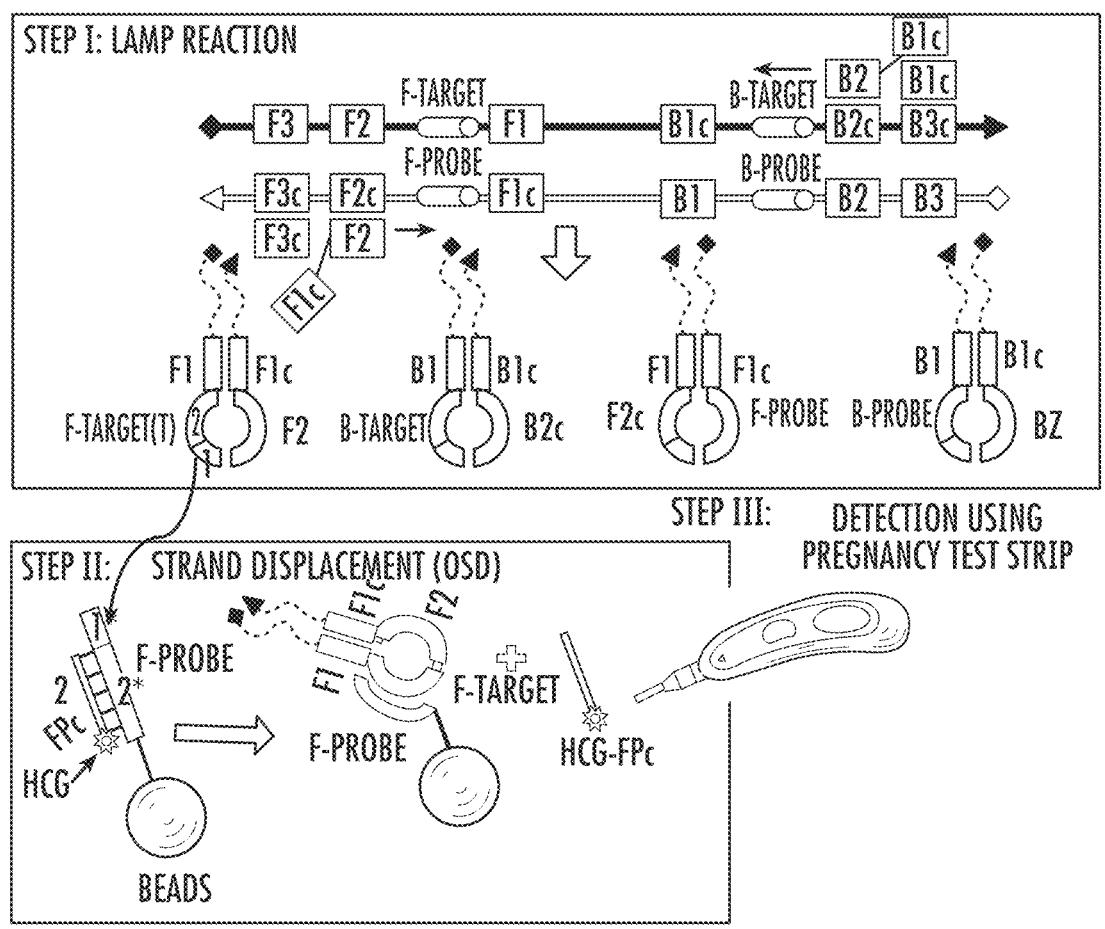

FIG. 44 shows an adapted pregnancy test strip to detect diseases.

Figure 45:

FIG. 45 shows detection of synthetic LAMP mimic oligonucleotides using hCG-OSD.

VI. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "self-assembly pathway" is a series of reactions autonomously executed by nucleic acid sequences in the execution of hybridized, detectable nucleic acid sequences. The self-assembly pathway comprises assembly, or hybridization, of nucleic acid sequences. In some embodiments, the self-assembly pathway can also comprise one or more disassembly reactions.

The term "nucleic acid" refers to natural nucleic acids, artificial nucleic acids, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "hairpin" as used herein refers to a structure formed by intramolecular base pairing in a single-stranded polynucleotide ending in an unpaired loop (the "hairpin loop"). In various embodiments, hairpins comprise a hairpin loop protected by stems. For example, a hairpin can comprise a first stem region, a hairpin loop region, and a second stem region. The first and second stem regions can hybridize to each other and together form a duplex region. Thus, a stem region of a hairpin nucleic acid is a region that hybridizes to a complementary portion of the same nucleic acid to form the duplex stem of a hairpin.

the term "hairpin loop" refers to a single stranded region that loops back on itself and is closed by a single base pair.

"Interior loop" and "internal loop," are used interchangeably and refer to a loop closed by two base pairs. The closing base pairs are separate by single stranded regions of zero or more bases. A "bulge loop" is an interior loop where one of the separated single-stranded regions is zero bases in length and the other is greater than zero bases in length.

An "initiator" is a molecule that is able to initiate the hybridization of two other nucleic acid sequences. The initiator is also referred to herein as the third nucleic acid sequence, while it facilitates the hybridization of what is referred to herein as the first and second nucleic acid sequences.

"Monomers" as used herein refers to individual nucleic acid sequences. For example, monomers are referred to herein as a first nucleic acid sequence, a second nucleic acid sequence, or a third nucleic acid sequence, etc.

By "nucleic acid sequence" is meant a nucleic acid which comprises an individual sequence. When a first, second, or third nucleic acid sequence is referred to, this is meant that the individual nucleotides of each of the first, second, third, etc., nucleic acid sequence are unique and differ from each other. In other words, the first nucleic acid sequence will differ in nucleotide sequences from the second and third, etc. There can be multiple nucleic acid sequences with the same sequence. For instance, when a "first nucleic acid sequence" is referred to, this can include multiple copies of the same sequence, all of which are referred to as a "first nucleic acid sequence."

Typically, at least two different nucleic acid sequences are used in self-assembly pathways, although three, four, five, six or more may be used. Typically each nucleic acid sequence comprises at least one domain that is complementary to at least a portion of one other sequence being used for the self-assembly pathway. Individual nucleic acid sequences are discussed in more detail below.

The term "domain" refers to a portion of a nucleic acid sequence. An "input domain" of a nucleic acid sequence refers to a domain that is configured to receive a signal which initiates a physical and/or chemical change, such as, for example, a conformational change, of the nucleic acid sequence. In some embodiments, an input domain can be an initiator binding domain, an assembly complement domain, or a disassembly complement domain. An "output domain" of a nucleic acid sequence refers to a domain that is configured to confer a signal. For example, the signal can bind a complementary sequence to an input domain. In some embodiments, an output domain is configured to confer a signal to an input domain of another nucleic acid sequence. In some embodiments, an output domain can be, for example, an assembly domain, or a disassembly domain. In some embodiments, an output domain can be present in an initiator.

The term "nucleate" as used herein means to begin a process of, for example, a physical and/or chemical change at a discrete point in a system. The term "nucleation" refers to the beginning of physical and/or chemical changes at discrete points in a system.

The term "toehold" refers to nucleation site of a domain comprising a nuclei acid sequence designed to initiate hybridization of the domain with a complementary nucleic acid sequence. The secondary structure of a nucleic acid sequence may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part of. When exposed, a toehold is configured such that a complementary nucleic acid sequence can nucleate at the toehold.

A "propagation region" as used herein refers to a portion of a domain of a first nucleic acid sequence that is configured to hybridize to a complementary second nucleic acid sequence once the toehold of the domain nucleates at an exposed toehold of the second nucleic acid sequence. The propagation region is configured such that an available secondary nucleic acid sequence does not nucleate at the propagation region; rather, the propagation region hybridizes to the second nucleic acid sequence only after nucleation at the toehold of the same domain.

In some embodiments, nucleic acid sequences can be "metastable." That is, in the absence of an initiator they are kinetically disfavored from associating with other nucleic acid sequences comprising complementary regions.

As used herein, the terms "polymerization" and "assembly" are used interchangeably and refer to the association of two or more nucleic acid sequence, or one or more nucleic acid sequences and an initiator, to form a polymer. The "polymer" may comprise covalent bonds, non-covalent bonds or both. For example, in some embodiments a first, second, and third nucleic acid sequence can hybridize sequentially to form a polymer comprising a three-arm branched junction.

As used herein term "disassembly" refers to the disassociation of an initiator or at least one nucleic acid sequence.

As used herein "reaction graph" refers to a representation of assembly (and, optionally, disassembly) pathways that can be translated into molecular executables.

As used herein the terms "flip" and "switch" are used interchangeably and refer to a change from one state (e.g., accessible) to another state (e.g., inaccessible).

"Kinetically trapped" means that the nucleic acid sequences are inaccessible. In other words, a nucleic acid sequence which is "kinetically trapped" is not available for hybridization. For example, a nucleic acid sequence which has formed a hairpin is considered to be kinetically trapped.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

The term "oligonucleotides," or "oligos" as used herein refers to oligomers of natural (RNA or DNA) or modified nucleic acid sequences or linkages, including natural and unnatural deoxyribonucleotides, ribonucleotides, anomeric forms thereof, peptide nucleic acid monomers (PNAs), locked nucleotide acids monomers (LNA), and the like and/or combinations thereof, capable of specifically binding to a single-stranded polynucleotide by way of a regular pattern of sequence-to-sequence interactions, such as Watson-Crick type of base pairing, base stacking, Hoogsteen or reverse Hoogsteen types of base pairing, or the like. Usually nucleic acid sequences are linked by phosphodiester bonds or analogs thereof to form oligonucleotides ranging in size from a few base units, e.g., 8-12, to several tens of base units, e.g., 100-200. Suitable oligonucleotides may be prepared by the phosphoramidite method described by Beaucage and Carruthers (Tetrahedron Lett., 22, 1859-1862, 1981), or by the triester method according to Matteucci, et al. (J. Am. Chem. Soc., 103, 3185, 1981), both incorporated herein by reference, or by other chemical methods such as using a commercial automated oligonucleotide synthesizer. Oligonucleotides (both DNA and RNA) may also be synthesized enzymatically for instance by transcription or strand displacement amplification. Typically, oligonucleotides are single-stranded, but double-stranded or partially double-stranded oligos may also be used in certain embodiments of the invention. An "oligo pair" is a pair of oligos that specifically bind to one another (i.e., are complementary (e.g., perfectly complementary) to one another).

The terms "complementary" and "complementarity" refer to oligonucleotides related by base-pairing rules. Complementary nucleotides are, generally, A and T (or A and U), or C and G. For example, for the sequence "5'-AGT-3'," the perfectly complementary sequence is "3'-TCA-5'." Methods for calculating the level of complementarity between two nucleic acids are widely known to those of ordinary skill in the art. For example, complementarity may be computed using online resources, such as, e.g., the NCBI BLAST website (ncbi.nlm.nih.gov/blast/producttable.shtml) and the Oligonucleotides Properties Calculator on the Northwestern University website (basic.northwestern.edu/biotools/oligocalc.html). Two single-stranded RNA or DNA molecules may be considered substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%. Two single-stranded oligonucleotides are considered perfectly complementary when the nucleotides of one strand, optimally aligned and with appropriate nucleotide insertions or deletions, pair with 100% of the nucleotides of the other strand. Alternatively, substantial complementarity exists when a first oligonucleotide will hybridize under selective hybridization conditions to a second oligonucleotide. Selective hybridization conditions include, but are not limited to, stringent hybridization conditions. Selective hybridization, or substantially complementary hybridization, occurs when at least about 65% of the nucleic acid sequences within a first oligonucleotide over a stretch of at least 14 to 25 sequences pair with a perfectly complementary sequences within a second oligonucleotide, preferably at least about 75%, more preferably at least about 90%. Preferably, the two nucleic acid sequences have at least 95%, 96%, 97%, 98%, 99% or 100% of sequence identity. See, M. Kanehisa, Nucleic Acids Res. 12, 203 (1984), incorporated herein by reference. For shorter nucleotide sequences selective hybridization occurs when at least about 65% of the nucleic acid sequences within a first oligonucleotide over a stretch of at least 8 to 12 nucleotides pair with a perfectly complementary nucleic acid sequence within a second oligonucleotide, preferably at least about 75%, more preferably at least about 90%. Stringent hybridization conditions will typically include salt concentrations of less than about 1 M, more usually less than about 500 mM and preferably less than about 200 mM. Hybridization temperatures can be as low as 5° C., and are preferably lower than about 30° C. However, longer fragments may require higher hybridization temperatures for specific hybridization. Hybridization temperatures are generally at least about 2° C. to 6° C. lower than melting temperatures (Tm), which are defined below.

As used herein, "two perfectly matched nucleotide sequences" refers to a nucleic acid duplex wherein the two nucleotide strands match according to the Watson-Crick basepair principle, i.e., A-T and C-G pairs in DNA:DNA duplex and A-U and C-G pairs in DNA:RNA or RNA:RNA duplex, and there is no deletion or addition in each of the two strands.

The term, "mismatch" refers to a nucleic acid duplex wherein at least one of the nucleotide base pairs do not form a match according to the Watson-Crick basepair principle. For example, A-C or U-G "pairs" are lined up, which are not capable of forming a basepair. The mismatch can be in a single set of bases, or in two, three, four, five, or more basepairs of the nucleic acid duplex.

As used herein, "complementary to each other over at least a portion of their sequence" means that at least two or more consecutive nucleotide base pairs are complementary to each other. For example, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotide base pairs can be complementary to each other over the length of the nucleic acid sequence.

As used herein, "substantially hybridized" refers to the conditions under which a stable duplex is formed between two nucleic acid sequences, and can be detected. This is discussed in more detail below.

As used herein, "melting temperature" ("Tm") refers to the midpoint of the temperature range over which nucleic acid duplex, i.e., DNA:DNA, DNA:RNA and RNA:RNA, is denatured.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures (See generally, Ausubel (Ed.) Current Protocols in Molecular Biology, 2.9A. Southern Blotting, 2.9B. Dot and Slot Blotting of DNA and 2.10. Hybridization Analysis of DNA Blots, John Wiley & Sons, Inc. (2000)).

As used herein, a "significant reduction in background hybridization" means that non-specific hybridization, or hybridization between unintended nucleic acid sequences, is reduced by at least 80%, more preferably by at least 90%, even more preferably by at least 95%, still more preferably by at least 99%.

By "preferentially binds" it is meant that a specific binding event between a first and second molecule occurs at least 20 times or more, preferably 50 times or more, more preferably 100 times or more, and even 1000 times or more often than a nonspecific binding event between the first molecule and a molecule that is not the second molecule. For example, a capture moiety can be designed to preferentially bind to a given target agent at least 20 times or more, preferably 50 times or more, more preferably 100 times or more, and even 1000 times or more often than to other molecules in a biological solution. Also, an immobilized binding partner, in certain embodiments, will preferentially bind to a target agent, capture moiety, or capture moiety/target agent complex. While not wishing to be limited by applicants present understanding of the invention, it is believed binding will be recognized as existing when the Ka is at $10^7$ l/mole or greater, preferably $10^8$ l/mole or greater. In the embodiment where the capture moiety is comprised of antibody, the binding affinity of $10^7$ l/mole or more may be due to (1) a single monoclonal antibody (e.g., large numbers of one kind of antibody) or (2) a plurality of different monoclonal antibodies (e.g., large numbers of each of several different monoclonal antibodies) or (3) large numbers of polyclonal antibodies. It is also possible to use combinations of (1)-(3). The differential in binding affinity may be accomplished by using several different antibodies as per (1)-(3) above and as such some of the antibodies in a mixture could have less than a four-fold difference. For purposes of most embodiments of the invention an indication that no binding occurs means that the equilibrium or affinity constant Ka is $10^6$ l/mole or less. Antibodies may be designed to maximize binding to the intended antigen by designing peptides to specific epitopes that are more accessible to binding, as can be predicted by one skilled in the art.

The term "sample" in the present specification and claims is used in its broadest sense and can be, by non-limiting example, any sample that is suspected of containing a target agent(s) to be detected. It is meant to include specimens or cultures (e.g., microbiological cultures), and biological and environmental specimens as well as non-biological specimens. Biological samples may comprise animal-derived materials, including fluid (e.g., blood, saliva, urine, lymph, etc.), solid (e.g., stool) or tissue (e.g., buccal, organ-specific, skin, etc.), as well as liquid and solid food and feed products and ingredients such as dairy items, vegetables, meat and meat by-products, and waste. Biological samples may be obtained from, e.g., humans, any domestic or wild animals, plants, bacteria or other microorganisms, etc. Environmental samples can include environmental material such as surface matter, soil, water (e.g., contaminated water), air and industrial samples, as well as samples obtained from food and dairy processing instruments, apparatus, equipment, utensils, disposable and non-disposable items. These examples are not to be construed as limiting the sample types applicable to the present invention. Those of skill in the art would appreciate and understand the particular type of sample required for the detection of particular target agents (Pawliszyn, J., *Sampling and Sample Preparation for Field and Laboratory,* (2002); Venkatesh Iyengar, G., et al., *Element Analysis of Biological Samples: Principles and Practices* (1998); Drielak, S., *Hot Zone Forensics: Chemical, Biological, and Radiological Evidence Collection* (2004); and Nielsen, D. M., *Practical Handbook of Environmental Site Characterization and Ground-Water Monitoring* (2005)).

A substance is commonly said to be present in "excess" or "molar excess" relative to another component if that component is present at a higher molar concentration than the other component. Often, when present in excess, the component will be present in at least a 10-fold molar excess and commonly at 100-1,000,000 fold molar excess. Those of skill in the art would appreciate and understand the particular degree or amount of excess preferred for any particular reaction or reaction conditions. Such excess is often empirically determined and/or optimized for a particular reaction or reaction conditions.

As used herein, "a promoter, a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein, "operatively linked or operationally associated" refers to the functional relationship of nucleic acids with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, "RNA polymerase" refers to an enzyme that synthesizes RNA using a DNA or RNA as the template. It is intended to encompass any RNA polymerase with conservative amino acid substitutions that do not substantially alter its activity.

As used herein, "reverse transcriptase" refers to an enzyme that synthesizes DNA using a RNA as the template. It is intended to encompass any reverse transcriptase with conservative amino acid substitutions that do not substantially alter its activity.

"Enzymatically produced" refers to the production or secondary or tertiary folding of a nucleic acid by an enzyme rather than by chemical synthesis. Enzymatically produced nucleic acids can be made in vitro or in vivo. For example, ribozyme-containing transcription template scaffolds can be engineered to enable enzymatic co-transcriptional synthesis of RNA circuits that can operate without any post-synthetic separation and re-folding of individual circuit components.

B. SYSTEMS, METHODS, AND DEVICES

Disclosed herein are systems and methods, as well as the components to be used to prepare the disclosed systems, devices, and methods. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nucleic acid sequence is disclosed and discussed and a number of modifications that can be made to a number of molecules including the nucleic acid sequence are discussed, specifically contemplated is each and every combination and permutation of the nucleic acid sequence and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Molecular diagnostics that can specifically detect sequences in real-time are particularly valuable for point-of-need detection and point-of-care monitoring of infectious diseases (Griffith et al. A. T. S. M. D. Am. J. Respir. Crit. Care Med. 2007, 175, 367; Dunlap et al. Sci Assembly Microbiology, T. Am. J. Respir. Crit. Care Med. 2000, 161, 1376). Sequence amplification methods such as the polymerase chain reaction (PCR) have been widely used in clinical diagnostics (Saiki et al. Nature 1986, 324, 163), but have infrastructure requirements that make them less useful for point-of-care applications. In contrast, a series of powerful isothermal nucleic acid amplification (IsoT) techniques have been developed that have applications in research, diagnostics, forensics, medicine, and agriculture (Li et al. Analytical Chemistry 2012, 84, 8371; Asiello et al. Lab on a Chip 2011, 11, 1420). These techniques include self-sustained sequence replication (3SR), nucleic acid sequence-based amplification (NASBA), signal-mediated amplification of RNA technology (SMART), strand displacement amplification (SDA), isothermal multiple displacement amplification (IMDA), helicase-dependent amplification (HDA), single primer isothermal amplification (SPIA), and loop-mediated isothermal amplification of DNA (LAMP).

In general, however, isothermal amplification methods are plagued by a loss of specificity that occurs during such robust amplification. Off-target amplicons are an especially pernicious problem for LAMP, in part because of its extraordinary ability to amplify even small numbers of template. The presence of any random parasite or side-product can easily produce "false positive" signals. This lack of specificity is compounded during real-time detection as many of the signal outputs typically utilized can also easily misread false amplicons as true signals (Njiru et al. Plos Neglected Tropical Diseases 2008; Tomita et al. Nature Protocols 2008, 3, 877). For example, when crudely monitoring either the increase of calcein fluorescence (i.e. intercalating dye) or the solution turbidity due to the excessive release of pyrophosphate from nucleoside triphosphates (Boehme et al. Journal of Clinical Microbiology 2007, 45, 1936; Pandey et al. Journal of Medical Microbiology 2008, 57, 439), each method tracks the accumulation of base-pairs—regardless of specificity. While it is true that the final concatameric products of real-time IsoT detection can be (and often are) alternatively verified via subsequent agarose gel electrophoresis (Notomi et al. Nucleic Acids Research 2000, 28), studies note that dye staining with ethidium bromide yields limited quantitative results (Notomi et al. Nucleic Acids Research 2000, 28; Iwamoto et al. Journal of Clinical Microbiology 2003, 41, 2616). Thus, simultaneous real-time and specific detection of isothermal amplification reactions has remained elusive.

Disclosed herein is a method of detecting a nucleic acid, the method comprising amplifying a target nucleic acid using an isothermal amplification reaction, such as LAMP, wherein the isothermal amplification reaction produces at least one loop product, wherein at least part of the single-stranded portion of the loop product represents the target nucleic acid; exposing the loop product of step a) to a strand displacement reporter, such as OSD, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the loop product representing the target nucleic acid; and c) allowing the loop product and the strand displacement reporter to interact, wherein interaction between the strand displacement reporter and the target nucleic acid portion of the loop product produces a signal, wherein the signal indicates the presence of the target nucleic acid.

The methods disclosed herein can take place in a single reaction vessel, making it both convenient and reducing the chance of contamination. Disclosed herein are multiple devices that can be used with the methods disclosed herein, such as microfluidic devices or other "one-pot" amplification/reaction devices.

1. Isothermal Amplification

Figure 1:
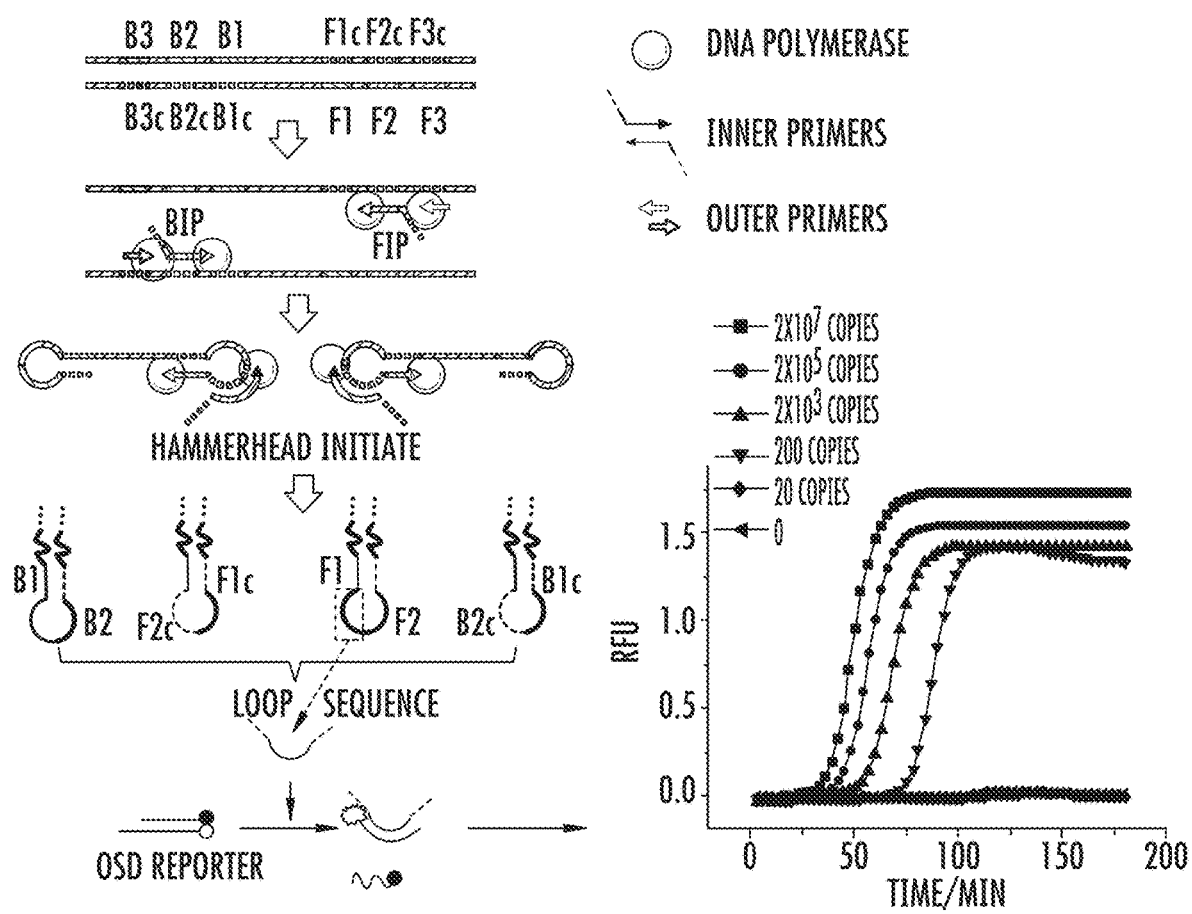

The methods and devices disclosed herein can be carried out using a variety of known isothermal amplification reactions, as well as thermocycling amplification techniques such as PCR and asymmetric PCR. Examples of isothermal amplification include, but are not limited to, Rolling Circle Amplification (RCA), Recombinase Polymerase Amplification (RPA), Strand Displacement Amplification (SDA), and Loop-Mediated Isothermal Amplification (LAMP). Other examples include nucleic acid sequence based amplification (NASBA), transcription mediated amplification (TMA), and helicase dependent amplification (HDA). Yet another example is cross-priming amplification (CPA). CPA is discussed in more detail in Fang et al. (Cross-Priming Amplification for Rapid Detection of *Mycobacterium tuberculosis* in Sputum Specimens, Journal of Clinical Microbiology, March 2009, p. 845-847 Vol. 47, No. 3) and Xu et al. (Cross Priming Amplification: Mechanism and Optimization for Isothermal DNA Amplification, Scientific Reports, February 2012, Vol. 2 No. 246), both of which are hereby incorporated by reference in their entirety for their disclosure of CPA. Examples of RCA and SDA can be seen in FIG. 10. An example of a LAMP reaction scheme is shown in FIG. 1.

Regarding LAMP in particular, it is a powerful isothermal nucleic acid amplification technique that can generate $\sim 10^9$ copies from less than 10 copies of template DNA within an hour or two. Unfortunately, while the amplification reactions are extremely powerful, quantitative detection of LAMP products has remained analytically challenging. In order to both improve the specificity of LAMP detection and to make direct readouts simpler and more reliable, disclosed herein are methods, systems, and devices based on the concept of replacing the intercalating dye typically used in real-time fluorescence reading with a strand displacement reaction, such as a toehold-mediated strand exchange reaction developed called one-step strand displacement (OSD). Due to the inherent sequence specificity of toehold-mediated strand exchange, the OSD reporter has been proven to successfully distinguish side-products from true amplicons of the RPOB and BRAF genes during LAMP. Surprisingly, OSD also demonstrated specificity in detecting single nucleotide polymorphisms (SNPs) in the mutated BRAF gene V600E and during multiplex analysis of various other genes.

LAMP can be conducted with two, three, four, five, or six primers, for example. OSD-LAMP with 2 primers (FIP+BIP) and also 3 primers (FIP+BIP+F3 and FIP+BIP+B3). 2 as well as 3-primer OSD-LAMP assays also well. The five primer LAMP system disclosed herein, and depicted in FIG. 1, is ultra-fast, sensitive, and a highly selective.

The 4-primer LAMP is the basic form of LAMP that was originally described for isothermal nucleic acid amplification. The system is composed of two loop-forming inner primers FIP and BIP and two outer primers F3 and B3 whose primary function is to displace the DNA strands initiated from the inner primers thus allowing formation of the loops and strand displacement DNA synthesis. Subsequently 6-primer LAMP was reported that incorporated 2 additional primers, LF and LB, that bind to the loop sequences located between the F1/F1c and F2/F2c priming sites and the B1/B1c and B2/B2c priming sites. Additional of both loop primers significantly accelerated LAMP. The 5-primer LAMP has been described herein, wherein the 4 LAMP primers (F3, B3, FIP and BIP) are used in conjunction with only one of the loop primers (either LF or LB). This allows the accelerated amplification afforded by the loop primer while using the other LAMP loop (not bound by the loop primer) for hybridization to loop-specific OSD probe. This innovation allows for high-speed LAMP operation while performing real-time sequence-specific signal transduction.

Referring to FIG. 1, the four "loop products" shown after the "hammerhead initiation" step can be used with the methods and devices disclosed herein in order to detect a target nucleic acid Importantly, at least one of the loop products can comprise all or a portion of the target nucleic acid in the single-stranded "loop" portion of the product. The single-stranded loop portion can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides which can be detected, and are considered the "target nucleic acid." By "a portion" is meant that the single stranded nucleic acid of the loop may not wholly comprise the target nucleic acid, but may comprise the target nucleic acid as well as other nucleic acids. It can also mean that only a portion of the target nucleic acid is exposed in the single stranded portion of the loop product, while the remaining portion of the target nucleic acid is in the double-stranded portion of the loop product. The duplex portion of LAMP can also be used as well. For example, the target nucleic acid may comprise a 10-base nucleic acid, while the loop portion itself is 20 bases. One of the nucleotide bases of the 10-base nucleic acid may vary, such as the case with single nucleotide polymorphisms (SNPs). When this is the case, the OSD reporters disclosed herein can discriminate between a wild-type and a variant thereof, such as a SNP.

LAMP can be carried out using DNA or RNA (RT-LAMP). LAMP can amplify nucleic acids from a wide variety of samples. These include, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., J Cell Physiol. (2007) 210(2):279-89; Osada et al., Carcinogenesis. (2007) 28(1):2-12; and Mattes et al., Am J Respir Cell Mol Biol. (2007) 36(1):8-12, each of which is incorporated herein by reference in its entirety).

Some embodiments utilize nucleic acid samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to desirable or archival tissue samples. Most patient-derived pathological samples are routinely fixed and paraffin-embedded to allow for histological analysis and subsequent archival storage.

The target analytes can be nucleic acids. A nucleic acid of the present invention, whether referring to the target nucleic acid or the strand displacement reporter, will generally contain phosphodiester bonds (for example in the case of the target sequences), although in some cases, nucleic acid analogs are included that may have alternate backbones, comprising, for example, phosphoramide (Beaucage et al. Tetrahedron (1993) 49(10):1925 and references therein; Letsinger, J. Org. Chem. (1970) 35:3800; Sprinzl et al., Eur. J. Biochem. (1977) 81:579; Letsinger et al., Nucl. Acids Res. (1986) 14:3487; Sawai et al, Chem. Lett. (1984) 805; Letsinger et al., J. Am. Chem. Soc. (1988) 110:4470; and Pauwels et al. Chemica Scripta (1986) 26:141), phosphorothioate (Mag et al., Nucleic Acids Res. (1991) 19:1437; and U.S. Pat. No. 5,644,048), phosphorodithioate (Briu et al., J. Am. Chem. Soc. (1989) 111:2321, methylphophoroamidite linkages (see Eckstein, Oligonucleotides and Analogues: A Practical Approach, Oxford University Press), and peptide nucleic acid backbones and linkages (see Egholm, J. Am. Chem. Soc. (1992)114:1895; Meier et al., Chem. Int. Ed. Engl. (1992) 31:1008; Nielsen, Nature, (1993) 365:566; Carlsson et al., Nature (1996) 380:207, all of which are incorporated herein by reference in their entirety). Other analog nucleic acids include those with bicyclic structures including locked nucleic acids, Koshkin et al., J. Am. Chem. Soc. (1998) 120:13252 3); positive backbones (Denpcy et al., Proc. Natl. Acad. Sci. USA (1995) 92:6097; non-ionic backbones (U.S. Pat. Nos. 5,386,023, 5,637,684, 5,602,240, 5,216,141 and 4,469,863; Kiedrowski et al., Angew. Chem. Intl. Ed. English (1991) 30:423; Letsinger et al. J. Am. Chem. Soc. (1988) 110:4470; Letsinger et al., Nucleoside & Nucleotide (1994) 13:1597; Chapters 2 and 3, ASC Symposium Series 580, Ed. Y. S. Sanghui and P. Dan Cook; Mesmaeker et al., Bioorganic & Medicinal Chem. Lett. (1994) 4:395; Jeffs et al., J. Biomolecular NMR (1994) 34:17; Xu et al., Tetrahedron Lett. (1996) 37:743) and πon-ribose backbones, including those described in U.S. Pat. Nos. 5,235,033 and 5,034,506, and Chapters 6 and 7, ASC Symposium Series 580, Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are herein expressly incorporated by reference. These modifications of the ribose-phosphate backbone may be done to facilitate the addition of labels or other moieties, to increase or decrease the stability and half-life of such molecules in physiological environments, etc.

2. Strand Displacement Reporters

In the past decade, nucleic acid circuits and computation devices (Benenson et al. Proceedings of the National Academy of Sciences of the United States of America 2003, 100, 2191; Yin et al. Nature 2008, 451, 318) have been developed to perform enzyme-free sequence-specific amplification (Li et al., Analytical Chemistry 2012, 84, 8371; Niu et al. Chemical Communications 2010, 46, 3089; Li et al. Nucleic acids research 2011, 39). These logically designed systems have traditionally been based on nucleic acid strand exchange; such reactions have been widely used to discriminate even slight defects in DNA structure (Li et al. Journal of the American Chemical Society 2012, 134, 13918) and SNPs in a gene (Niu et al. Chemical Communications 2010, 46, 3089) due to their manipulable kinetic properties. To this end, a thermostable version of toehold-mediated, strand exchange-based reaction OSD was developed. As shown herein, this system has been used to detect the *Mycobacterium tuberculosis* (MTB) gene RPOB and the melanoma biomarker gene BRAF under wild-type and SNP conditions (Example 1). There are four primers in one traditional LAMP reaction (FIG. 1): two inner primers (FIP and BIP) and two outer primers (F3 and B3). FIP is comprised of sequence F2 and F1c (F1c-F2). Similarly BIP is comprised of sequence B2 and B1c (B1c-B2). The generation of the two hammerhead-structured intermediates initiates the exponential accumulation of LAMP product. It is noted, however, that the methods disclosed herein can be used with 2, 3, 4, 5, or 6 primers.

The detection method disclosed herein is referred to as "one-step toehold-based strand displacement," or "OSD." The reporter used with this system is referred to herein as the "OSD reporter." The OSD reporter is a duplex, and can be used with any number of detection platforms and devices. For example, the OSD reporter can comprise a fluorophore and quencher label, as seen in FIG. 1. As explained in further detail in Example 1, the final LAMP product (referred to herein as the "loop product") is comprised of large molecular weight concatemers containing free loops. These loops are independent of the primer sequences and unique to the template, thus OSD reporters are designed against these loops in order to discriminate true-positive amplicons.

The OSD reporter can have many conformations. For example, the SNP can comprise a loop, hairpin, or other secondary structure. Examples can be seen in FIG. 16, and others are known to those of skill in the art. The OSD molecule can also comprise modified nucleic acids, such as those disclosed above in regard to the target nucleic acid. For example, the OSD molecule can comprise an inverted dT at the 3' end of the molecule. This can deter polymerase extension of the molecule, therefore yielding sequence specificity.

Detection can take place in "real time," or at "end point" (after the amplification has taken place). As can be seen in FIGS. 2 and 11, the detection means can comprise at least one fluorescent moiety, which may be used to generate a detectable signal. The signal may be a change in fluorescence emission or a change in fluorescence polarization. In some embodiments, the detection module may comprise a pair of fluorescence resonance energy transfer (FRET) interactive moieties. The FRET interactive moieties may comprise two different fluorescent dyes. Alternatively, the FRET interactive moieties may comprise a fluorescent dye and a quencher dye. A variety of different fluorescent and quenching moieties, well known in the art, may be included in the detection module (also referred to herein as the signal output unit). Hybridization between a LAMP loop product and an OSD reporter can be seen in FIG. 29. A change in the signal relative to background indicates the presence of the released fragment, which in turn indicates amplification of the target nucleic acid. The signal produced by the OSD reporter can be increased relative to background. Alternatively, the signal produced by the detection means may be decreased relative to background.

Interaction of the OSD reporter with the loop product of the LAMP reaction can be detected by a variety of means which are known to those of skill in the art. Examples include, but are not limited to, electrochemical sensors, magnetic beads, biotin/avidin systems, colorimetrics, ratiometric sensing, and paperfluidics. These are discussed in more detail below. The method of claim 1, wherein a colorimetric detection scheme is used in detection.

In one embodiment, the OSD reporter can be part of a catalytic hairpin assembly (CHA) detection system. In CHA, two partially complementary DNA hairpins are prevented from reacting with one another by ensconcing the complementary sequences within hairpin structures, effectively leading to kinetic trapping of the reaction (Li (2011)). A short, single-stranded oligonucleotide 'catalyst' that can interact with a toehold on one of the hairpins leads to strand displacement and the revelation of sequences that can interact with the other hairpin, the formation of a double-stranded product, and the recycling of the catalyst. Examples of using CHA with the LAMP reaction can be seen in FIGS. 9 and 25, for example.

The methods and devices disclosed herein can be used to detect multiple target nucleic acids simultaneously. For example, FIG. 26 shows that two OSD reporters can be used simultaneously. Each OSD reporter can be complementary to a different target nucleic acid. The OSD reporters in a multiplex assay can be detected using different types of fluorescence, or using different detection schemes, to discriminate from each other. Two, three, four, five, six, seven, eight, nine, ten, or more different target nucleic acids can be detected at the same time with the methods and devices disclosed herein.

The detection methods and devices disclosed herein are not restricted to detecting only nucleic acids, but can detect non-nucleic acid targets as well. This is illustrated in FIG. 18, which shows the use of an aptamer/ligand system. Conformation switching aptamers may be engineered to harbor oligonucleotide sequences that can trigger OSD reporters. However in the absence of bound ligand the toehold sequences of the trigger remain sequestered and are unable to hybridize with the OSD reporters. Upon ligand binding and conformational rearrangement of the aptamer the toeholds are exposed and initiate strand displacement of the OSD probes. Thus, the ligand binding event can be quantitated by measuring OSD signal output.

The detection methods disclosed herein can take place in a variety of conditions. For example, the amplification and detection reactions can take place at 50, 55, 60, 65, or 70° C., or any amount above, below, or in between. The reactions can also occur in a variety of buffer conditions with varying concentrations of betaine. They also occur with reactions performed using different strand displacing polymerases. The reactions can occur in solution or on surfaces such as beads. The reactions also are robust to sequence complexity. They work with target sequences that are AT-rich or GC-rich or have normal (close to 50%) GC ratio.

3. Uses

The methods and devices disclosed herein can be used for multiple applications. Detection and identification of virtually any nucleic acid sequence, or non-nucleic acid sequence, can be accomplished. For example, the presence of specific viruses, microorganisms and parasites can be detected. Genetic diseases can also be detected and diagnosed, either by detection of sequence variations (mutations) which cause or are associated with a disease or are linked (Restriction Fragment Length Polymorphisms or RFLP's) to the disease locus. Sequence variations which are associated with, or cause, cancer, can also be detected. This can allow for both the diagnosis and prognosis of disease. For example, if a breast cancer marker is detected in an individual, the individual can be made aware of their increased likelihood of developing breast cancer, and can be treated accordingly. The methods and devices disclosed herein can also be used in the detection and identification of nucleic acid sequences for forensic fingerprinting, tissue typing and for taxonomic purposes, namely the identification and speciation of microorganisms, flora and fauna.

The methods and devices disclosed herein have applications in clinical medicine, veterinary science, aquaculture, horticulture and agriculture. The methods and devices can also be used in maternity and paternity testing, fetal sex determination, and pregnancy tests.

Specifically, regarding pregnancy tests and their uses, LAMP-OSD reactions have been engineered that convert the pathogen template into soluble human chorionic gonadotropin (hCG) which can then be read by any reliable pregnancy test kit. As shown in FIG. 44, the sensing principle in the device can be divided into three steps: i) isothermal amplification that can amplify RNA or DNA to a detectable concentration; ii) strand displacement to guaranteeing sequence specific recognition and release hCG; iii) detection of released hCG by commercial pregnancy test strip. The key inventive step is transducing virtually any molecular signal into one of the best, most widely available lateral flow devices on the planet. This bypasses the need to develop new antibodies for new lateral flow assays for new pathogens or disease states.

Benzyl guanine (BG) modified OSD was covalently attached to a fusion protein between a SNAP-tag and hCG. This has been optimized for a mammalian expression system, widening the range of potential antibody fusions. ELISA was performed to ensure that the hCG-DNA conjugate retains antibody binding affinity. These hCG-OSD reporters when incubated with varying concentrations of synthetic LAMP analyte sequences produce a specific signal readable by common pregnancy test strips (FIG. 45). This method can be applied for detection of LAMP amplicons.

4. Devices

Disclosed herein are devices for detection of a target nucleic acid, wherein the device comprises: a) an amplification unit, wherein said amplification unit amplifies the target nucleic acid via an isothermal amplification reaction); b) a transducer, wherein said transducer comprises strand displacement reporters, wherein said strand displacement reporters interact with the target nucleic acid amplification product of step a); and c) a signal output unit, which displays the detectable signal of step b).

The amplification unit is the portion of the device where amplification of a nucleic acid takes place. This can be via the LAMP methods disclosed herein, for example. As discussed above, the LAMP method can be modified by using a 5-primer detection scheme, which allows quicker, more efficient amplification, while still allowing for the use of an OSD reporter.

The transducer can comprise the OSD reporter, for example. The OSD reporter can be attached to a solid substrate, or can be in a fluid. Examples of both are given below. The transducer is responsible for detecting interaction between the OSD reporter and the target nucleic acid portion of the loop product. This interaction produces a signal, which indicates the presence of the target nucleic acid. This signal produced can be fluorescent, electrochemical, colorimetric, by magnetic beads, or any other method known for signal production to those of skill in the art. Various types of platforms and associated signals are discussed in more detail below.

The signal output unit detects the signal from the strand displacement reporter. The signal output unit can be part of a computer system, and the signal can be displayed on a monitor. The resulting signal can also be used in a computer processor to compare it to other results or databases, and the results can be displayed. Computer systems and computer readable media are discussed in more detail below.

The amplification unit, transducer, and signal output unit can be in a single device, and can be in fluid communication with each other. For example, amplification and detection can all take place in the same well of a microfluidics device. Furthermore, amplification and detection can take place simultaneously, and detection can occur in "real time."

Alternatively, the amplification unit can be separate from the transducer and the signal output unit. In this case, amplification can occur in a device that is specific for amplification, and the resulting product can then be exposed to a transducer and signal output unit at another location. For example, amplification can occur in a well, the resulting product separated (or not), and the product can then be transferred to a device comprising the transducer, which comprises an OSD reporter, and a signal output unit for detecting the signal generated by the OSD reporter.

In another embodiment, the amplification unit and the transducer can be on the same device, so that the nucleic acid target is amplified, and the resulting product detected by the OSD reporter. As disclosed above, this can occur in the same reaction at the same time. A separate signal output unit can then be used to detect the signal being generated by the OSD reporter, and it can be displayed accordingly.

The device can also comprise a heater. Because the amplification and detection reactions may require a temperature above room temperature, a heat source is contemplated herein. Heat sources may include, but are not limited to, contacting and non-contacting sources, as known in the art. In one embodiment, the heat source may comprise an optical heating device. For example, the optical device may comprise a defocused laser that is directed at an underside of the device. For example, heating may be achieved by using an 808 nm infra-red laser diode module (e.g., icetec-UK) operating at approximately 150 mW directed onto the device. The power of the laser may be controlled through an n-channel power MOSFET gated by a logic optocoupler driven by pulse width modulated (PWM) signal from a microcontroller (e.g., Fox LP3500, Rabbit Semiconductor, Davis, Calif.).

To provide temperature control, the controller may be programmed with a modified proportional-integral control routine using feedback from the pyrometer. The pyrometer feedback may be received by the microcontroller after a calibration correction is applied. To perform optical temperature detection, the sample may be illuminated obliquely, for example, by a high intensity light source having a selected wavelength. In one embodiment, the light source may comprise a blue light emitting diode (LED) that emits light at a wavelength selected within the range between about 450 nm to about 475 nm (e.g., approximately 470 nm). An example of an LED light source capable of this illumination is HLMP CB28 STD00, manufactured by Agilent Technologies, Santa Clara, Calif. Heating may also be achieved by other methods such as by chemical exothermic reactions or by using the computer's CPU-generated heat, or heating specific metals with batteries, etc.

a) Transduction/Detection Using OSD Reporters

In one embodiment, the OSD reporter used with the transducer is labeled, and a signal is detected by a change in the label when the OSD reporter interacts with the loop product (i.e., the target nucleic acid). By "label" or "labeled" herein is meant that a compound has at least one element, isotope or chemical compound attached to enable the detection of the compound, e.g. renders an OSD reporter or transfer product detectable using known detection methods, e.g., electronic, spectroscopic, photochemical, or electrochemiluminescent methods. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio. Suitable dyes for use in the invention include, but are not limited to, fluorescent lanthanide complexes, including those of Europium and Terbium, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), and others described in the 6th Edition of the Molecular Probes Handbook by Richard P. Haugland, herein expressly incorporated by reference. Additional labels include nanocrystals or Q-dots as described in U.S. Ser. No. 09/315,584, herein expressly incorporated by reference.

In some embodiments, fluorescence resonance energy transfer (FRET) pairs are used in the compositions and methods of the reaction. As is described herein, transfer reactions may rely on the transfer of one of a FRET pair from one transfer probe to another, resulting in a differential signal, as is outlined below. In addition, FRET pairs, one on each probe, that upon removal from the target sequence allows detection based on a FRET signal can be used. Other FRET systems are described herein. Suitable FRET pairs are well known in the art.

A secondary detectable label can also be used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™. In a preferred embodiment, the binding partner pair comprises biotin or iminobiotin and streptavidin.

The binding partner pair can comprise a primary detection label (for example, attached to an OSD reporter) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155 200, incorporated herein by reference).

The assays described herein generally rely on increases in signal, e.g. the generation of fluorescence or chemiluminescence, etc., rather than decreases. However, as will be appreciated by those in the art, assays that rely on decreases in signal are also possible.

Signal transduction and detection can be done using solid supports. In one embodiment, the OSD reporters are attached to beads, using either anchor probe/capture probe hybridization or other binding techniques, such as the use of a binding partner pair (e.g. biotin and streptavidin). Beads comprising streptavidin are contacted with the sample, and the beads are examined for the presence of the label, for example using FACS technologies.

Heterogeneous assays can also be used. That is, the reaction is done is solution and the product is added to a solid support, such as an array or beads. Iin another aspect of the invention, one of OSD reporter strands has an attached magnetic bead or some other label (biotin) that allows for the easy manipulation of the reporter. The magnetic bead or label can be attached to either strand using any number of configurations as outlined and suggested herein.

Detection systems are known in the art, and include optical assays (including fluorescence and chemiluminescent assays), enzymatic assays, radiolabelling, surface plasmon resonance, magnetoresistance, cantilever deflection, surface plasmon resonance, etc. In some embodiments, OSD reporter can be used in additional assay technologies, for example, as described in 2006/0068378, hereby incorporated by reference, the OSD reporter can serve as a linker between light scattering particles such as colloids, resulting in a color change in the presence of the OSD reporter.

In some embodiments, the strand displacement reporters of the invention are attached to solid supports for detection. For example, strand displacement reporters can be attached to beads for subsequent analysis. Similarly, bead arrays as described below may be used.

In one embodiment, the present invention provides arrays, each array location comprising at a minimum a covalently attached strand displacement reporter, also referred to herein as a "capture probe". By "array" herein is meant a plurality of nucleic acid probes (OSD reporters, for example) in an array format; the size of the array will depend on the composition and end use of the array. Generally, the array will comprise from two to as many as 100,000 or more reporters, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture probe may be made as well. In addition, in some arrays, multiple substrates may be used, either of different or identical compositions. Thus, for example, large arrays may comprise a plurality of smaller substrates. Nucleic acids arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (Affymetrix GeneChip™), spotting techniques (Synteni and others), printing techniques (Hewlett Packard and Rosetta), origami pads, paperfluidics, electrode arrays, three dimensional "gel pad" arrays, etc. Liquid arrays may also be used.

By "substrate" or "solid support" or other grammatical equivalents herein is meant any material that can be modified to contain discrete individual sites appropriate for the attachment or association of nucleic acids. The substrate can comprise a wide variety of materials, as will be appreciated by those in the art, including, but not limited to glass, plastics, polymers, metals, metalloids, ceramics, organics, etc. When the solid support is a bead, a wide variety of substrates are possible, including magnetic materials, glass, silicon, dextrans, plastics, etc.

In another aspect of the invention, a fluidic is used to automate the methodology described in this invention. See for example U.S. Pat. No. 6,942,771, herein incorporated by reference for components including but not limited to cartridges, devices, pumps, wells, reaction chambers, and detection chambers.

The devices of the invention can comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

Chemically derivatized particles, plates, cartridges, tubes, magnetic particles, or other solid phase matrix with specificity to the assay components can also used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

Platforms for multi-well plates, multi-tubes, holders, cartridges, minitubes, deep-well plates, microfuge tubes, cryovials, square well plates, fitters, chips, optic fibers, beads, and other solid-phase matrices or platform with various volumes can be accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

Interchangeable pipet heads (single or multi-channel) with single or multiple magnetic probes, affinity probes, or pipetters robotically manipulate the liquid, particles, cells, and organisms can be used. Multi-well or multi-tube magnetic separators or platforms manipulate liquid, particles, cells, and organisms in single or multiple sample formats.

The instrumentation can include a detector, which can be a wide variety of different detectors, depending on the labels and assay. In a preferred embodiment, useful detectors include a microscope(s) with multiple channels of fluorescence; plate readers to provide fluorescent, electrochemical and/or electrical impedance analyzers, ultraviolet and visible spectrophotometry detection with single and dual wavelength endpoint and kinetics capability, fluoescence resonance energy transfer (FRET), luminescence, quenching, two-photon excitation, and intensity redistribution; CCD cameras to capture and transform data and images into quantifiable formats; and a computer workstation.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells. Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

The robotic apparatus can include central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory. These robotic fluid handling systems can utilize any number of different reagents, including buffers, reagents, samples, washes, assay components such as label probes, etc.

5. Glucose Meters

Disclosed herein are transducers that can include an enzyme that can catalyze the conversion of a substance (enzyme substrate) into glucose (or any other product that can be detected by any glucose meter). For example, the enzyme can be invertase, sucrase or sucrase-isomaltase which can convert sucrose into glucose, maltase which can convert maltose into glucose, trehalase which can convert trehalose into glucose, lactase which can convert lactose into glucose, amylase or glucoamylase which can convert starch into glucose, or a cellulase that can convert cellulose into glucose. The enzyme can also be an alpha- or beta-glucosidase or debranching enzyme from any source. In one example, the enzyme is attached to the strand displacement reporter, such that in the presence of the target nucleic acid, the enzyme is released from the solid support and can convert the substance into glucose, which can be detected and quantified. In another example, the enzyme is not initially part of the transducer, but instead after the target nucleic acid binds the strand displacement reporter, a second recognition molecule (which may be the same or a different from the strand displacement reporter) which has conjugated thereto the enzyme, binds to the target nucleic acid bound to the strand displacement reporter bound to the solid support, thus creating a type of "sandwich." The bound enzyme can then convert the substance into glucose, which can be detected and in some examples quantified.

One skilled in the art will recognize that any approach using other techniques to transform one target nucleic acid's concentration information into another's, which is subsequently detected using the methods in this application, can be used. For example, if target nucleic acid A can quantitatively produce substance B by a certain technique, one can simply use the methods in this application to detect substance B, and then convert the concentration of substance B into that of target nucleic acid A in the sample.

6. Detection Systems and Computer Systems

Disclosed herein is a non-transitory computer-readable medium with computer-readable instructions stored thereon for use in detecting a nucleic acid, wherein a user inputs instructions, and the computer carries out the steps of: a) amplifying a target nucleic acid using an isothermal amplification reaction, wherein the isothermal amplification reaction produces at least one loop product, wherein at least part of the single-stranded portion of the loop product represents the target nucleic acid; b) exposing the loop product of step a) to a strand displacement reporter, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the loop product representing the target nucleic acid; c) allowing the loop product and the strand displacement reporter to interact, wherein interaction between the strand displacement reporter and the target nucleic acid portion of the loop product produces a detectable signal, wherein the signal indicates the presence of the target nucleic acid, and further wherein the detectable signal is displayed by the computer. In one embodiment, the detectable signals can be compared to a library of known detectable signals, and the results displayed. The isothermal amplification reaction can be LAMP, for example, and the strand displacement reporter can be an OSD reporter, for example.

Disclosed herein are the use of mobile computing platforms to detect and/or quantify nucleic acid amplification using the methods disclosed herein. The embodiments disclosed herein leverage the functionality of mobile computing platforms (i.e., smart-phones, tablets, external handheld computer, and the like) for detecting and/or quantifying nucleic acid amplification reactions. Using a mobile computing platform can enable high performance on an intuitive user interface, while dramatically reducing the size, complexity, and cost of the application specific instrument.

Unlike conventional methods, which take hours to weeks to characterize or analyze even large samples, the present invention typically produces measurements in under an two hours, or under an hour, or under half an hour, for example, in minutes. Unlike the standard diagnostic devices and methods which require bench top equipment in a laboratory or a clinic, highly trained technicians, electricity, water, and, often, refrigeration of samples and reagents, the present invention can be implemented using a portable or mobile device Optionally, results can be distributed via one or more communications networks such as a wireless network and/or the Internet. The system of the present invention does not require skilled labor or trained technicians, and can work outside of hospital or centralized lab infrastructure. The system of the present invention is robust to various environmental variables and can function at wide range of pH, temperatures, traditional overhead infrastructure and, optionally, without refrigeration. Therefore, provided is a system for rapid analysis of biological samples. The system comprises a mobile device to analyze amplification of a biological sample.

As one skilled in the art will appreciate, the present invention can include a hardware portion, a software portion and/or a combination of software and hardware portions. In one embodiment, the present invention is a portable processing means that can detect nucleic acids in a biological sample according to computer-useable instructions embodied on a computer-readable medium.

Further, it should be appreciated that a computer may be embodied in any of a number of forms, such as a laptop computer, a tablet computer, or a computer embedded in a device not generally regarded as a computer but with suitable processing capabilities, including a Personal Digital Assistant (PDA), a smart phone or any other suitable portable or mobile electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, at least a portion of the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a non-transient computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture. The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

The present invention can include a genomic or transcriptomic database for storing a plurality of genomic or transcriptomic profiles or target biomarker sequences. In one embodiment, the present invention can include a signal profile of a single reference sample. The device of the present invention can also connect to a remotely located genomic or transcriptomic database, such as those maintained by the National Institutes of Health, Center for Disease Control, etc. Such connection would facilitate tracking and coordinating responses to outbreaks of disease at widely dispersed analysis sites. Exemplary analysis sites include hospitals, border crossings, airports, refugee camps, farms, quarantine zones, disaster sites, homeless shelters, nursing homes, meat-packing plants, and food processing centers. Those skilled in the art will appreciate still other analysis sites to which the present invention is applicable.

The present invention need not connect directly to genomic or transcriptomic databases, although it may if need be. In other embodiments, the device can connect to genomic or transcriptomic databases through various networks, public or private, such as Local-Area Networks (LANs), Wide-Area Networks (WANs), or the Internet. In one embodiment, genomic databases are accessible across a public network such as the Internet. Data is communicated in a secure means, such as via Secure Socket Layer (SSL) or secure copy.

Also disclosed is a fluorescence or electro-optic detection means for detecting nucleic acids. The fluorescence detection means can include an emitter such as a light-emitting diode and/or a laser diode, a data acquisition device such as a photodetector, photo-multiplier tube (PMT) or a charge-couple device (CCD), avalanche photodiode, and a processing unit for storing and processing the acquired data.

In certain embodiments, the signal intensity versus time may be analyzed to give an indication of the types and quantities of the nucleic acid species present in the biological sample. For example, plotting the detected signal against a signal produced by a reference sample allows the user to determine whether or not pathogens present in the reference sample are present in the sample under test, as identical pathogens will produce signal peaks at the same moment in time (given the same analysis conditions).

Disclosed herein is a portable system for amplifying and detecting nucleic acids using a portable system for analyzing detected signals, and comparing and distributing the results via a wireless network. A portable, chip-based diagnostic device may be used for the rapid and accurate detection of DNA/RNA signatures in biological samples. The portable device may be used as a platform for personalized and mobilized nanomedicine or companion diagnostics and as a tool to improve efficacy, decrease toxicity, and help accelerate clinical trials and regulatory approvals on novel drugs.

In one embodiment, a system may be used in a method for conducting personalized medicine. In a broad sense, personalized medicine uses genetics to provide the right patient with the right drug at the right dose for the right outcome. In an embodiment according to the invention, a portable assay system is used to extract, amplify, and detect nucleic acids in the sample, and in particular to detect personalized biomarkers based on the nucleic acids. The system may then determine an appropriate dosage and/or drug combination for delivery of customized medicine based on the detected personalized biomarkers. A targeted drug and companion diagnostic may be provided. In addition, the system may be used to determine if a person is a responder to a drug therapy. The system can also be used to help stratify patients to enhance drug safety and efficacy, and can help optimize dosing and therapeutic regimens. Further, the system may be used for monitoring a person, for example by monitoring levels of a nucleic acid found in biosamples from the person taken at different times. Such monitoring may be used, for example, to track the progress of a treatment in a patient, or for monitoring a disease in the person. For example, diabetes and other chronic diseases may be diagnosed, classified or monitored via DNA/RNA markers, for example, such as inflammation markers. For example, determining a personalized genomic profile can include detecting nucleic acids indicative of a type or subtype of diabetes.

In another embodiment, a portable system according to an embodiment of the invention may be used to assist in making regulatory clinical trials smaller and less costly, by enriching study populations. Personalizing trials with subset genetic populations can dramatically enhance therapeutic effect, and shorten the approval process. The resulting drug and companion diagnostic combination have a premium value for the target genetic population.

In another embodiment, a portable system according to the invention may be used for providing personalized care, for example in the fields of cosmetics, cosmeceuticals and in skin care applications. For example, a portable assay system may be used to extract, amplify, and detect nucleic acids in the sample; and in particular to detect personalized biomarkers based on the nucleic acids. The system may then determine a type, amount or combination of a personal care product to deliver based on the personalized biomarkers. For example, the system may be used for the selection and delivery of cosmetics based on personalized cosmetic biomarkers. In one example, a skin type is determined based on personalized biomarkers, which may then be used to determine a type, amount or combination of cosmetic products to deliver to a person. A mobile device may be used to measure and quantify, in real time, the presence of key biomarkers (which could, for example, be DNA or R A based). Sequence biomarkers (e.g., beauty biomarkers such as age related locus, certain aging genes or gene expression patterns, skin quality) can be measured against skin products. A portable system according to an embodiment of the invention can be used to correlate the genotype of individuals with such sequence biomarkers. An integrated chip can be customized to go along with a library of target genes for beauty biometrics. An individual's beauty biometrics can be measured by quantifying the individual's beauty biomarkers in real time via a portable system according to an embodiment of the invention. It can then be seen how these biomarkers change over time with the use of corresponding cosmetic products. Embodiments may also be used for wellness applications, for nutrigenomics, and for ayurvedic genomics, for example performing ayurvedic diagnosis via genes corresponding to the vata, kapha and pitta body type.

In another embodiment, a portable system according to the invention may be used in which the detection capabilities of an integrated chip are coupled with specific, uniquely determined pharmaceutical products. For example, a portable assay system may be used to extract, amplify, and detect nucleic acids in the sample; and in particular to detect personalized biomarkers based on the nucleic acids, where the personalized biomarkers may indicate the presence of a specific strain of a disease or pathogen. The system may then uniquely determine a customized dosage and/or drug combination to deliver based on the specific strain biomarkers.

More generally, an embodiment according to the invention may be used to genotype any organism, thereby determining at least one of: predisposition to a genetic disease, a strain of a disease, and antibiotic resistance of a disease condition. For example, a type of viral hepatitis may be determined; or a cancer gene may be identified.

In various embodiments, a portable system according to the invention may be used in a variety of different possible industries. For example, a portable assay system may be used to extract, amplify, and detect nucleic acids in the sample. The detected nucleic acids may then be used in any of a variety of different possible industries (in addition to industries discussed elsewhere herein). For example, the detected nucleic acids may relate to food safety, agricultural diseases, veterinary applications, archaeology, forensics, nutrition, nutriceuticals, nutrigenomics, water testing/sanitation, food and beverages, environmental monitoring, customs, security, defense, biofuels, sports and wellness; and may be used for theragnosis.

In another embodiment according to the invention, systems taught herein are used coupled with an Enhanced External Counter Pulsation (EECP) therapy machine. Levels of cardiac markers, inflammation markers and other markers associated with improvement in cardiac function are monitored in real time by nucleic acid analysis systems taught herein, and used to provide electronic control inputs to the EECP machine, for example to increase or decrease blood flow or titrate dosing. For example, inflammation factors, VEGF, endothelial auto growth factors, other gene expression patterns, cardiac markers, DNA/RNA markers that are correlated with cardiac status, and so on, may be monitored by systems taught herein. By coupling nucleic acid analysis systems taught herein with an EECP therapy machine, there may be provided a tool that helps to reverse atherosclerosis with a combined effect produced by stimulating endothelial repair with flow and with the measurement of inflammatory factors. Biomarkers that are implicated in the atherosclerotic process can be monitored on multiple channels of a nucleic acid analysis system, simultaneously, and electronic control inputs provided to the EECP machine based on the levels of the biomarkers.

In various embodiments, results provided by a portable system according to the invention may include a viral load (e.g., in copies/ml), a predicted cell count per volume (e.g., a predicted CD4 count in cells/mm3), and a titration of drug dosing.

In further embodiments according to the invention, a portable system according to the invention may communicate with other systems in a variety of different possible ways. The portable system may transmit and receive modulated data signals pertaining to the biological sample, and may communicate via wired media (e.g., a wired network or direct-wired connection) or wireless media (e.g., acoustic, infrared, radio, microwave, spread-spectrum). The portable system may, for example, communicate via the World Wide Web, and/or a mobile network, and/or via text message (such as an SMS message). The portable system may connect to a remote genomic database that stores genomic profiles. The portable system may store, or transmit or receive, a signal profile of a single reference sample.

In further embodiments according to the invention, the portable system or mobile device may be implemented as part of, or interface with, any of a variety of different possible widely available handheld or tablet devices, such as a smartphone, Personal Digital Assistant (PDA), cellular phone, or other handheld or tablet device, employing an optionally disposable compact integrated chip. In addition, similar graphical user interfaces and external design may be used as are used on such widely available handheld or tablet devices. In one example, an embodiment according to the invention may be implemented in, or interface with, or use a similar graphical user interface or external interface to that of an iPhone, iPad, or iPod, all sold by Apple Inc. of Cupertino, California, U.S.A., or a Galaxy, sold by Samsung Electronics Co., Ltd. of Suwon, South Korea.

In an embodiment according to the invention, the portable system, or multiple such portable systems at dispersed locations, may be used to track the outbreak of disease at dispersed analysis sites. The portable system may connect through one or more networks (e.g., a Local Area Network, a Wide-Area Network, and/or the Internet); and may engage in a two-way exchange of information between a central data center and the system end-user. The data center can provide known pathogen/disease mapping information to the end-user/invention system for biological sample analysis, and subsequently the invention system/end-user can transmit assay results to the data center. The data center can receive geographic location information and other case identification information from the end-users/invention system. The data center can monitor incoming assay results from the plurality of deployed units/invention systems and employs pattern detection programs, for example to track the outbreak of a disease. The data center can programmatically generate notifications to remote portable systems according to the invention, upon detection of threshold patterns.

In various embodiments, the system of the present invention can be used to identify pathogens, diagnose disorders having a genetic marker, or genotype an individual. The methods of the present invention generally comprise (1) providing at least one integrated chip; (2) loading the at least one biological sample onto the at least one integrated chip; (3) operably connecting a portable control assembly with at least one integrated chip; and (4) activating the portable control assembly to effect extraction, amplification and detection of nucleic acid from the biological sample loaded onto said integrated chip.

The present invention can be used to diagnose and detect a wide variety of pathogens and disorders that have nucleic acid-based genetic material and/or genetic components. The system and method of the present invention can be used to detect and diagnose molecular diagnostic targets arising in the fields of oncology, cardiovascular, identity testing and prenatal screening, Preferably, biological sample is derived from a biological fluid, such as but not limited to blood, saliva, semen, urine, amniotic fluid, cerebrospinal fluid, synovial fluid, vitreous fluid, gastric fluid, nasopharyngeal aspirate and/or lymph.

A biological sample can be a tissue sample, a water sample, an air sample, a food sample or a crop sample. Preferably, the biological sample analysis detects any one or more of water-born pathogen, air-born pathogen, food-born pathogen or crop-born pathogen.

The pathogen detectable by the system and method of the present invention can come from a variety of hosts. The host, whether biological or non-biological, should be capable of supporting replication of an infectious agent by allowing the infectious agent to replicate in or on the host. Examples of such hosts include liquid or solid in vitro culture media, cells or tissues of animals, plants or unicellular organisms, whole organisms including mammals such as humans.

The system and methods of the present invention can be employed in one of more of the following areas. In one embodiment, the system and method of the present invention can be employed in the area of defense against biological weapons. For example, the present invention can be used for point-of-incidence and real-time pathogen-detection. In another embodiment, the system and method of the present invention can be employed in the area of life sciences. For example, the present invention can be used as and with a portable analytical instrument. In another embodiment, the system and method of the present invention can be employed in the area of clinical diagnostics. For example, the present invention can be used to diagnose and/or identify pathogens by doctors, nurses or untrained users in hospitals, homes or in the field. The present invention can also be used for genotyping an organism, thereby determining predisposition to genetic diseases, if any, or antibiotic resistance, if any. The present invention can also be used to determine pathogens present in a patient and the sensitivity and resistance profiles of those pathogens to various antibiotics. The present invention can also be used as a drug monitoring device, a prognostic indicator of disease, and a theragnostic device. In another embodiment, the system and method of the present invention can be employed in the area of industrial and agricultural monitoring. For example, the present invention can be used to monitor and/or detect pathogens born by food, crops, livestock, and the like. In another embodiment, the system and method of the present invention can be employed in the area of forensics. For example, the present invention can be used to genetically identify an individual.

In one embodiment, genetic disorders and disorders having a genetic component can be diagnosed by employing the system and method of the present invention. For example, numerous oncogenes have been identified, including p53, implicated in the development of breast, colorectal and other cancers; c-erbB2, associated with breast cancer development and metastasis; and BRCA1, involved in 50% of all inherited breast cancers, and also associated with increased risk for prostate and other cancers. Screening for the these genetic markers can be accomplished using the system and methods described herein.

The inventions described herein can be configured or utilized in products or devices that include but are not limited to handheld devices, computer tablets, notebooks, smart phones, implantable devices (implantables), ingestible devices (ingestibles), wearable devices (wearables) and injectable devices (injectables).

The device or system can include or be operably coupled to system instructions, e.g., embodied in a computer or computer readable medium. The instructions can control any aspect of the device or system, e.g., to correlate one or more measurements of signal. A system can include a computer operably coupled to the other device components, e.g., through appropriate wiring, or through wireless connections. The computer can include, e.g., instructions that control amplification, e.g., using feedback control as noted above, and/or that specify when images are taken or viewed by the optical train. The computer can receive or convert image information into digital information and/or signal intensity curves as a function of time, determine concentration of a target nucleic acid analyzed by the device, and/or the like. The computer can include instructions for normalizing signal intensity to account for background, e.g., for detecting local background for one or more regions of the array, and for normalizing array signal intensity measurements by correcting for said background. Similarly, the computer can include instructions for normalizing signal intensity by correcting for variability in array capture nucleic acid spotting, uneven field of view of different regions of the array, or the like. The computer can also comprise a display unit for displaying information received from the signal output unit.

7. Quantitation

Disclosed herein are methods not only for determining the presence of a target nucleic acid in a sample, but also for determining the amount of nucleic acid. A quantitative standard is important to distinguish between positive and negative results. For example, levels of bacteria can be quantitated and used with a cut-off point in areas such as food security and environment contamination. In the area of diagnostics, such as those that rely on biomarker screening, this can also be important. For example, cancer biomarkers can be up-regulated in an individual with cancer, as compared to a healthy control. Since isothermal amplification reactions (as well as other means of amplification utilizing polymerases) are terminated by consumption of the primer and dNTP, the final amount of amplicons is determined by primer concentration, rather than the template amount. Therefore, isothermal amplification methods end with the same amount of amplicons regardless of how much template it starts with. This makes quantification information difficult to obtain using these methods. Even for q-PCR, quantification information can only be obtained from the Ct value of real-time reading other than end-point reading.

Disclosed herein is a method of adding a certain amount of false target to the amplification reaction, wherein the false target comprises an essentially identical primer binding region as that of the true target (FIG. 31). For example, the false target can comprise 80, 85, 90, 95, or 100% sequence identity to the primer binding region of the true target. (By "true target" is meant the nucleic acid which one is interested in amplifying and detecting). The false target comprises randomized sequences in the OSD probing region, such that the false target is highly unlikely to be bound by the OSD probing region. The false target can be 80, 70, 60, 50, 40, 30, 20, or 10% or less complementary to the single-stranded nucleic acid of the strand displacement reporter. For example, it can have 1, 2, 3, 4, 5, 6, 7, 8, 9, 10, or more nucleotides which are not complementary to the OSD probing region. If a much larger amount of false target exists in the solution than the true target, the final false amplicons is present at a higher level than the true amplicon. For example, if the false target is amplified more than 2, 3, 4, 5, 6, 7, 8, 9, 10, 11, 12, 13, 14, 15, 16, 17, 18, 19, or 20 fold, for example, then this can be an indication of the level of the true target. If the ratio of false target to true target remains essentially the same after amplification, this shows that the absolute fluorescence intensity is decreased, or "diluted" by the false amplicons. For example, 10-fold false target signal can suppress 1-fold true target signal to approximately 10% of the regular fluorescence intensity.

This strategy allows for semi-quantification of a target. For example, if a standard level for a certain target is known, a 10 fold amount of the standard can be designed and spiked into the sample during preparation, and a "Yes/No" answer for the specific level can be ascertained. This strategy can be used with an amplification/OSD combination, or to quantify LAMP. FIG. 39 shows that with a series concentration of false targets reacting with a certain amount of true target, the sharpest change of end-point fluorescence intensity happens when the amount of false target is equal to true target. Therefore, for an unknown sample, the series test with different amounts of false target gives quantification information at the sharpest change point of the end-point fluorescence intensity curve.

Based on the mechanism of fluorescence signal, as long as there is a blue light (approximately 470 nm, for example), a source, and with a long-pass filter (approximately 520 nm) or lens on the camera, a fluorescence photo can be captured for analysis. The fluorescence intensity and signal/background ratio can be adjusted for the best resolution by optimizing the components concentration in the LAMP-OSD. FIG. 38 shows the picture taken using an iPhone6 Plus with a Blue light transilluminator (Syngene, MD), which is for gel imaging; FIG. 40 shows a "black" box, with 9 v battery, and blue LEDs and orange gel filters, which can be used with smartphone imaging, for example. The results can be analyzed using computational analysis, for example.

8. OSD Design Rules for High Temperature Real-TimeReading

The regions (and their complementary region) between F1 and F2 (F1-F2), B1 and B2(B1-B2), F1 and B1c (F1-B1c) are all sequence-specific to the target (FIG. 1), which makes them useful as an OSD probing region. Referring to FIG. 1, the amount of single "loop region" (F1-F2, F1c-F2c, B1-B2, and B1c-B1c) is greater than the single "mid region" (F1-B1c and B1-F1c). Therefore, an OSD reporter can be designed to probe one or more of the loop regions in order to get a higher signal.

The optimized temperature for a LAMP reaction is between 60 and 65° C. In real-time reading mode, in order to keep the duplex region from denaturing and allow for toehold-binding to be strong enough for strand-displacement, the OSD was designed with a duplex region of 25 base pairs (the duplex region can vary in length by 1, 2, 3, 4, 5, 6, 7, 8, 9, or 10 bases, preferably 1-5 bases, more preferably 3 bases) and a toehold region of 11 bases (the length of the toehold can vary by 1, 2, 3, 4, 5, 6, 7, 8, 9, or 10 bases, preferably 1-3 bases, more preferably 2 bases). All of the templates tested with these metrics (GC ratio from 33% to 67%) were successfully amplified and detected.

In one example, the ΔG of the duplex region is kept below −18 kal/mol (calculated by NuPack, Caltech, CA) with 70 mM Na+, 4 mM Mg2+, at 60° C. For a template which is AT rich, it should be longer. The length of OSD can vary after optimization of the specific target for a better signal to background ratio, as described herein. Non-relevant base pairs can be added at the fluorophore/quencher end for a more stable duplex. For example, 1, 2, 3, 4, 5, 6, 7, or more non-relevant base pairs can be added at the end. In a preferred example, 3 base pairs can be added at the end. Another option to create a more stable duplex is to change the reaction temperature. For example, the reaction temperature can be below 65, 64, 63, 62, 61, 60, 59, 58, 57, 56, 55, 54, 53, 52, 51, or 50'C. Ina preferred embodiment, the reaction temperature can be 58° C. or lower.

If only an end-point signal (such as in a glucometer reading) is desired, then the duplex region and toehold length can be decreased. In this case, the length of the duplex region and toehold region can be varied according to the signal-reading temperature. One of skill in the art can determine how lengths can be varied based on signal reading temperature.

9. Kits

Disclosed herein are components useful with the methods disclosed herein. For example, the primers disclosed herein can be included in a kit. Also, the components needed to carry out a LAMP reaction, as well as OSD reporters, and any other compositions that are needed to carry out the methods, can be included in a kit.

Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, New York, 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their kd, or where only one of the nucleic acid molecules is 10 fold or 100 fold or 1000 fold or where one or both nucleic acid molecules are above their kd.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in □C or is at ambient temperature, and pressure is at or near atmospheric.

Figure 6A:
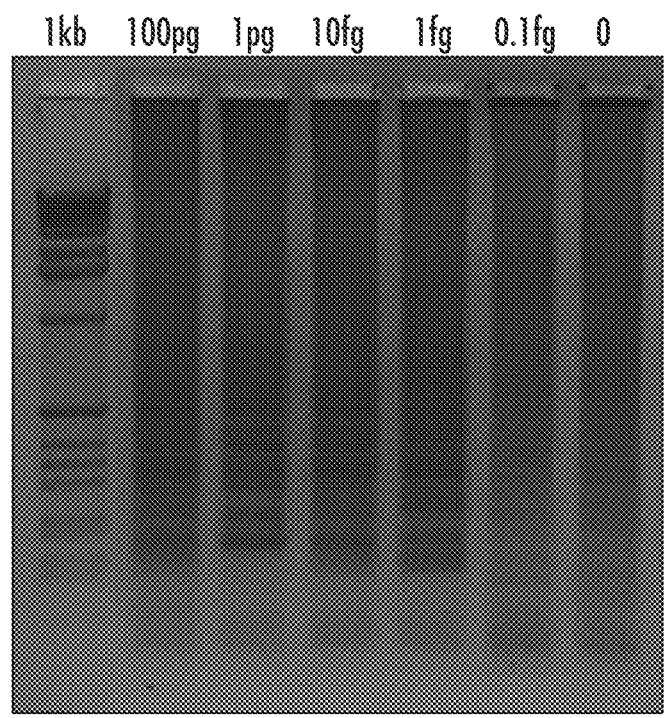
FIG. 6A shows LAMP with RPOB reaction characterized by Evagreen and electrophoresis gel comparisons.
Figure 6B:
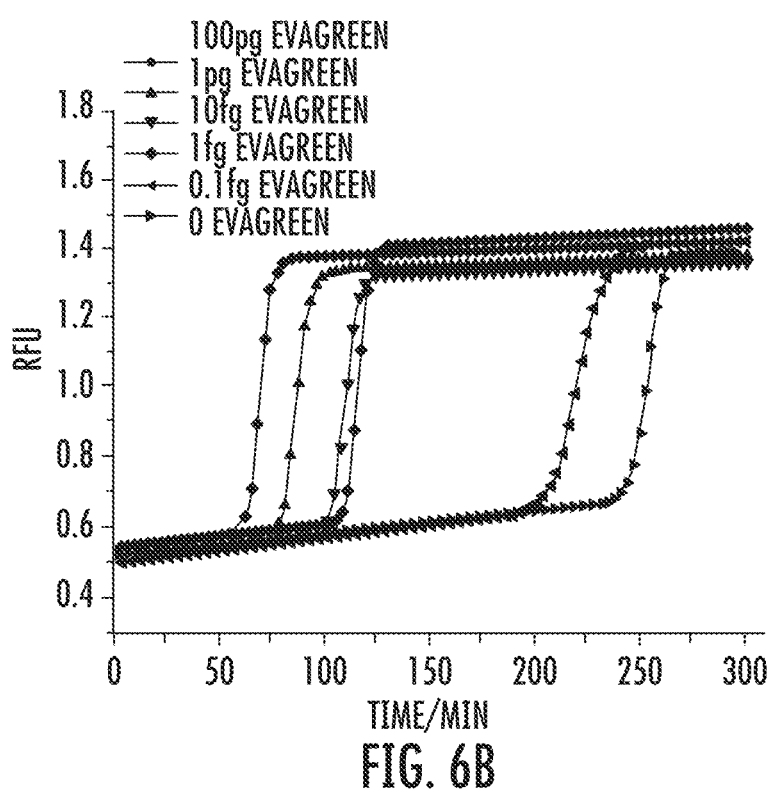
FIG. 6B shows that intercalating dye readout reveals dramatic increases in all of the samples, including the negative control.

Example 1: Toehold-Mediated Strand Exchange in Real-Time SNP Detection, Multiple Analysis, and Spiked Sputum Analysis with Loop-Mediated Isothermal Amplification Primer sequences were generated using PrimerExplorerV4 software. It is important to note that the sequence of the template can result in primers that inherently produce false amplicons. For example, the RPOB gene possesses a GC ratio of 64%, causing many of the primers to self-dimerize. Effects of this can be seen in FIG. 6, where the intercalating dye readout reveals dramatic increases in all of the samples, including the negative control. Similarly, in electrophoresis characterization (FIG. 2B and FIG. 6), both the negative control as well as low-concentration samples show evidence of amplified oligonucleotides of different lengths.

Figure 2A:
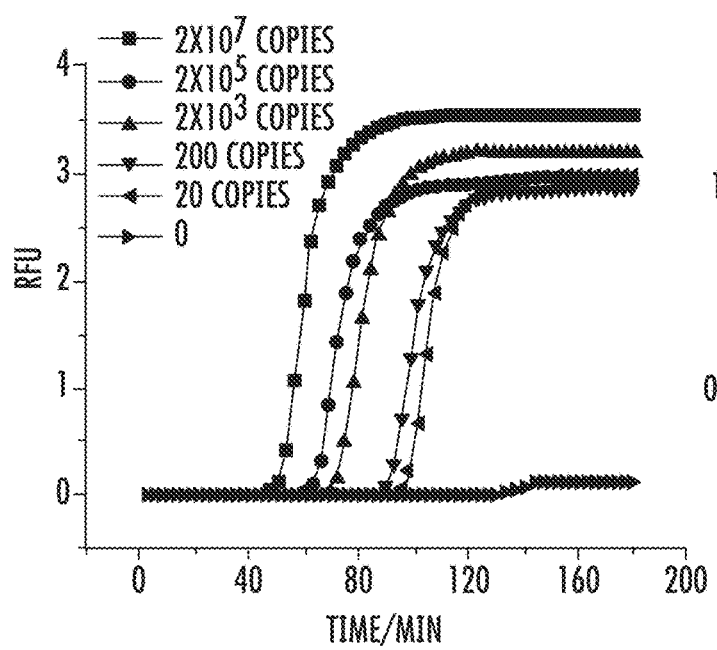
Figure 2B:
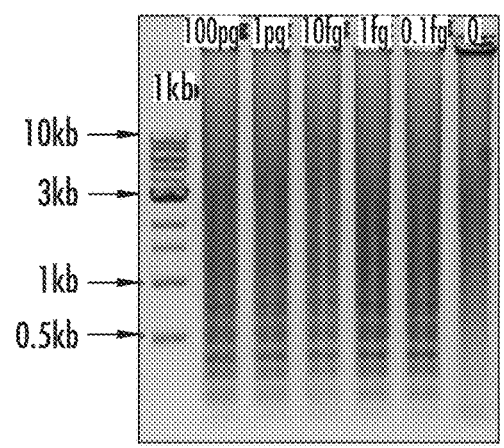

However, as seen in FIG. 1, the final LAMP product is comprised of large molecular weight concatemers, frequently containing free loops between the F1 and F2, B1 and B2, F1c and F2c, and B1c and B2c regions. These loops are independent of the primer sequences and unique to the template, thus OSD reporters were designed against these loops in order to discriminate true-positive amplicons. Take LAMP-OSD with RPOB for example: the Reporter F sequence was designed to be the complementary sequence of the region in between F1 and F2 (loop F) on the template; Reporter Q is a partial sequence of the same region. Therefore Reporter Q is kicked off by true-positive LAMP amplicons with the exact loop F sequence of the template. FIGS. 1 and 2 show the fluorescence signals from OSD reporters bound to the loop F sequences of RPOB and BRAF amplicons respectively. As seen in FIG. 2, results from LAMP-OSD with BRAF revealed a fluorescence curve shape that is quite similar to that of the intercalating dye (FIG. 6) except in the case of the negative control. While it is clear that some side-products were generated in the negative control (FIG. 2B), there was no reported fluorescence signal (FIG. 2A).

a) SNP Detection for BRAF Gene

Traditionally, real-time SNP discrimination of LAMP has been achieved by positioning the 3' end of a primer next to the mutated position. This method works by delaying amplification, which manifests as a shift in the Ct value. LAMP performed with lower concentrations of wild-type template however can present with nearly identical Ct value shifts, obfuscating SNP analysis. In light of this, an OSD reporter was designed such that the SNP was located in the middle of the toehold portion of the Reporter F strand, effectively inhibiting the binding of non-complementary amplicons (Li, B.; Ellington, A. D.; Chen, X. Nucleic acids research 2011, 39). Here, the BRAF V600E SNP was chosen as the target to demonstrate the SNP-discriminating capabilities of the LAMP-OSD system.

Figure 3:
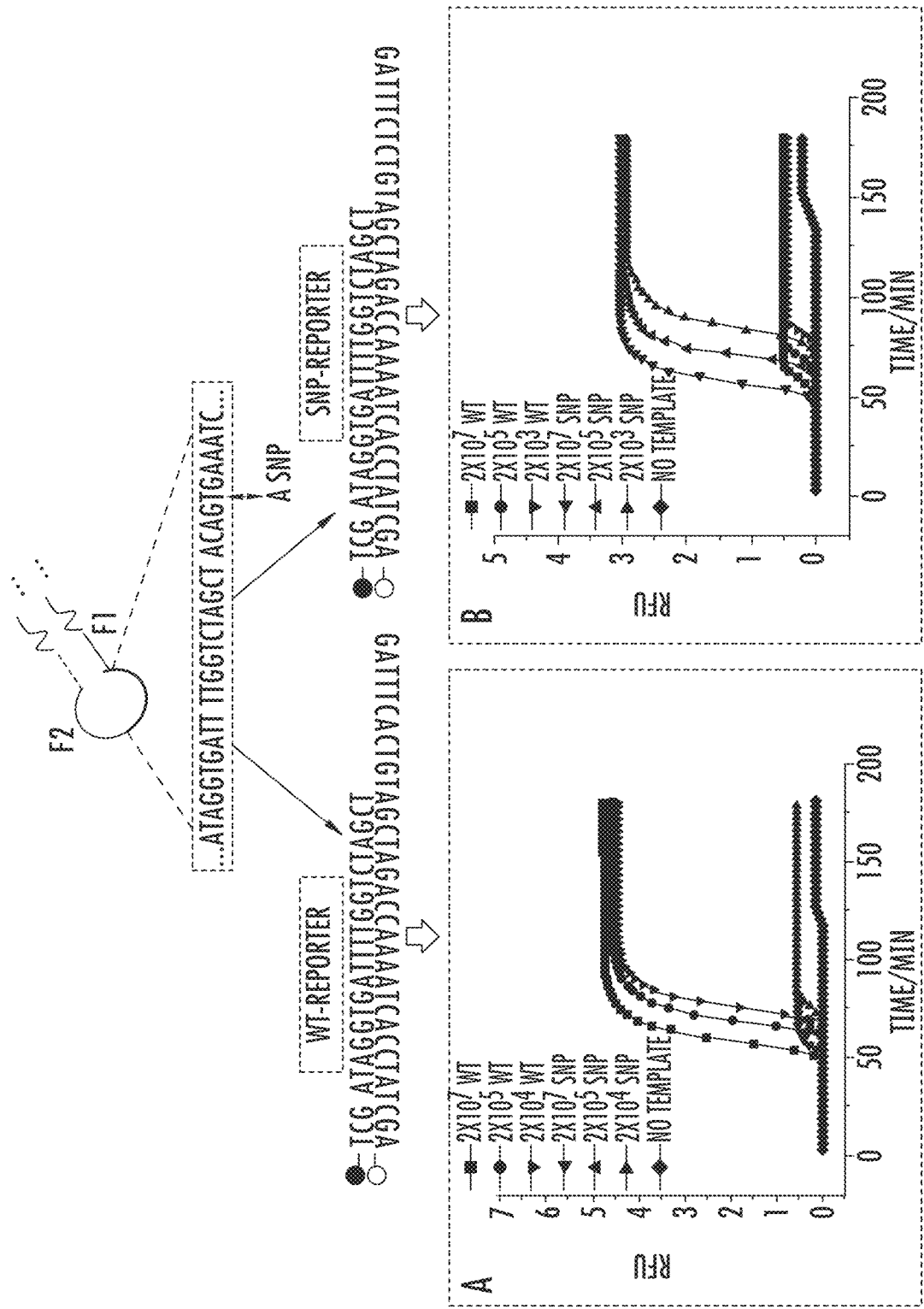

LAMP-OSD was performed with varying amounts of BRAF plasmid starting at a concentration of $2\times10^4$ copies (which is well above the limit of detection of ~20 copies at 60° C. (FIG. 2)). FIG. 3A results with the WT-reporter show that, in contrast to traditional SNP discrimination, this method produces clearly distinct fluorescence curves independent of concentration. In order to assure that these signal differences are not merely artifacts from using two different plasmids (WT and V600E), LAMP-OSD with a SNP-reporter was also performed. FIG. 3B demonstrates the inverted but proportional signal curves. [Traditional SNP detection methods have always struggled with limited R-values [concentration equivalence] (Chen et al. Nature Chemistry 2013, 5, 782). Note that R value denotes the excess of SNP target needed to yield the same level of fluorescence (50% of maximum) as that of the intended target at an equal concentration to that of the probe. An R-fold excess of the SNP target yields a false positive, so R determines the specificity of a diagnostic assay based on this technology, which reflect the relative difficulty of discriminating a SNP template compared to the relative ease of discriminating a WT template. This technique effectively combines real-time reading and kinetic toehold binding to separate the discrimination of the SNP and quantitative analysis into signal plateau and Ct value, separately.

Figure 7:
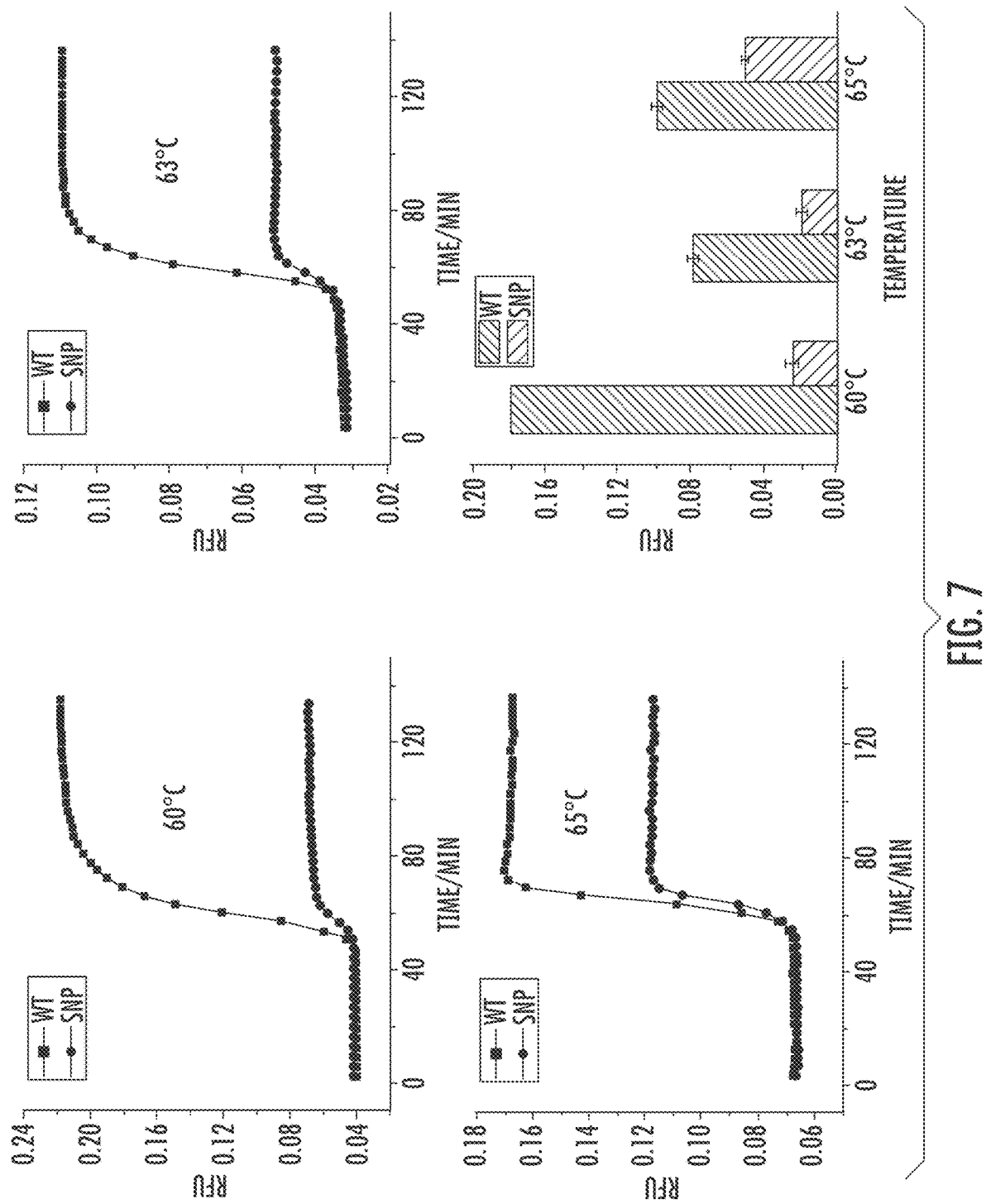
FIG. 7 shows 100 pg wildtype and SNP templates, which fluorescence response at different temperatures.

WT OSD detection can work robustly within the typical LAMP reaction temperature range, i.e. 55 to 65° C., as shown in FIG. 7. Results also show that lower LAMP temperatures are more favorable for SNP discrimination.

b) Multiplex Gene Analysis

Real-time methods for multiplex LAMP analysis offer several advantages to end-point analysis. Foremost of which, the two most common end-point methods found in literature—separation by agarose gel electrophoresis (Aonuma et al. Experimental parasitology 2010, 125, 179) and pyrosequencing (Liang et al. Anal Chem 2012, 84, 3758)— both involve post-processing that increases the chance of aerosolizing LAMP amplicons. In terms of real-time multiplex LAMP signal detection methods, most found in literature are based on fluorophore-labeled primers that yield signal upon amplification by various modes such as guanine quenching (Zerilli et al. Clinical Chemistry 2010, 56, 1287), and fluorescence resonance energy transfer between the fluorophore and an intercalating dye (Tanner et al. BioTechniques 2012, 53, 81), quencher strand displacement (DARQ system) (Kouguchi et al. Mol Cell Probe 2010, 24, 190). However, detection methods such as these, which rely on accumulation/loss of fluorescence signal from labeled primers during LAMP, are unable to distinguish amplicons resulting from non-specific priming. Alternatively, intercalating dyes such as EvaGreen may also be used for distinguishing various amplicons in multiplex LAMP reactions, but since such distinction is based on differences in the melting temperature (Tm) of the amplicons, nucleic acid targets with close or overlapping Tm cannot be effectively separated.

Figure 4:
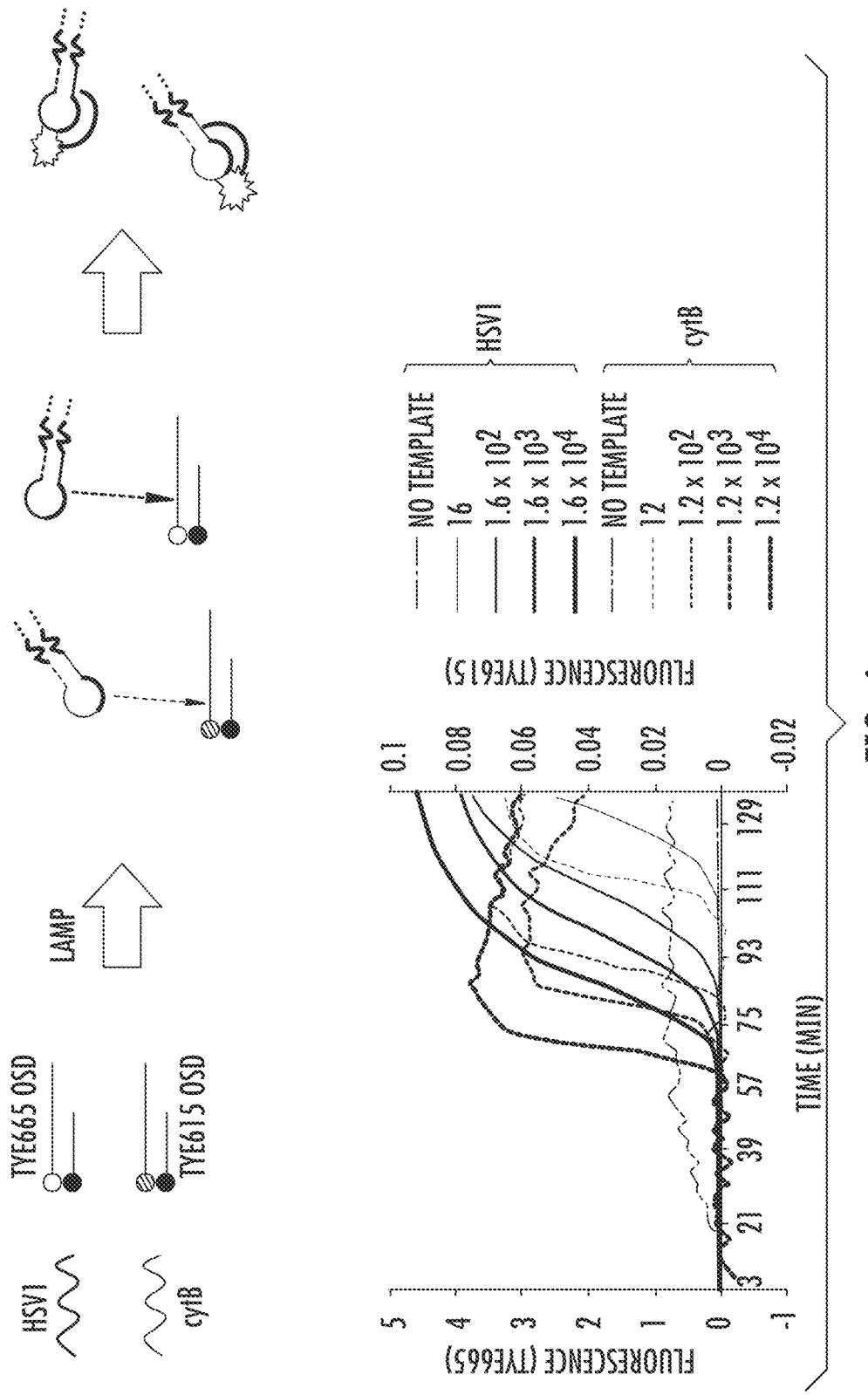

Due to the sequence-specific nature of their signal generation, OSD probes are ideally suited for the deconvolution of multiplex LAMP reactions. Cloned fragments of the *Plasmodium falciparum* cytB gene and the herpes simplex virus 1 (HSV1) US4 genomic locus using LAMP were co-amplified. HSV1-specific OSD probes labeled with the fluorophore TYE665 and cytB-specific OSD probes labeled with the fluorophore TYE615 were included in a multiplex, real-time LAMP reaction. As depicted in FIG. 4, OSD probes were able to detect LAMP amplicons originating from less than 20 copies of both the cytB and HSV1 synthetic targets. OSD probes allow unambiguous, sequence-based distinction of the individual components in a mixture in real-time. Moreover, multiplex analysis with OSD can also be designed to detect different regions of the same target, which provides an internal control for the analysis.

c) LAMP-OSD System in Detecting Synthetic Sputum Spiked with Different Amounts of MTB For any amplification method, the complexity of the sample, such as saliva or sputum, increases the risk of generating side-product or false negative result. This is particularly true of LAMP, which has more complex primer components than some other methods even before application to diagnostic samples. In order to test its robustness, LAMP-OSD system was applied to MTB-spiked sputum provided by PATH. This synthetic sputum contained a mixture of MTB bacteria, human genomic DNA, sperm DNA, mucin, and other components and served as a mimic of true patient samples. It was found that Bst 2.0 was greatly inhibited by mucin in the sample. Therefore, the mucin was liquefied with 2% freshly made N-acetyl-L-cysteine and 1% sodium hydroxide and lysed the sputum sample via 5 rounds of freezing and thawing. Assuming 100% recovery, three different RPOB gene doses were prepared with an estimated 1000 copies (HIGH), 100 copies (MED), and 10 copies (LOW) per LAMP reaction (25 μl). After adding each MTB-spiked sputum sample into a LAMP reaction mixture, the system was tested with 6 HIGH experiments, 6 MED, and 8 LOW. Each of the HIGH and MED experiments was positive for signal using the LAMP-OSD system (FIG. 8). Therefore LAMP-OSD appears most reliable for the detection of HIGH and MED-spiked samples.

d) CHA Coupling LAMP Reaction

Figure 5:
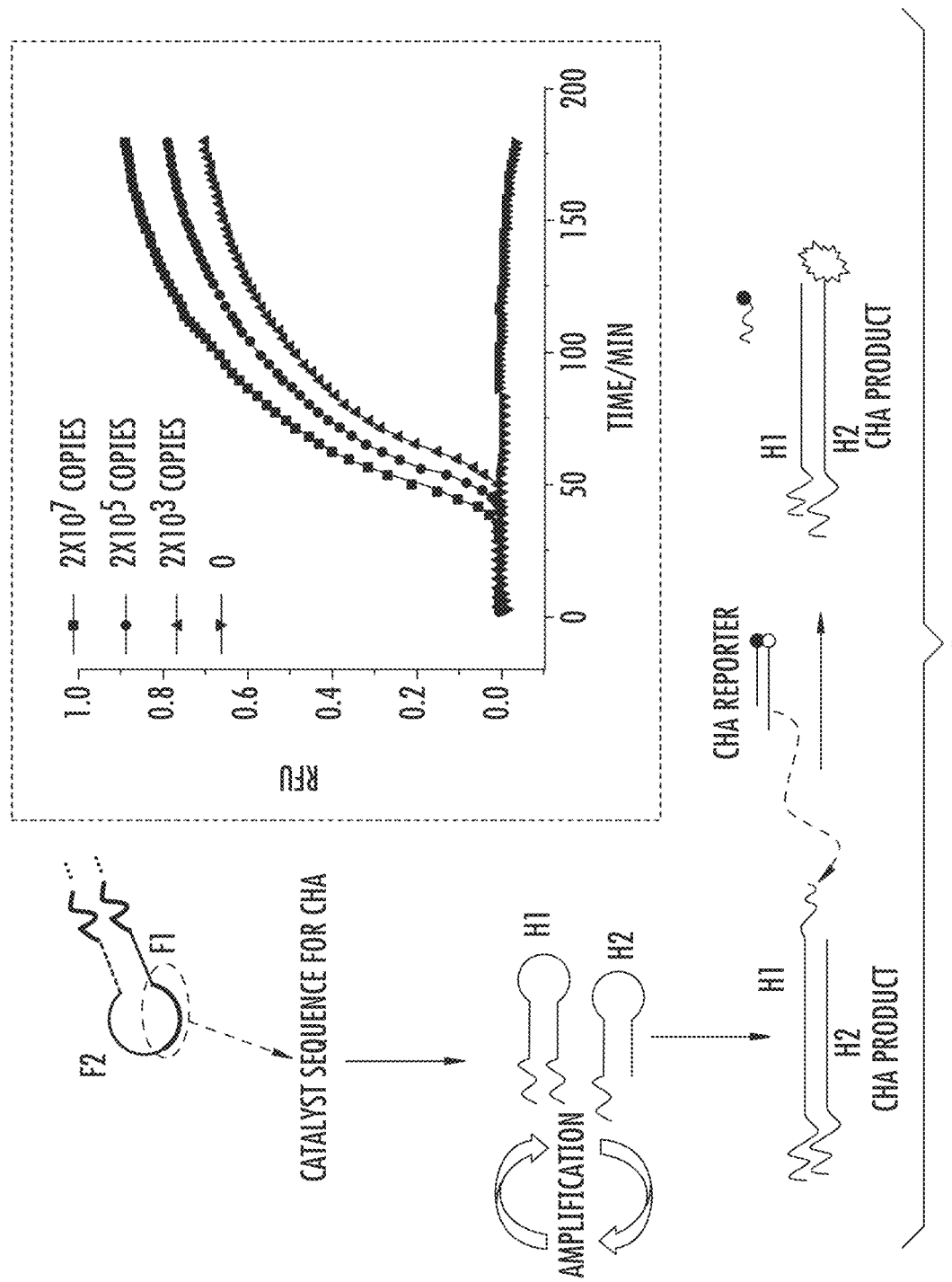

Catalytic hairpin assembly (CHA) can also serve as a real-time sequence-specific signal transducer of IsoT reactions, including rolling cycle amplification (Jiang et al. Journal of the American Chemical Society 2013, 135, 7430). Functioning as a nucleic acid amplifier circuit, CHA displayed robustness and programmability for diverse target sequences under varied buffer and temperature conditions without substantial decay in the signal-to-noise ratio. CHA circuits can transduce large LAMP amplicons into uniformly short CHA products. Moreover, CHA is readily adaptable to a variety of readout modalities (i.e. fluorimetry, colorimetry, electrochemistry) and platforms (paper-fluidics, for example, Allen et al. Lab on a Chip 2012, 12, 2951). Hence CHA was adapted for use in real-time LAMP reactions (FIG. 5).

Previously reported principles were used for the design of high temperature CHA in order to design a completely new circuit for RPOB (FIG. 9). LAMP-CHA fluorescence signals continuously increase.

e) Materials and Methods

Chemicals and oligonucleotides. All chemicals were of analytical grade and were purchased from Sigma-Aldrich (St. Louis, MO, USA) unless otherwise indicated. All oligonucleotides were ordered from Integrated DNA Technology (IDT, Coralville, IA, USA). Oligonucleotide sequences are summarized in Table 1.

Plasmids. *M. tuberculosis* rpoB gene segment was amplified by PCR using (i) Phusion DNA polymerase (New England Biolabs (NEB), Ipswich, MA, USA) from commercially available genomic DNA of the virulent strain H37Rv (ATCC, Manassas, VA, USA) and (ii) gene-specific primers. The *Plasmodium falciparum* cytB and the human v-raf murine sarcoma viral oncogene homolog B1 (BRAF) gene segments were built from synthetic oligonucleotides by overlap PCR using Phusion DNA polymerase. SNP-containing alleles were built by overlap PCR amplification of the wildtype gene segments using site-specific mutagenic primers. The PCR products were purified from agarose gels using the Wizard SV gel and PCR purification system (Promega, Madison, WI, USA). The PCR products were then inserted into the pCR2.1TOPO plasmid (Life Technologies, Grand Island, NY, USA) by either Gibson cloning using a commercially available Gibson master mix (NEB) or by TA cloning (Life Technologies). All plasmids used in this study were verified by sequencing at the Institute of Cellular and Molecular Biology Core DNA sequencing facility.

Standard LAMP reaction. Mixtures containing template, 0.8 μM each B1c-B2 and F1c-F2, 0.2 μM each B3 and F3, 1 M betaine, and 0.4 mM dNTPs in a total volume of 24 μL 1× Isothermal Buffer (20 mM Tris-HCl, 10 mM (NH4)2SO4, 10 mM KCl, 2 mM MgSO4, % Triton X-100, pH 8.8) were heated to 95° C. for 5 to 10 min, followed by chilling on ice for 2 min. Then, 1 μL (8 U or 60 U) of Bst polymerase 2.0 was added to initiate the LAMP reaction. The reactions (with a final volume of 25 μL) were incubated at 65° C. or 60° C. for 3 hs, in the thermal cycler.

Multiplex LAMP reaction. Various copy numbers of each target were spiked separately into TE buffer (10 mM Tris-HCl pH 7.5, 0.1 mM EDTA pH 8.0) containing 1.1 ng/μl of human genomic DNA (Promega, Madison, WI, USA). Standard 25 μl LAMP reactions were then set up separately for different copy numbers of each target. Multiplex LAMP reactions in μl volumes were then assembled by mixing 20 μl of each HSV1 LAMP reaction with 15 μl of the cytB LAMP reaction with the corresponding equal template copy number. This relative ratio of HSV1:cytB was chosen after optimization experiments. The effective concentration of reagents in the final multiplex LAMP reaction are: 0.46 μM each of HSV1 FIP and BIP, 0.11 μM each of HSV1 F3 and B3, 0.34 μM each of cytB FIP and BIP, 0.086 μM each of cytB F3 and B3, 0.4 mM dNTPs, 1 M betaine, 1× isothermal buffer, 2 mM MgCl2, 28 nM HSV1 TYE665-labelled probe (pre-annealed with a 5-fold excess of the quencher strand), 21 nM cytB TYE615-labelled probe (pre-annealed with a 5-fold excess of the quencher strand) and 8 units of Bst 2.0 DNA polymerase. LAMP reactions were amplified at 65° C. in the LightCycler96 real-time PCR machine (Roche) and fluorescence was measured every 3 min in the Texas Red (for TYE615) and cy5 (for TYE665) channels. The fluorescence data was analyzed for 'Absolute quantification' using the LightCycler96 software and plotted against amplification time Coupling LAMP to OSD fluorescence detection. OSD stock solution was prepared with 10 uM Reporter F/50 uM Reporter Q, followed by heating to 95° C. for 5 min and slowly cooling to room temperature at a rate of 0.1° C./s in isothermal buffer. The LAMP+OSD reaction was prepared almost as the same to the standard LAMP reaction, except Multiple detection was the almost the same preparation, but with multiple sets of primer and reporters added with the same final concentration.

f) Electrophoresis Analysis of LAMP Reaction by Agarose Gel.

A 20 µL system with the varying concentrations of circular DNA chosen for this experiment, 100 nM primer, 0.4 U/µL Bst, and 1 µM InvtdT in the 1×ThermoPol reaction conditions was incubated at 60° C. for 3 h followed by 15 min of incubation at 80° C. After this reaction the sample was kept at 4° C. until electrophoresis. Each electrophoresis experiment was carried out with a 1% SeaKem® LE agarose gel. Each well had 10 µL of sample and an additional 2 µL 6×Orange loading dye for a total 12 µL system.

TABLE 1

Sequences

| Name | | Sequence (5'-3') | Notes |
|---|---|---|---|
| RPOB primers | FIP | CTTGATCGCGGCGACCACCG-AGCGGATGACCACCCA (SEQ ID NO: 1) | |
| | BIP | CAGCCAGCTGAGCCAATTCATGGACCA-GACAGTCGGCGCTTGTG (SEQ ID NO: 2) | |
| | F3 | GCATGTCGCGGATGGAG (SEQ ID NO: 3) | |
| | B3 | CGCTCACGTGACAGACCG (SEQ ID NO: 4) | |
| RPOB OSD reporter | Reporter F | /56-FAM/CGA CGTGGAGGC GATCACACCG CAGACGTTGA/3InvdT/ (SEQ ID NO: 5) | Only oligos in the real-time reading system will be modified with /3InvdT/ |
| | Reporter Q | C GGTGTGATC GCCTCCACG TCG/3IABkFQ/ (SEQ ID NO: 6) | |
| BRAF primers | FIP | ACTGATGGGACCCACTCCATAAGACCTCACA GTA AAAATA (SEQ ID NO: 7) | |
| | BIP | AACAGTTGTCTGGATCCATTTTGTGACATCTG ACT GAAAGCTGTA (SEQ ID NO: 8) | |
| | F3 | CCACAGAGACCTCAAGAGT (SEQ ID NO: 9) | |
| | B3 | ACAGAACAATTCCAAATGCATAT (SEQ ID NO: 10) | |
| BRAF OSD reporter | (WT) Reporter F | GAT TTC ACT GTA GCT AGA CCA AAA TCA CCT ATC GA/36-FAM/ (SEQ ID NO: 11) | Only oligos in the real-time reading system are modified with /3InvdT/ |
| | (WT) Reporter Q | /5IABkFQ//TCG ATA GGT GAT TTT GGT CTA GCT/3InvdT/ (SEQ ID NO: 12) | |
| | SNP Reporter F | GAT TTC TCT GTA GCT AGA CCA AAA TCA CCT ATC GA/36-FAM/ (SEQ ID NO: 13) | |
| | SNP Reporter Q | /5IABkFQ//TCG ATAGGTGATT TTGGTCTAGCT/3InvdT/ (SEQ ID NO: 14) | |
| RPOB CHA | H1 | CGTGGAGGC GATCACACCG CAGACGTTGA CCACGCTGCTAGCA TCAACGTCTG CGGTGTGATC CCTTGTCA TACGCAGCAC/3InvdT/ (SEQ ID NO: 15) | Only oligos in the real-time reading system will be modified with /3InvdT/ |
| | H2 | CAGACGTTGA TGCTAGCAGCGTGG TCAACGTCTG CGGTGTGATC CCACGCTGCTAGCA/3InvdT/ (SEQ ID NO: 16) | |
| | Reporter F | /56-FAM/CGA GTGCTGCGTA TGACAAGG GATCACACCG/3InvdT/ (SEQ ID NO: 17) | |
| | Reporter Q | C CCTTGTCA TACGCAGCAC TCG/3IABkFQ/ (SEQ ID NO: 18) | | for that the OSD reporter (with a final concentration of 60 nM) was added after the heat-chilling and before the Bst 2.0. 20 uL of LAMP OSD solution was added in 96-well plate and fluorescence signal was measured with Light Cycler 96 (Roche, US) at 60° C. or 65° C. for 3 hours.

g) Synthetic Sputum and its Pretreatment:

The sputum was provided by PATH. In detail, the synthetic sputum was made according to the constituents described in Sanders, et al, Am J Respir Crit Care Med, 164: 486-93, 2001 and consists of 47 mg/mL porcine mucin, 6 mg/mL salmon sperm DNA, 3.6 mg/mL phosphatidylcholine and 33 mg/mL bovine serum albumin in 114 mM NaCl, 2 mM sodium azide. Components were mixed to obtain a uniform slurry and defined numbers of mycobacterium (MTB) added and further mixed overnight at 4° C. prior to aliquoting.

(1) Pretreatment 500 uL aliquots from each sample were thawed and the mucin liquefied with 2% freshly made N-acetyl-L-cysteine and 1% sodium hydroxide for 15 minutes at room temperature. Following digestion the contents were diluted 50-fold with phosphate buffered saline and centrifuged at 3000×g for 20 minutes and the supernatant discarded. The resulting pellet was resuspended in 300 μL TE buffer (10 mM Tris, 1 mM EDTA, pH 8.0). The resulting solution was treated with freezing at −80° C. and thawing at 95° C. for 5 times before centrifuge at 1600 rcf for 10 min. The resulting supernatant is directly used in the RT-LAMP OSD detection.

Different Amount of the Spiked Samples (Table 2):

| Different spiked samples | Cells number in each spiked sputum |
|---|---|
| TB_Sputum_HIG(HIG) | $1 \times 10^5$ cells/ml |
| TB_Sputum_MED(MED) | $1 \times 10^4$ cells/ml |
| TB_Sputum_LOW(LOW) | $1 \times 10^3$ cells/ml |
| TB_Sputum_NEG(NEG) | synthetic sputum only |

(2) Lamp Reaction:

All the real-time LAMP reaction was conducted in Light Cycler 96 (Roche, US). The experiment setup was 2-step amplification and temperatures of this two step is the same, either 60° C. or 65° C.

(3) With Evagreen as Indicator

A 25 ul LAMP mixture was comprise of 800 nM FIP, 800BIP, 200nMF3, 200 nM B3, 1× Evagreen dye, 8 U or 60 U of Bst.2.0 polymerase, different amount of template, 1× Isothermal buffer, 1M Betaine, and 400 uM dNTP. The mixture was heated at 95° C. for 2 min then chilling down on ice for 2 min before adding the Bst.2.0 and placed into the light cycler.

(4) With OSD as Indicator

A 25 μl LAMP mixture was comprised of 800 nM FIP, 800BIP, 200nMF3, 200 nM B3, 1× Evagreen dye, 8 U or 60 U of Bst.2.0 polymerase, different amount of template, 1× Isothermal buffer (20 mM Tris-HCl 10 mM (NH4)2SO4 50 mM KCl 2 mM MgSO4 0.1% Tween® 20 pH 8.8@25° C.), 2 mM MgCl2, 1M Betaine, 400 uM dNTPs and 60 nM OSD reporter. The mixture was heated at 95° C. for 2 min then chilling down on ice for 2 min before reporter and Bst.2.0. 20 ul well mixed solution was then placed into the light cycler. The OSD reporter solution was prepared by mixing 10 uM Reporter F and corresponding 50 uM Reporter Q and annealed at 95° C. for 5 min and cooled down to 25° C. with a rate of 0.1° C./s.

(5) Agarose Gel Electrophoresis:

After the LAMP reaction the sample was kept at 4° C. until electrophoresis. Each electrophoresis experiment was carried out with a 1% SeaKem® LE agarose gel. 0.5 ug NEB 1 kb ladder was used here as the DNA ladder. Each well had 5 uL of sample and an additional 1 μL 6×Orange loading dye for a total 6 μL system. The electrophoresis was conducted at 110 to 120 Volt for 30 min.

(6) OSD Reporter Design:

(a) Probing Region

The probing region (as shown in FIG. 1) is the loop that irrelevant to primer sequence, which is located in between the F2 and F1, B2 and B1, F2c and F1c, or B2c and B1c region. Four of the loop regions in the FIG. 1 are all available to be used as the probing region. The loop region in between F2 and F1 for RPOB and BRAF was used.

(b) Length Picked Up

The Reporter F was designed to be completely complementary to the probing region, and the Reporter Q was partly hybridized with Reporter F. The length of the Reporter F and Q was designed according to their ΔG<=−18 kcal/mole at 60° C. with salt concentration of the isothermal buffer. Toehold length was designed as 10.

Example 2: MERS Point-of-Care Diagnosis: Coupling Isothermal Amplification Via DNA Transduction to Glucometers The middle-east respiratory syndrome coronavirus (MERS-CoV) belongs to human betacoronavirus family of coronaviruses which are large positive-stranded RNA viruses whose genomes typically range between ~27 to ~31 kb in size. The first case of MERS-CoV infection was identified in 2012 in a Saudi Arabian patient who died from a severe respiratory illness. (Zaki et al. New Engl J Med 367, 1814-1820, (2012); Holmes, Lancet 383, 1793-1793, (2014); Cotten, M. et al. Lancet 382, 1993-2002(2013)). Since then, the infection has spread globally and through May of 2014 has caused 614 laboratory-confirmed cases with 181 deaths (Holmes et al; Update: Recommendations for Middle East Respiratory Syndrome Coronavirus (MERS-CoV). Mmwr-Morbid Mortal W 62, 557-557 (2013); Bialek, S. R. et al. May 2014. Mmwr-Morbid Mortal W 63, 431-436 (2014)). Such a rapid infection frequency and high death rate has made MERS-CoV one of the most serious viral pathogens to emerge world-wide since SARS-CoV (Coleman, C. M. & Frieman, M. B. J Virol 88, 5209-5212, (2014)). In order to control the infection and receive timely treatment, selective distinction of MERS-CoV for early clinical diagnosis is extremely important. Increasing efforts have been made to this end, using methods such as immunofluorescence assays (targeting MERS-CoV N and S proteins) (Corman, V. M. et al. Eurosurveillance 17, 2-10 (2012)) and real-time reverse transcription polymerase chain reaction (RT-PCR, targeting viral genes in or around ORF1A, ORF1B and upE) to realize both qualitative and quantitative detection (Corman, V. M. et al. Eurosurveillance 17, 3-8 (2012); Fauci, A. S. Nat Rev Drug Discov 7, 12-12, (2008) Corman, V. M. et al. J Clin Virol 168-171, (2014)).

To meet the need for a low-cost, ultra-sensitive, POC assay for MERS-CoV, the sensitivity of loop-mediated isothermal amplification (LAMP) with specificity of sequence-specific nucleic acid strand displacement signal transduction was combined. By using 4-6 different oligonucleotide primers specifically designed to recognize 6-8 distinct regions on the target gene, the LAMP reaction can amplify the target sequence up to $10^{10}$ fold in a 10 min to two hour isothermal reaction (Notomi, T. et al. Nucleic Acids Res 28, (2000); Nagamine, Biochem Bioph Res Co 290, 1195-1198, (2002)). It, therefore, can provide ultra-sensitivity and fast reaction time without the need for a thermo-cycler. Compared to many other isothermal amplification methods (Guatelli, J. C. et al. P Natl Acad Sci USA 87, 1874-1878, (1990); Compton, J. Nature 350, 91-92, (1991); Hall, Biotechniques 32, 604-+ (2002); Walker, G. T. et al. Nucleic Acids Res 20, 1691-1696, 1992); Dean, F. B. et al. P Natl Acad Sci USA 99, 5261-5266, (2002); Vincent et al. Embo Rep 5, 795-800, (2004); Kurn, N. et al. Clin Chem 51, 1973-1981, (2005)), LAMP has the added advantages of 1) using only one enzyme, 2) both DNA and RNA can be amplified and 3) it produces a lot of single strand loops. This last advantage is especially important because it makes LAMP friendlier for sequence-specific downstream readout systems, which can help to reduce the risk of misreading induced by easily produced off-target false-positive amplicons. This has been well-proven in studies which used sequence-specific nucleic acid strand exchange reactions as either end-point or real-time transducers for LAMP reactions, followed by the generation of easily detectable fluorescence outputs. Self-designed asymptomatic primer sets for reverse transcription LAMP (RT-LAMP) reactions targeting MERS-CoV genomic loci located within the ORF1A and ORF1B genes and upstream of the E gene (upE), respectively, were used. The respective loop product triggers a one-step strand displacement reaction (OSD) to displace a quencher-labeled strand away from a carboxyfluorescein (FAM)-labeled strand, leading to increased fluorescence for real-time verification of real MERS-CoV amplicons. The resulting assays could detect 0.02 to 0.2 plaque forming units (PFU) (5 to 50 PFU/ml) of MERS-CoV in infected cell culture supernatants within 30 to 50 min and did not cross-react with common human respiratory pathogens.

The fluorescence signal output was replaced with a different detection system. This is necessary because fluorescence emission requires complex instrumentation and is environmentally unstable. Herein, LAMP/RT-LAMP was coupled via OSD to commercial blood glucometers, for the first time enabling viral (MERS-CoV) detection and diagnosis on a fieldable detection platform. The results demonstrated the LAMP-OSD-Glucometer combination (LOG) could provide outstanding reliability, reproducibility and a simple "YES-or-NO" answer in both end-point and real-time strategies during targeting the MERS ORF1A region, without losing sensitivity compared the previously reported fluorescence assay. The use of an OR GATE design by probing both ORF1A and upE further guaranteed a fail-safe assay. The "sweet spot" therefore shows a ready-to-use MERS-CoV POC detector that deserves intensive interest for immediate instrumentation (device) and optimization. The LAMP-OSD-Glucometer Platform concept has also proven to be very compatible to a wide range of temperatures, operating times and reaction volumes, which is applicable to the analysis of a wide variety of other disease causing agents and biomarkergenes.

a) Results (1) Principle of LAMP-OSD-Glucometer Platform Sensing Platform and Three Detection Strategies The whole sensing process is broken into four steps (FIG. 12) and summarized in FIG. 20.

LAMP Reaction. A standard LAMP/RT-LAMP reaction is carried out to produce flower-like amplicons including four kinds of single strand loops positioning between F2-F1 (F-target), F2c-F1c (F-probe), B2-B1 (B-probe), and B2c-B1c (B-target), respectively.

One step strand displacement and magnet separation. Loop amplicons, here containing F-target (domain 2-1), binds the domain 1* on FP (labeled on streptavidin-magnetic beads through biotin) as a toehold and starts a one-step toehold mediated strand displacement reaction (OSD) to displace invertase-labeled FPc (domain 2, Inv-FPc) away from FP. The displaced Inv-FPc is thus released into solution after a simple magnetic separation. The whole of step II is abbreviated as OSDS.

Glucose generation. The released Inv-FPc is mixed with sucrose, which catalyzes the hydrolytic cleavage of the disaccharide sucrose into the monosaccharides glucose and fructose.

Glucometer reading. The resulting glucose is then detected by using any commercial blood glucose meter.

The four-step LAMP-OSD-Glucometer platform shown above has been proven applicable to both end-point and real-time assays (FIG. 20). "End-point" means that LAMP and OSDS happened in different reservoirs in a sequential manner. In all of our end-point experiments, the LAMP reaction step (Step I) and glucose generation step (Step III) were kept at 55° C. to maintain relatively high activities of both steps. And OSDS step (Step II) was done at either 25° C. (Strategy 1) or 55° C. (Strategy 2). "Real-time" means that LAMP and OSDS were performed simultaneously in the same reservoir. This real-time strategy (Strategy 3) was carried out at 55° C. The glucometer reading step (Step IV) for all three strategies was carried out at 25° C. In the following several sections, proof-of-concept results relevant to the three strategies are shown in detail, demonstrating the LAMP-OSD-Glucometer sensing platform is ultra-sensitive-selective, and -flexible. But for convenience, in most experiments, 25° C. OSDS (Strategy 1, FIG. 20) was used as a model strategy.

b) Sensitivity and Selectivity Tests Using 25° C. OSDS (Step II) as Model (Strategy 1)

After the OSDS step performance of the assay was confirmed by detecting a linear DNA (1A-T) with the same sequence as F-target (domain 2-1) produced after LAMP reaction, initially PCR-generated DNA from a segment of MERS-CoV genome (corresponding to portions of sORF1A) was used as the LAMP input to test the plausibility, sensitivity, and selectivity of the LAMP-OSD-Glucometer sensing platform. As mentioned above, Strategy 1 with 25° C. OSDS was adapted here.

FIG. 21A indicates that when compared with the pure negative control (isothermal amplification buffer with no sORF1A), samples with different copies of sORF1A all produced at least 35 mg/dl or higher glucometer signals. The dose indiscrimination was due to the fact that with the rationally designed primer and enough time (1.5 hour here), LAMP reactions with different amounts of sORF1A would consume the primers and produce similar amounts of loop products. This was consistent with the agrose electrophoresis results (FIG. 21B). Because there was always a big gap/amplitude (~35 mg/dl) between "sORF1A positive response (signal)" and "off-target negative control (background)", the LAMP-OSD-Glucometer platform can provide very sensitive "YES-or-NO" answer, with a reproducible recognition limit down to 20 copies. Meanwhile, the high selectivity for both LAMP primers (called ORF1A. 55) and the whole LAMP-OSD-Glucometer platform was confirmed by using another set of negative controls. As shown in FIG. 21, in presence of the ORF1A.55 primer set, as high as 7E5 copies of PCR product amplified from rpoB genome segment (for *Mycobacterium tuberculosis*, shortened as RPOB) did not result in the production of LAMP amplicons (FIG. 21B, N-2) nor a detectable glucometer signal over background (FIG. 21A, N-2). Even if the primers were specifically designed for RPOB which would lead to the production of a massive number of LAMP amplicons (FIG. 21B, N-3), the resulting amplicons could only produce a little detectable increased glucometer signal over background (FIG. 21A, N-3). There was still at least 30 mg/dl less than "sORF1A positive responses". These results demonstrated that neither non-relevant templates nor non-relevant LAMP products would produce false positive response.

Further demonstration for the high performance of the LAMP-OSD-Glucometer sensing platform was realized by directly detecting RNA extracted from tissue cultures grown with MERS-CoV virions (MERS-CoV RNA, FIG. 22). In this assay, reverse transcription LAMP (RT-LAMP) was adapted instead of regular LAMP. Detection results shown in FIGS. 22A and 22B (Strategy 1) were very consistent with those for the PCR product of sORF1A. After these results, an invertase derived from the hyperthermophilic bacteria, *Thermotoga maritima*, was used. Since this invertase (Tm-INV) was derived from a hyperthermophile, both its activity and its structural stability was hypothesized to be increased relative to the yeast invertase, especially at the elevated 55° C. assay temperature used for the LAMP step. Improvement in stability and kinetics at elevated temperatures has been observed for other thermophilic enzymes.

Employing this novel invertase and performing the detection assay using the current experimental conditions, showed that the TmINV did behave better in terms of both thermo-stability and enzymatic activity when compared to the mesophilic yeast invertase. With TmINV the resulting assays were able to detect as low as 0.1 plaque forming units (PFU) (25 PFU/ml) of MERS-CoV in infected cell culture supernatants within 1.5 hour LAMP reaction. Assays performed from much shorter LAMP reactions (eg. 10 min) suggested even though the overall signal intensity of both the negative and positive controls would be slightly decreased, the signal-to-noise ratio was sufficient for a "YES-or-NO" answer.

c) Reproducibility and Stability Tests for the Inv-FPc/F-Probe/MBs

In the LAMP-OSD-Glucometer sensing platform, the preparation and storage of the Inv-FPc/FP duplex modified magnetic beads (Inv-FPc/FP/MBs) is very important to ensure the reliability of the assay. The reproducibility and stability for these beads was tested, using Strategy 1 as model. The reproducibility test was carried out through comparing three parallel assays (in the same day) using Inv-FPc/FP/MBs prepared on three consecutive days, respectively (Strategy 1). As expected, very small deviations were seen between all nine sets of measurements for either "sORF1A positive samples (2E4 copies)" or "buffer negative controls". In particular, the standard deviations of using preparations of Inv-FPc/FP/MBs from different days was only 1.26 mg/dl and 4.37 mg/dl for negative and positive responses, respectively, both of which were below 6% of respective average signal. The stability of Inv-FPc/F-probe/MBs was also tested by measuring "sORF1A positive samples (2E4 copies)" every 2 to 20 days (Strategy 1) using the Inv-FPc/FP/MBs prepared on the same day. FIG. 22B demonstrated that their high performance could keep at least 60 days (when stored at 4° C.). And neither changing Inv-FPc/FP/MBs (red dot on day-2) nor changing LAMP amplicons (purple and blue dots on day-22 and day-60) could induce larger signal deviations during this 60-day period. The results shown above successfully verified the stability and reproducibility of the Inv-FPc/FP/MBs, and correspondingly, the good performance of the whole LAMP-OSD-Glucometer sensing platform.

d) Realization of 55° C. OSDS (Strategy 2) and Real-Time Assay (Strategy 3)

Besides the 25° C. OSDS (Strategy 1), the other end-point detection strategy with ° C. OSDS (Strategy 2, FIG. 21) and real-time detection strategy (Strategy 3, 55° C. LAMP and OSDS, FIG. 21) were also carried out for MERS-CoV RNA to show the superior flexibility of the LAMP-OSD-Glucometer sensing platform. Strategy 2 and 3 kept the same sensitivity as Strategy 1, but with higher background (off-target negative control). Comparison between the three detection strategies showed that to produce similar signal gap/amplitude (Signal-Background or ΔSignal) as seen in Strategy 1, 11 min and 15 min reaction times for glucose generation (Step III) was required for Strategies 2 and 3 (FIG. 24, left y-axis, rectangle), respectively. Both were much shorter than what was required by Strategy 1 (23 min). However, the Signal-to-background ratio (Signal/Background) was less in Strategy 2 and 3. That makes sense because the Kd of DNA duplex is increasing at the higher temperature (eg. 55° C.), thus releasing more Inv-FPc into the solution even without the target. Such relatively high background leakage may be further minimized through optimizing the lengths of DNA probes and the other experimental conditions.

e) Design of Fail-Safe OR GATE Sensing Platform

An OR gate was designed that could respond to LAMP products amplified from either ORF1A region or upE region on MERS-CoV RNA. Briefly, F-target DNA loop amplified from ORF1A region (1A-F-target) and upE region (upE-F-target) could trigger a toehold mediated strand displacement to, respectively, displace Inv-1A-FPc and Inv-upE-FPc away from OR-P attached to the magnetic beads (FIG. 15A). Such a design scheme makes sure a "fail-safe" detectable signal was observed even if one of the two LAMP amplifications did not happen. upE-T and 1A-T, two linear oligonucleotides with same sequences to upE-F-target and 1A-F-target, were used as model inputs to test the OR gate design. As shown in FIG. 15B. 500 nM upE-T (1,0) or 500 nM 1A-T (0,1) could provide very similar positive response (1), ~100 mg/dl higher than buffer negative control (0,0) signal. And as expected, existence of both 500 nM inputs (1,1) could almost double the positive signals, indicating their equal strand displacement efficiency to Inv-1A-FPc and Inv-upE-FPc, respectively. It also shown that beyond fail-safe detection, the OR gate can also function as a signal amplifier. Similar phenomenon was observed when it was switched to the real MERS-CoV RNA as input (FIG. 15C). For convenience, the inputs of buffer negative control, upE-F-target only, 1A-F-target only, and upE-F-target& 1A-F-target were prepared by using no primer, upE primer (upE.9) only, 1A primer (ORF1A.55) only, and upE.9& ORF1A.55 to trigger the LAMP reactions containing the same amount of MERS-CoV RNA (2.5E5 PFU/mL), respectively.

f) Discussion

The use of a commercial blood glucometer to realize MERS-CoV virus detection, by employing an isothermal amplification and DNA strand exchange signal transduction scheme, is shown herein. In the whole sensing process, the sensitivity was mainly provided by the powerful signal amplification properties of LAMP, while the selectivity was provided by both the LAMP primers and the strand displacement reaction. It has been shown that the OSD reaction could happen either at 25° C. or 55° C. Actually, when adapting end-point strategies, any temperature between these 25° C.-55° C. could be reasonably suitable to a real-world operation, without changing FPc and FP sequences. Meanwhile, as summarized in Figure reaction times and volumes for each step may be variable in a wide range. For example, the total detection time could be as short as 23 min, and the total volume could be as small as μL. These results have provided very convincible data to prove the super flexibility of the LAMP-OSD-Glucometer sensing platform. In other words, LAMP-OSD-Glucometer sensing platform can be made to fit many kinds of micro-fluidic or one-pot device designs.

Recently publications suggested that indirect immuno-fluorescence of viral loads in a patient were published to be as high as $1-2\times10^6$ copies per ml in the lower respiratory tract, 2691 RNA copies per mL of urine, 1031 viral RNA copies per gram of stool and 5370 copies of viral RNA per mL of an oronasal swab. Even the number in oronasal swab is much less compared with in blood and urine, based on these results the LAMP-OSD-Glucometer sensing platform is sensitive enough to meet such high sensitivity requirements.

g) Conclusion

Herein, both end-point and real-time methods approaching MERS-CoV virus detection, combining LAMP, DNA transduction, and commercial glucometer are reported. The method is sensitive and selective, with detection limit of 20 copies and at least 25 PFU/mL for artificial PCR product and average diameter) were purchased from Bangs Laboratories Inc. (Fishers, IN, USA) and the Amicon Ultra-2 mL 30K was purchased from Millipore Inc. (Billerica, MA, USA). Illustra MicroSpin G-25 micro columns were purchased from GE Healthcare Bio-Sciences Corp. (Piscataway, NJ, USA). Sulfosuccinimidyl-4-(N-maleimidomethyl)cyclohexane-1-carboxylate (sulfo-SMCC) was brought from Pierce Biotechnology (Rockford, IL, USA). Grade VII invertase from baker's yeast (*S. cerevisiae*), tris(2-carboxyethyl)phosphine hydrochloride (TCEP), and other chemicals and solvents were purchased from Sigma-Aldrich, Inc. (St. Louis, MO, USA). All enzymes including Bst 2.0 DNA polymerase and AMV reverse transcriptase were obtained from New England Biolabs (Ipswich, MA, USA). Human genomic DNA was obtained from Promega (Madison, WI, USA). All the oligonucleotides were purchased from Integrated DNA Technologies, Inc. (Coralville, IA) and listed in Table 3. The concentrations of the DNA suspensions were measured by UV spectrophotometry using the NanoDrop 1000 spectrophotometer (Thermo Scientific, Wilmington, DE, USA).

TABLE 3

| sequence oligonucleotides | | |
|---|---|---|
| ORF1A.55 Primer | F3[a] | TTATGCAAACATAGTCTACGAG (SEQ ID NO: 19) |
| | B3 | CGCAAAGTTAGAAAGTGATGG (SEQ ID NO: 20) |
| | FIP | AAGCATTAGTGGGGGCAAGCCCCACTACTCCCATTTCG (SEQ ID NO: 21) |
| | BIP | ATGCGCACTACACATACTGATATTTGTACAATCTCTTCACTAC AATGA (SEQ ID NO: 22) |
| | LP | GGTGTCTACATTAGTATGTCACTTGTATTAG (SEQ ID NO: 23) |
| ORF1A.55 OSD probe | FP | CGAAGCCAATTTGCAACTGCAATCAGCGCTGAG AAAAAAAAA/ 3Bio/ (SEQ ID NO: 24) |
| | FPc | ATTGCAGTTGCAAATTGGCTTCG AAAAAAAAAAA/ 3ThioMC3-D/ (SEQ ID NO: 25) |
| UpE.9 Primer | F3 | AGTAAGATTAGCCTAGTTTCTGT (SEQ ID NO: 26) |
| | B3 | TCCATATGTCCAAAGAGAGAC (SEQ ID NO: 27) |
| | FIP | GAGGAACTGAATCGCGCGTTGACTTCTCCTTAAACGGCA (SEQ ID NO: 28) |
| | BIP | TTCACATAATCGCCCCGAGCTAATGGATTAGCCTCTACACG (SEQ ID NO: 29) |
| | LP | GCAGGCACGAAAACAGTGGAAACAT (SEQ ID NO: 30) |
| Or Gate OSD probe | ORP | /5Biosg/AAAAAAAAAATCGCTTATCGTTTAAGCAGCTCTGCGC TAC TATGG GTCC CGAAGCCAATTTGCAACTGCAATCAGCGCTGAGC (SEQ ID NO: 31) |
| | 1A-FPc | /5ThioMC6-D/AAAAAAAAAAA ATTGCAGTTGCAAATTGGCTTCG (SEQ ID NO: 32) |
| | upE-FPc | /5ThioMC6-D/AAAAAAAAAAA TAGCGCAGAGCTGCTTAAACGATAAGCGA (SEQ ID NO: 33) |
| Mimical target | A-T | CTCAGCGCTGATTGCAGTTGCAAATTGGCTTCG (SEQ ID NO: 34) |
| | upE-T | GGACCCATAGTAGCGCAGAGCTGCTTAAACGATAAGCGA (SEQ ID NO: 35) |

[a]F3: forward outer primer, B3: reverse outer primer, FIP: forward inner primer, BIP: reverse inner primer.

MERS-CoV RNA, respectively. Three detection strategies proved the sensing platform was also temperature friendly, which is suitable to a wide range designs for integrated instrumentation (devices). The OR gate detector further guaranteed a fail-safe assay.

h) Methods (1) Chemicals and Materials

The Bayer Contour Next Blood Glucose Test Strips and Bayer Contour Next Blood Glucose Monitoring System were bought from Amazon.com and used for the test in this work. Streptavidin-coated magnetic beads (MB, 1.5 μm in (2) Synthesis, Expression, and Purification of *Thermotoga maritima* Invertase The amino acid sequence of the *Thermotoga maritima* MSB8 β-fructosidase (Invertase) was obtained from the National Center for Biotechnology Information (NCBI) database (GenBank #AAD36485.1). This sequence was reverse translated using the GeneDesign) using codons optimal for expression in *E. coli*. Additional 30 bp nucleotides flanks were added to the end of the gene to facilitate cloning via Gibson assembly into the pET21a (Novagen) expression vector. The assembly of the TmINV gene from synthetic oligonucleotides was done according to the Protein Fabrication Automation methodology. The assembled gene was cloned via Gibson assembly cloning into the pET21a vector backbone with a C-terminal HisTag and a sequence verified clone obtained to yield vector pET21-TmINV. The pET21-TmINV vector was transformed into BL21-AI competent cells (Invitrogen) for overexpression. The expression of TmINV was induced in 250 mL mid-log phase cultures of BL21-AI grown in Superior Broth (Athena) via induction with 0.2% L-arabinose. The induced cultures were allowed to grow overnight at 24° C. Following overnight expression the cells were lysed with 1 mg/mL chicken egg white lysozyme and sonication. The protein was purified via immobilized metal affinity chromatography. The protein was dialyzed into 50 mM Sodium Phosphate Buffer, pH 7.4; 175 mM NaCl. The purity of the sample (single ~51 kDa band) was verified by SDS-PAGE to be >98%. The concentration of the protein was determined via measurement of the Abs280 nm using 86,080 as the molar absorptivity of TmINV.

(3) Synthesis of Inv-FPc Conjugate

The procedure for the synthesis of Inv-FPc conjugate was according to the previous literature with a slight modification.[21] For invertase conjugation, 2.5 mg yeast invertase (or TmINV) and 1 mg sulfo-SMCC were dissolved in 1 mL PBS buffer (10 mM PBS, 137 mM NaCl, 2.7 mM KCl, pH 7.4) and shaked at 750 rpm for 2.5 hours at room temperature (RT, 25° C.). After the invertase conjugation finished, the solution was washed by Amicon-30K by using PBS for at least 6 times and re-diluted in 850 μL PBS. During that time, 120 μL 125 μM HS-FPc and 15 μL 100 mM TCEP were mixed and placed on a shaker for 1 hour at RT. Then, G-25 micro columns were used to purify SH-FPc and remove the TCEP and the salts. Then, the HS-FPc was mixed with the invertase conjugation and placed on a shaker over night at 30° C. After that, the un-reacted HS-FPc was removed by using Amicon-30K for at least 6 times. The final Inv-FPc conjugate was stored in PBS buffer with the concentration of 5 mg/mL (determinations with a Nanodrop ND-1000 Spectrophotometer (Wilmington, DE, USA).) at 4° C. for further use.

(4) Preparation of the Inv-FPc/FP/MB Conjugate

200 μL 1 mg/mL streptavidin coated MBs was transferred into a 1.5 mL centrifuge tube and was washed by using isothermal amplification buffer (20 mM Tris-HCl, 10 mM (NH4)2SO4, 50 mM KCl, 2 mM MgSO4, 0.1% Tween 20, pH 8.8) and an external magnetic rack. The resulting MBs were dissolved in 100 μL isothermal amplification buffer and then reacted for 25 min with 6 μL 75 μM biotinylated oligonucleotides (biotin-FP, the partly complementary strand of FPc) on a vertical rotator. After that, the unbound biotin-DNA was removed by washing the FP/MBs for at least 5 times in isothermal amplification buffer. The final FP/MB s were suspended in 50 μL isothermal amplification buffer. Later, 10 μL 5 mg/mL Inv/FPc conjugates were added to that 50 μL FP/MB s solution and well mixed for 1.5 hour at RT by using a vertical rotator. After at least 5 times washing using 100 μL isothermal amplification buffer to remove excess Inv-FPc, the final Inv-FPc/FP/MB probes (about 2 mg/mL) were then dispersed in 100 μL isothermal amplification buffer and stored at 4° C. for further use.

(5) Procedure of 25° C. OSDS for Detecting Mimetic Target by Using Glucometer

A series of 9 μL 2 mg/mL Inv-FPc/FP/MB probes in tubes were placed close to the magnetic rack for 1 min. The clear solution was discarded and replaced by 10 μL mimetic target (1A-T, in isothermal amplification buffer) with different concentrations. The OSD reaction was performed for 1 hour at RT by using a vertical rotator. After that, the solution was separated using a magnetic rack and part of the supernatant was transferred into equal volume of 500 mM sucrose. Then, this mixture was incubated for 40 min at 55° C. to perform the catalytic reaction. At last, 1 μL reaction solution was transferred and measured by using the commercially available glucometer.

(6) Standard LAMP Reaction

Mixtures containing different copies of template (sORF1A), 1 μM each B1c-B2 and F1c-F2, 0.25 μM each B3 and F3, 0.5 μM LP, 1 M betaine, 2 mM MgCl2, and 0.4 mM dNTPs in a total volume of 24 μL 1× Isothermal Buffer (20 mM Tris-HCl, 10 mM (NH4)2SO4, 10 mM KCl, 2 mM MgSO4, 0.1% Triton X-100, pH 8.8) were heated to 95° C. for 5 to 10 min, followed by chilling on ice for 2 min (This pre-denaturing process was not necessary). Then, 1 μL (8 U) of Bst polymerase 2.0 was added to initiate the LAMP reaction. The reactions (with a final volume of 25 μL) were incubated at 55° C. for 1.5 hours, in the thermal cycler. A 5 μl aliquot of the reaction mixed with 3 μl 6×dye, was then analyzed by electrophoresis through a 1% agarose gel containing ethidium bromide. Gel analysis of LAMP products was performed in a room completely separate from the normal laboratory space on a different floor of the building. This precaution was taken to minimize the spread of LAMP amplicon contamination. Note: The LAMP reaction volume could be at least increased to 100 μL without losing sensitivity.

(7) Standard Reverse Transcription (RT)-LAMP Reaction

Mixtures containing different concentrations of MERS-CoV RNA, 1 μM each B1c-B2 and F1c-F2, 0.25 μM each B3 and F3, 0.5 μM LP, 1 M betaine, 2 mM MgCl2, and 0.4 mM dNTPs in a total volume of 24 μL 1× Thermopal buffer NEB; 20 mM Tris-HCl, 10 mM (NH4)2SO4, 10 mM KCl, 2 mM MgSO4, 0.1% Triton® X-100, pH 8.8 at 25° C.), 0.5×AMV RT buffer (NEB; 50 mM Tris-HCl, 75 mM potassium acetate, 8 mM magnesium acetate, 10 mM DTT, pH 8.3 at 25° C.) were heated to 95° C. for 1 min, followed by chilling on ice for 2 min (This pre-denaturing process was not necessary). Then, 1 μL (8 U) of Bst polymerase 2.0 and 0.2 μL (2U) AMV reverse transcriptase was added to initiate the RT-LAMP reaction. The reactions were incubated at 55° C. for 1.5 hour, in the thermal cycler. A 5 μl aliquot of the reaction mixed with 3 μl 6×dye, was then analyzed by electrophoresis through a 1% agarose gel containing ethidium bromide. Gel analysis of LAMP products was performed in a room completely separate from the normal laboratory space on a different floor of the building. This precaution was taken to minimize the spread of LAMP amplicon contamination. Note: The LAMP reaction volume could be at least increased to 100 μL without losing sensitivity.

(8) Procedure of LOG (a) Standard End-Point Detection:

Strategy 1 and Strategy 2:

A series of 9 μL 2 mg/mL Inv-FPc/FP/MBs were placed close to the magnetic rack for 1 min. The clear solution was discarded and replaced by 10 μL standard LAMP or RT-LAMP reaction products (in isothermal amplification buffer) with different concentration of templates. The OSD reaction was performed for 1 h at 25° C. (Strategy 1) or 55° C. (Strategy 2) by using a vertical rotator. After that, the solution was separated using a magnetic rack and 3 μL of the supernatant was transferred into 3 μL of 500 mM sucrose. Then, this mixture was incubated for 23 min (Strategy 2) and 11 min (Strategy 2) at 55° C. to perform the glucose generation step. At last, 1 μL reaction solution was transferred and measured by using the commercially blood glucometer. Note: All the 25° C. steps were performed under room temperature. For Strategy 2, the 55° C. OSDS were performed in a 55° C. incubator.

(b) Standard Real-Time Detection:

Strategy 3:

A series of 9 μL 2 mg/mL Inv-FPc/FP/MBs were placed close to the magnetic rack for 1 min. The clear solution was discarded and replaced by 50 μL standard LAMP or RT-LAMP reaction reagents. The real-time LAMP plus OSD reactions were performed for 1.5 hour at 55° C. by using a vertical rotator, in incubator. After that, the solution was separated using a magnetic rack at 55° C. and 3 μL of the supernatant was transferred into 3 μL of 500 mM sucrose. Then, this mixture was incubated for 15 min at 55° C. to perform the best catalytic reaction. At last, 1 μL reaction solution was transferred and measured by using the commercially available glucometer.

(9) Reproducibility and Stability Tests for Inv-FPc/FP/MBs

The stability and reproducibility tests are all mostly the same with Strategy 1. The reproducibility test was carried out through comparing three parallel assays for detecting both "sORF1A positive samples (2E4 copies)" and "buffer negative controls" using Inv-FPc/FP/MB s prepared on three consecutive days, respectively. The reproducibility test was carried out by measuring "sORF1A positive samples (2E4 copies)" every 2 to 20 days for totally 60 days. During this time, both the Inv-FPc/FP/MBs and LAMP amplicons were changed to show good performance of our platform. The Inv-FPc/FP/MBs were always stored at 4° C. until use for detection.

(10) Fail-Safe OR Gate Sensing Platform

The procedures for the preparation of Inv-1A-FPc and Inv-upE-FPc conjugates were the same as that of Inv-FPc. The preparation of the Inv-1A-FPc/Inv-upE-FPc/ORP/MB conjugates were listed as follow: First, the mixture of 3 μL 150 μM biotin-labeled ORP, 5 μL 5 mg/mL Inv/1A-FPc conjugates, 5 μL 5 mg/mL Inv/upE-FPc conjugates and 18 μL 2× isothermal amplification buffer, was heated to 95° C. for 5 min and slowly cooling to room temperature at a rate of 0.1° C./s to obtain the Inv-1A-FPc/Inv-upE-FPc/ORP. Second, 200 μL 1 mg/mL streptavidin coated MBs was transferred into a 1.5 mL centrifuge tube and was washed by using 1× isothermal amplification buffer and an external magnetic rack. The resulting MBs were dissolved in 50 μL 1× isothermal amplification buffer and then reacted for 25 min with 36 μL Inv-1A-FPc/Inv-upE-FPc/ORP solution by using a vertical rotator. After at least 5 times washing using 100 μL isothermal amplification buffer to remove excess Inv-1A-FPc/Inv-upE-FPc/ORP, the Inv-1A-FPc/Inv-upE-FPc/ORP/MB conjugates were obtained and stored at 4° C. for further use. During the OR gate LAMP-OSD-Glucometer detection of Strategy 1, the inputs were gotten by using no primer, upE primer (upE.9) only, 1A primer (ORF1A.55) only, and upE.9& ORF1A.55 to trigger the RT-LAMP reactions containing the same amount of MERS-CoV RNA (2.5E5 PFU/mL), respectively. The whole LAMP-OSD-Glucometer OR gate detection procedure was similar to the end-point Strategy 1 mentioned above.

Example 3: Detection of Melanoma-Associated Nucleic Acid Biomarkers

Isothermal nucleic acid amplification assays were developed for the detection of melanoma-associated nucleic acid biomarkers. Engineered nucleic acid transducer modules were integrated with the amplification system to: a) allow real-time sequence-specific amplicon validation and BRAF V600E SNP distinction, and b) transmogrify amplicon accumulation into signals measurable by common glucometers. The assay and detection methodology can be validated on clinical surrogates, and user friendly point-of-care melanoma diagnostics can be fabricated. The 5-year survival rate for patients with early melanoma is 94% versus less than 50% for those with melanomas greater than 3 mm in thickness. However, the sensitivity for early malignant melanoma detection was as low as 81% in dermatologists and only 41% in primary care physicians. Molecular diagnostic assays for melanoma biomarkers can fill in the critical need. However, current technologies are unsuitable for point-of-care (POC) applications during primary care. The devices disclosed herein can greatly improve patient management and outcomes.

The technology enables genetic or gene expression biomarker testing on not only diagnostics instruments such as real-time PCR machines, but also on POC-enabled platforms such as paperfluidics and the commercial glucometer. POC devices require minimal user intervention, making them ideally suited to the needs in varied healthcare settings, as well as improving the disease management for both the healthcare provider and the patients by making early diagnostics more accessible and predictive. The POC device is also applicable to intraoperative tissue analysis to aid complete excision of tumors and affected lymph nodes.

In nucleic acid processors for cancer biomarker detection, a nucleic acid analyte is exposed to a device. The device can comprise isothermal enzymatic nucleic acid amplicon generation, sequence-specific amplicon validation/SNP distinction, and signal transduction. The output can be in a variety of ways, such as by fluorimeter, paperfluidic device, glucometer, colorimetric display, or electrochemical.

The diagnostic assays disclosed herein allow sequence-validated detection of as few as 20 synthetic copies of melanoma biomarkers HELLS, NRP2, and the reference β-actin and also provide unambiguous distinction of the melanoma-associated BRAF V600E SNP from the wildtype allele.

Example 4: Nanoluciferase

Disclosed herein is a split reporter system based on the engineered thermostable nanoluciferase NLuc (Hall, M. P. et al. Engineered luciferase reporter from a deep sea shrimp utilizing a novel imidazopyrazinone substrate. ACS chemical biology 7, 1848-1857, doi:10.1021/cb3002478 (2012), hereby incorporated by reference in its entirety for its disclosure concerning nanoluciferase). The N- and C-terminal halves of the split NLuc are conjugated to the 3'- and 5'-ends of two oligonucleotide probes. Reconstitution of active NLuc is contingent upon hybridization of these probes to adjacent sites in the LAMP loop. The split NLuc allows signal detection by a ubiquitous reader, the cell phone, to be coupled to molecular amplification in a single tube without requiring separation of unbound reporters. This first-in-class innovation is greatly enabling for a variety of point-of-care diagnostics, especially since it can be modularly adapted to a variety of molecular targets.

NLuc is a small (19 kDa), single subunit, ATP-independent luciferase that produces a high intensity glow-type luminescence with a half-life >2 h. When presented with its substrate (furimazine) NLuc displays a specific activity that is ~150-fold greater than that of either firefly (Photinus pyralis) or Renilla luciferases. NLuc has no disulphide bonds or post-translational modifications and is physically stable at high temperatures. It retains activity in pH 5-9 and following exposure to 8 M urea. These properties render NLuc an ideal candidate for adoption as a signal transducer of LAMP. Several split sites were selected based on the predicted NLuc structure (FIG. 1). N- and C-terminal halves were SNAP-tagged. The fusion proteins were expressed in E. coli and purified from a Ni-NTA column followed by conjugated with benzylguanine-labeled oligonucleotides (Table 4). We conjugated the split halves of NLuc to HSV1 or β-actin-specific single-stranded oligonucleotides whose respective juxtaposed hybridization to the HSV1 or β-actin LAMP amplicon loops should facilitate NLuc reconstitution (FIG. 41).

TABLE 4

Split NLuc-oligonucleotide probe conjugates.

| Oligo Name | Sequence | NLuc conjugation partner | Target |
| --- | --- | --- | --- |
| HSV1.R1 | CCCCCAACATGACCCAGACAAAAAA/ 34mMO/ (SEQ ID NO: 36) | N3 | HSV1 |
| HSV1.R2 | /5AmMC6/AAAAAACGGCACCACCGACTCT CC/3InvdT/ (SEQ ID NO: 37) | C3 | |
| Actin.R1 | GGAGGTGATAGCATTGCTAAAAAA/ 3AmMO/ (SEQ ID NO: 38) | N3 | β-actin |
| Actin.R2 | /5AmMC6/AAAAAAGTGTAAATTATGTAAT GC/3InvdT/ (SEQ ID NO: 39) | C3 | |

To functionally test the split NLuc reporters, HSV1 and β-actin LAMP amplicons were generated by amplification of 10 pg of templates at 65° C. for 1 h. LAMP reactions prepared without any added templates were also included. The split NLuc probes were then added to the LAMP reactions at 0.2 μM concentration followed by incubation at 55° C. for 15 min. Subsequently Nano-Glo substrate (Promega) was added to these reactions and luminescence was immediately quantified on a SpectraMax M3 plate reader (Molecular Devices) (FIG. 42). The results demonstrate that the split NLuc-oligonucleotide probes are specifically reconstituted in the presence of cognate LAMP amplicons. This distinction can be readily visualized by imaging the bioluminescence with an iPhone 5 camera (FIG. 43).

The split NLuc system can have applications in nucleic acid hybridization and protein-protein interaction beyond its use in optical detection of LAMP amplicons.

VII. SEQUENCES

SEQ ID NO: 1
CTTGATCGCGGCGACCACCG-AGCGGATGACCACCCA

SEQ ID NO: 2
CAGCCAGCTGAGCCAATTCATGGACCA-GACAGTCGGCGCTTGTG

SEQ ID NO: 3
GCATGTCGCGGATGGAG

SEQ ID NO: 4
CGCTCACGTGACAGACCG

SEQ ID NO: 5
CGACGTGGAGGC GATCACACCGCAGACGTTGA

SEQ ID NO: 6
CGGTGTGATC GCCTCCACG TCG

SEQ ID NO: 7
ACTGATGGGACCCACTCCATAAGACCTCACAGTAAAAATA

SEQ ID NO: 8
AACAGTTGTCTGGATCCATTTTGTGACATCTGACTGAAAGCTG TA

SEQ ID NO: 9
CCACAGAGACCTCAAGAGT

SEQ ID NO: 10
ACAGAACAATTCCAAATGCATAT

SEQ ID NO: 11
GAT TTC ACT GTA GCT AGA CCA AAA TCA CCT ATC GA

SEQ ID NO: 12
TCG ATA GGT GAT TTT GGT CTA GCT

SEQ ID NO: 13
GAT TTC TCT GTA GCT AGA CCA AAA TCA CCT ATC GA

SEQ ID NO: 14
TCG ATAGGTGATT TTGGTCTAGCT

SEQ ID NO: 15
CGTGGAGGC GATCACACCG CAGACGTTGA CCACGCTGCTAGCA TCAACGTCTG CGGTGTGATC CCTTGTCA TACGCAGCAC

SEQ ID NO: 16
CAGACGTTGA TGCTAGCAGCGTGG TCAACGTCTG CGGTGTGATC CCACGCTGCTAGCA

SEQ ID NO: 17
CGA GTGCTGCGTA TGACAAGG GATCACACCG

SEQ ID NO: 18
C CCTTGTCA TACGCAGCAC TCG

SEQ ID NO: 19
TTATGCAAACATAGTCTACGAG

SEQ ID NO: 20
CGCAAAGTTAGAAAGTGAT GG

VII. SEQUENCES

SEQ ID NO: 21
AAGCATTAGTGGGGGCAAGCCCCACTACTCCCATTTCG

SEQ ID NO: 22
ATGCGCACTACACATACTGATATTTGTACAATCTCTTCACTACAATGA

SEQ ID NO: 23
GGTGTCTACATTAGTATGTCACTTGTATTAG

SEQ ID NO: 24
CGAAGCCAATTTGCAACTGCAATCAGCGCTGAG AAAAAAAAA

SEQ ID NO: 25
ATTGCAGTTGCAAATTGGCTTCG AAAAAAAAAAA

SEQ ID NO: 26
AGTAAGATTAGCCTAGTTTCTGT

SEQ ID NO: 27
TCCATATGTCCAAAGAGAGAC

SEQ ID NO: 28
GAGGAACTGAATCGCGCGTTGACTTCTCCTTAAACGGCA

SEQ ID NO: 29
TTCACATAATCGCCCCGAGCTAATGGATTAGCCTCTACACG

SEQ ID NO: 30
GCAGGCACGAAAACAGTGGAAAC
AT

SEQ ID NO: 31
AAAAAAAAAATCGCTTATCGTTTAAGCAGCTCTGCGCTAC TATGG
GTCC
CGAAGCCAATTTGCAACTGCAATCAGCGCTGAGC

SEQ ID NO: 32
AAAAAAAAAAA ATTGCAGTTGCAAATTGGCTTCG

SEQ ID NO: 33
AAAAAAAAAAA TAGCGCAGAGCTGCTTAAACGATAAGCGA

SEQ ID NO: 34
CTCAGCGCTGATTGCAGTTGCAAATTGGCTTCG

SEQ ID NO: 35
GGACCCATAGTAGCGCAGAGCTGCTTAAACGATAAGCGA

SEQ ID NO: 36
CCCCCAACATGACCCAGACAAAAAA

SEQ ID NO: 37
AAAAAACGGCACCACCGACTCTC
C

SEQ ID NO: 38
GGAGGTGATAGCATTGCTAAAAAA

SEQ ID NO: 39
AAAAAAGTGTAAATTATGTAATG
C

---

What is claimed is:

1. A method of detecting a nucleic acid, the method comprising
    a) amplifying a target nucleic acid using an isothermal amplification reaction, wherein the isothermal amplification reaction produces at least one loop product, wherein at least part of the single-stranded portion of the loop product represents the target nucleic acid;
    b) exposing the loop product of step a) to a strand displacement reporter, wherein the strand displacement reporter comprises a single nucleic acid strand comprising a hairpin loop structure and a duplex region, wherein said strand displacement reporter comprises an exposed toehold at a terminus of the strand displacement reporter, and further wherein at least a portion of the duplex region of the strand displacement reporter is complementary to at least a portion of the single-stranded nucleic acid of the loop product representing the target nucleic acid;
    c) allowing the loop product and the strand displacement reporter to interact, wherein interaction between the strand displacement reporter and the target nucleic acid portion of the loop product produces a detectable signal, wherein the signal indicates the presence of the target nucleic acid.

2. The method of claim 1, wherein the isothermal amplification reaction is loop-mediated isothermal amplification (LAMP).

3. The method of claim 2, wherein LAMP is conducted with 5 primers.

4. The method of claim 2, wherein LAMP is conducted with 6 primers.

5. The method of claim 1, wherein the strand displacement reporter is one step toehold displacement (OSD) reporter.

6. The method of claim 1, wherein detection of the target nucleic acid takes place in real time.

7. The method of claim 1, wherein multiple target nucleic acids can be detected simultaneously.

8. The method of claim 1, wherein the strand displacement reporter comprises one or more modified nucleic acids.

9. The method of claim 1, wherein primers are used with the isothermal amplification reaction, and further wherein these primers bind a primer binding region of the target nucleic acid.

10. The method of claim 1, wherein interaction between the strand displacement reporter and the target nucleic acid portion of the loop product produces a detectable signal, which signal can be captured using a camera.

11. The method of claim 9, wherein the signal captured by the camera can be further analyzed using computational analysis.

12. The method of claim 1, wherein the strand displacement reporter is not a primer of the target nucleic acid.

13. The method of claim 1, wherein the strand displacement reporter comprises one or more features that deters polymerase extension of 3' end of the strand displacement reporter.

14. The method of claim 13, wherein the one or more features that deters polymerase extension of the molecule comprises a primary detection label, or a chemically modifiable moiety.

15. The method of claim 14, wherein the primary detection label comprises fluorescent, colored or luminescent dyes.

16. The method of claim 14, wherein the primary detection label comprises a quencher or a fluorophore.

17. The method of claim 15, wherein the fluorescent dye comprises fluorescent lanthanide complexes, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarin, pyrene, Malacite green, stilbene, Lucifer Yellow, dansyl chloride, phycoerythin, green fluorescent protein (GFP).

18. The method of claim 14, wherein the chemically modifiable moiety comprises an amino group, carboxy group, maleimide group, oxo group, or thiol group.

19. The method of claim 8, wherein the modified nucleic acid is an inverted dT.

20. The method of claim 1, wherein the step of amplifying in step a) and interaction between the strand displacement reporter and the loop product happens simultaneously.

* * * * *

UNITED STATES PATENT AND TRADEMARK OFFICE
CERTIFICATE OF CORRECTION

| | | |
|---|---|---|
| PATENT NO. | : 11,851,699 B2 | Page 1 of 1 |
| APPLICATION NO. | : 17/168940 | |
| DATED | : December 26, 2023 | |
| INVENTOR(S) | : Andrew Ellington et al. | |

It is certified that error appears in the above-identified patent and that said Letters Patent is hereby corrected as shown below:

On the Title Page

Column 1, item (54), and in the Specification Column 1, Line 1 "STRAND DISPLACEMENT WITH LOOP-MEDIATED ISOTHERMAL AMPLIFICATION" should read -- METHODS AND DEVICES RELATED TO TOEHOLD-BASED STRAND DISPLACEMENT WITH LOOP-MEDIATED ISOTHERMAL AMPLIFICATION --

Signed and Sealed this
Fifth Day of March, 2024

Katherine Kelly Vidal
*Director of the United States Patent and Trademark Office*

SEQUENCE LISTING

<160> NUMBER OF SEQ ID NOS: 40

<210> SEQ ID NO 1
<211> LENGTH: 36
<212> TYPE: DNA
<213> ORGANISM: Artificial Sequence
<220> FEATURE:
<223> OTHER INFORMATION: Synthetic Construct

<400> SEQUENCE: 1
cttgatcgcg gcgaccaccg agcggatgac caccca         36

<210> SEQ ID NO 2
<211> LENGTH: 44
<212> TYPE: DNA
<213> ORGANISM: Artificial Sequence
<220> FEATURE:
<223> OTHER INFORMATION: Artificial Construct

<400> SEQUENCE: 2
cagccagctg agccaattca tggaccagac agtcggcgct tgtg         44

<210> SEQ ID NO 3
<211> LENGTH: 17
<212> TYPE: DNA
<213> ORGANISM: Artificial Sequence
<220> FEATURE:
<223> OTHER INFORMATION: Artificial Construct

<400> SEQUENCE: 3
gcatgtcgcg gatggag         17

<210> SEQ ID NO 4

```
<211> LENGTH: 18
<212> TYPE: DNA
<213> ORGANISM: Artificial Sequence
<220> FEATURE:
<223> OTHER INFORMATION: Artificial Construct

<400> SEQUENCE: 4
cgctcacgtg acagaccg                                                 18

<210> SEQ ID NO 5
<211> LENGTH: 32
<212> TYPE: DNA
<213> ORGANISM: Artificial Sequence
<220> FEATURE:
<223> OTHER INFORMATION: Artificial Construct

<400> SEQUENCE: 5
cgacgtggag gcgatcacac cgcagacgtt ga                                 32

<210> SEQ ID NO 6
<211> LENGTH: 22
<212> TYPE: DNA
<213> ORGANISM: Artificial Sequence
<220> FEATURE:
<223> OTHER INFORMATION: Artificial Construct

<400> SEQUENCE: 6
cggtgtgatc gcctccacgt cg                                            22

<210> SEQ ID NO 7
<211> LENGTH: 40
<212> TYPE: DNA
<213> ORGANISM: Artificial Sequence
<220> FEATURE:
<223> OTHER INFORMATION: Artificial Construct

<400> SEQUENCE: 7
actgatggga cccactccat aagacctcac agtaaaaata                         40

<210> SEQ ID NO 8
<211> LENGTH: 45
<212> TYPE: DNA
<213> ORGANISM: Artificial Sequence
<220> FEATURE:
<223> OTHER INFORMATION: Artificial Construct

<400> SEQUENCE: 8
aacagttgtc tggatccatt ttgtgacatc tgactgaaag ctgta                   45

<210> SEQ ID NO 9
<211> LENGTH: 19
<212> TYPE: DNA
<213> ORGANISM: Artificial Sequence
<220> FEATURE:
<223> OTHER INFORMATION: Artificial Construct

<400> SEQUENCE: 9
ccacagagac ctcaagagt                                                19

<210> SEQ ID NO 10
<211> LENGTH: 23
<212> TYPE: DNA
<213> ORGANISM: Artificial Sequence
<220> FEATURE:
<223> OTHER INFORMATION: Artificial Construct

<400> SEQUENCE: 10
```

```
acagaacaat tccaaatgca tat                                            23

<210> SEQ ID NO 11
<211> LENGTH: 35
<212> TYPE: DNA
<213> ORGANISM: Artificial Sequence
<220> FEATURE:
<223> OTHER INFORMATION: Artificial Construct

<400> SEQUENCE: 11
gatttcactg tagctagacc aaaatcacct atcga                               35

<210> SEQ ID NO 12
<211> LENGTH: 24
<212> TYPE: DNA
<213> ORGANISM: Artificial Sequence
<220> FEATURE:
<223> OTHER INFORMATION: Artificial Construct

<400> SEQUENCE: 12
tcgataggtg attttggtct agct                                           24

<210> SEQ ID NO 13
<211> LENGTH: 35
<212> TYPE: DNA
<213> ORGANISM: Artificial Sequence
<220> FEATURE:
<223> OTHER INFORMATION: Artificial Construct

<400> SEQUENCE: 13
gatttctctg tagctagacc aaaatcacct atcga                               35

<210> SEQ ID NO 14
<211> LENGTH: 24
<212> TYPE: DNA
<213> ORGANISM: Artificial Sequence
<220> FEATURE:
<223> OTHER INFORMATION: Artificial Construct

<400> SEQUENCE: 14
tcgataggtg attttggtct agct                                           24

<210> SEQ ID NO 15
<211> LENGTH: 81
<212> TYPE: DNA
<213> ORGANISM: Artificial Sequence
<220> FEATURE:
<223> OTHER INFORMATION: Artificial Construct

<400> SEQUENCE: 15
cgtggaggcg atcacaccgc agacgttgac cacgctgcta gcatcaacgt ctgcggtgtg    60
atcccttgtc atacgcagca c                                              81

<210> SEQ ID NO 16
<211> LENGTH: 58
<212> TYPE: DNA
<213> ORGANISM: Artificial Sequence
<220> FEATURE:
<223> OTHER INFORMATION: Artificial Construct

<400> SEQUENCE: 16
cagacgttga tgctagcagc gtggtcaacg tctgcggtgt gatcccacgc tgctagca      58

<210> SEQ ID NO 17
```

```
<211> LENGTH: 31
<212> TYPE: DNA
<213> ORGANISM: Artificial Sequence
<220> FEATURE:
<223> OTHER INFORMATION: Artificial Construct

<400> SEQUENCE: 17
cgagtgctgc gtatgacaag ggatcacacc g                                      31

<210> SEQ ID NO 18
<211> LENGTH: 22
<212> TYPE: DNA
<213> ORGANISM: Artificial Sequence
<220> FEATURE:
<223> OTHER INFORMATION: Artificial Construct

<400> SEQUENCE: 18
cccttgtcat acgcagcact cg                                                22

<210> SEQ ID NO 19
<211> LENGTH: 22
<212> TYPE: DNA
<213> ORGANISM: Artificial Sequence
<220> FEATURE:
<223> OTHER INFORMATION: Artificial Construct

<400> SEQUENCE: 19
ttatgcaaac atagtctacg ag                                                22

<210> SEQ ID NO 20
<211> LENGTH: 21
<212> TYPE: DNA
<213> ORGANISM: Artificial Sequence
<220> FEATURE:
<223> OTHER INFORMATION: Artificial Construct

<400> SEQUENCE: 20
cgcaaagtta gaaagtgatg g                                                 21

<210> SEQ ID NO 21
<211> LENGTH: 38
<212> TYPE: DNA
<213> ORGANISM: Artificial Sequence
<220> FEATURE:
<223> OTHER INFORMATION: Artificial Construct

<400> SEQUENCE: 21
aagcattagt gggggcaagc cccactactc ccatttcg                               38

<210> SEQ ID NO 22
<211> LENGTH: 48
<212> TYPE: DNA
<213> ORGANISM: Artificial Sequence
<220> FEATURE:
<223> OTHER INFORMATION: Artificial Construct

<400> SEQUENCE: 22
atgcgcacta cacatactga tatttgtaca atctcttcac tacaatga                    48

<210> SEQ ID NO 23
<211> LENGTH: 31
<212> TYPE: DNA
<213> ORGANISM: Artificial Sequence
<220> FEATURE:
<223> OTHER INFORMATION: Artificial Construct

<400> SEQUENCE: 23
```
ggtgtctaca ttagtatgtc acttgtatta g                          31

<210> SEQ ID NO 24
<211> LENGTH: 42
<212> TYPE: DNA
<213> ORGANISM: Artificial Sequence
<220> FEATURE:
<223> OTHER INFORMATION: Artificial Construct

<400> SEQUENCE: 24
cgaagccaat ttgcaactgc aatcagcgct gagaaaaaaa aa               42

<210> SEQ ID NO 25
<211> LENGTH: 35
<212> TYPE: DNA
<213> ORGANISM: Artificial Sequence
<220> FEATURE:
<223> OTHER INFORMATION: Artificial Construct

<400> SEQUENCE: 25
attgcagttg caaattggct tcgaaaaaaa aaaaa                       35

<210> SEQ ID NO 26
<211> LENGTH: 23
<212> TYPE: DNA
<213> ORGANISM: Artificial Sequence
<220> FEATURE:
<223> OTHER INFORMATION: Artificial Construct

<400> SEQUENCE: 26
agtaagatta gcctagtttc tgt                                   23

<210> SEQ ID NO 27
<211> LENGTH: 21
<212> TYPE: DNA
<213> ORGANISM: Artificial Sequence
<220> FEATURE:
<223> OTHER INFORMATION: Artificial Construct

<400> SEQUENCE: 27
tccatatgtc caaagagaga c                                     21

<210> SEQ ID NO 28
<211> LENGTH: 39
<212> TYPE: DNA
<213> ORGANISM: Artificial Sequence
<220> FEATURE:
<223> OTHER INFORMATION: Artificial Construct

<400> SEQUENCE: 28
gaggaactga atcgcgcgtt gacttctcct taaacggca                  39

<210> SEQ ID NO 29
<211> LENGTH: 41
<212> TYPE: DNA
<213> ORGANISM: Artificial Sequence
<220> FEATURE:
<223> OTHER INFORMATION: Artificial Construct

<400> SEQUENCE: 29
ttcacataat cgccccgagc taatggatta gcctctacac g                41

<210> SEQ ID NO 30
<211> LENGTH: 25
<212> TYPE: DNA

```
<213> ORGANISM: Artificial Sequence
<220> FEATURE:
<223> OTHER INFORMATION: Artificial Construct

<400> SEQUENCE: 30
gcaggcacga aaacagtgga aacat                                          25

<210> SEQ ID NO 31
<211> LENGTH: 83
<212> TYPE: DNA
<213> ORGANISM: Artificial Sequence
<220> FEATURE:
<223> OTHER INFORMATION: Artificial Construct

<400> SEQUENCE: 31
aaaaaaaaaa tcgcttatcg tttaagcagc tctgcgctac tatgggtccc gaagccaatt    60
tgcaactgca atcagcgctg agc                                            83

<210> SEQ ID NO 32
<211> LENGTH: 35
<212> TYPE: DNA
<213> ORGANISM: Artificial Sequence
<220> FEATURE:
<223> OTHER INFORMATION: Artificial Construct

<400> SEQUENCE: 32
aaaaaaaaaa aaattgcagt tgcaaattgg cttcg                               35

<210> SEQ ID NO 33
<211> LENGTH: 41
<212> TYPE: DNA
<213> ORGANISM: Artificial Sequence
<220> FEATURE:
<223> OTHER INFORMATION: Artificial Construct

<400> SEQUENCE: 33
aaaaaaaaaa aatagcgcag agctgcttaa acgataagcg a                        41

<210> SEQ ID NO 34
<211> LENGTH: 33
<212> TYPE: DNA
<213> ORGANISM: Artificial Sequence
<220> FEATURE:
<223> OTHER INFORMATION: Artificial Construct

<400> SEQUENCE: 34
ctcagcgctg attgcagttg caaattggct tcg                                 33

<210> SEQ ID NO 35
<211> LENGTH: 56
<212> TYPE: DNA
<213> ORGANISM: Artificial Sequence
<220> FEATURE:
<223> OTHER INFORMATION: Artificial Construct

<400> SEQUENCE: 35
agaggcatca atgggaatgg gatcatgcct ctaacctagg gatcccattc ccattg         56

<210> SEQ ID NO 36
<211> LENGTH: 39
<212> TYPE: DNA
<213> ORGANISM: Artificial Sequence
<220> FEATURE:
<223> OTHER INFORMATION: Artificial Construct

<400> SEQUENCE: 36
```

```
ggacccatag tagcgcagag ctgcttaaac gataagcga                              39

<210> SEQ ID NO 37
<211> LENGTH: 25
<212> TYPE: DNA
<213> ORGANISM: Artificial Sequence
<220> FEATURE:
<223> OTHER INFORMATION: Artificial Construct

<400> SEQUENCE: 37
cccccaacat gacccagaca aaaaa                                             25

<210> SEQ ID NO 38
<211> LENGTH: 24
<212> TYPE: DNA
<213> ORGANISM: Artificial Sequence
<220> FEATURE:
<223> OTHER INFORMATION: Artificial Construct

<400> SEQUENCE: 38
aaaaaacggc accaccgact ctcc                                              24

<210> SEQ ID NO 39
<211> LENGTH: 24
<212> TYPE: DNA
<213> ORGANISM: Artificial Sequence
<220> FEATURE:
<223> OTHER INFORMATION: Artificial Construct

<400> SEQUENCE: 39
ggaggtgata gcattgctaa aaaa                                              24

<210> SEQ ID NO 40
<211> LENGTH: 25
<212> TYPE: DNA
<213> ORGANISM: Artificial Sequence
<220> FEATURE:
<223> OTHER INFORMATION: Artificial Construct

<400> SEQUENCE: 40
aaaaaaagtg taaattatgt aatgc                                             25
```